(12) United States Patent
Cully et al.

(10) Patent No.: US 8,163,877 B2
(45) Date of Patent: Apr. 24, 2012

(54) **LIGAND GATED ION CHANNELS FROM *DERMACENTOR VARIABILIS***

(75) Inventors: Doris F. Cully, Scotch Plains, NJ (US); Yingcong Zheng, Colonia, NJ (US)

(73) Assignee: Merial Limited, Duluth, GA (US)

( * ) Notice: Subject to any disclaimer, the term of this patent is extended or adjusted under 35 U.S.C. 154(b) by 15 days.

(21) Appl. No.: 12/684,705

(22) Filed: Jan. 8, 2010

(65) Prior Publication Data

US 2010/0184064 A1    Jul. 22, 2010

Related U.S. Application Data

(60) Continuation of application No. 11/840,542, filed on Aug. 17, 2007, now Pat. No. 7,655,440, and a division of application No. 10/239,420, filed as application No. PCT/US01/09956 on Mar. 28, 2001, now Pat. No. 7,267,964.

(60) Provisional application No. 60/193,935, filed on Mar. 31, 2000.

(51) Int. Cl.
*C07K 14/00* (2006.01)
*G01N 33/53* (2006.01)
*C12P 15/00* (2006.01)
(52) U.S. Cl. .......................... 530/350; 435/7.2; 435/69.1
(58) Field of Classification Search .................. None
See application file for complete search history.

*Primary Examiner* — Gary Nickol
*Assistant Examiner* — Sandra Wegert
(74) *Attorney, Agent, or Firm* — Judy Jarecki-Black; Chad Kitchen; Merial Limited

(57) ABSTRACT

The present invention relates in part to isolated nucleic acid molecules (polynucleotides) which encode *Dermacentor variabilis* ligand gated ion channel proteins. The present invention also relates to recombinant vectors and recombinant hosts which contain a DNA fragment encoding *D. variabilis* LGIC/GluCl channels, substantially purified forms of associated *D. variabilis* channel proteins and recombinant membrane fractions comprising these proteins, associated mutant proteins, and methods associated with identifying compounds which modulate associated *Dermacentor variabilis* LGIC/GluCl, which will be useful as insecticides and acaricides.

8 Claims, 17 Drawing Sheets

DvLGIC/GluCl 1

```
   1  GCGAGGCTGT CGGTGGAAAG CGCGGCGAGC ACGCGTCCGC GCGCCTGCGC
  51  TCCAGTCCGG ACCCGAGCTG GAGCACGGCC TGGAGGGATA GGTCTGGTCG
 101  ACCGTGGTTG CAGCTCCAGA CGCGCAGTTG GAGCTCGGCG AAGGGGCTGC
 151  TGCTGCGAGC ACTGTGCGCA TGCCACTTTC AGCGCTGAAC GTGTGGCGCG
 201  CTTGCGTCAC GTTGTCCCTC CTCAGGACGA CGCTCGCGCA GGAAAGGCGG
 251  TCAAACGGAG CGCTGGATGA CCTGGAGAAG CTTGACGACT TATTAAGAAC
 301  CTATGACCGG CGTGCCCTTC CCACGACACA CTTGGGAACG CCAACAAAAG
 351  TGGCTTGCGA AATCTACATA CGCAGCTTCG GGTCCATAAA TCCAGCCACA
 401  ATGGACTATG AGGTTGATCT TTATTTGCGG CAGACTTGGC AAGATGATCG
 451  CTTGACGAGC CCCAACGTAT CCAGGCCCCT GGACCTCAAT GATCCAAAGC
 501  TGGTGCAGCG TATATGGAAA CCGGAAGTAT TCTTCGCAAA TGCCAAACAC
 551  GCAGAGTTCC AATATGTCAC AGTACCTAAT GTACTGGTCC GCGTTAACCC
 601  GAACGGAAAG ATTCTATACA TGCTCAGGCT CAAGCTAAGG TTTGCATGTA
 651  TGATGGATTT ATATCGCTTT CCTATGGACT CCCAAGTTTG CAGCATCGAA
 701  CTCGCCTCAT TCTCGAAAAC AACCGAAGAA CTGCATCTGG AGTGGTCTGA
 751  TACCAATCCG ATAATACTAT TCGAAGGCCT GAAGTTACCA CAATTCGAGA
 801  TTCAGAATAT AAATACGTCA ATCTGCATGG AGAAATTTCA CATCGGAGAG
 851  TACAGCTGCC TGAAGGCCGA CTTCCACTTG CAGCGGTCAC TGGGCTACCA
 901  CATGGTGCAG TCGTATCTGC CTACAGTGCT CATCGTGGTC ATCTCGTGGG
 951  TGTCCTTCTG GCTCGACGTT GAGTCCATTC CGGCGCGCAC CACACTGGGC
1001  GTCACGACGC TGCTCACTAT TTCTTCCAAG GGCTCCGGTA TACAGTCCAA
1051  CTTGCCTCCG GTCTCATACG TGAAGGCAAT CGATGTGTGG ATGGGAGCCT
1101  GCACGGGCTT CGTGTTCTCG GCACTACTGG AGTTCACCGT CGTCAGCTGC
1151  CTGGCCAGGA TGCAGGCACG AGACAAGGAG TCAAGTATGG TTACAACAAA
1201  GCACGGAGTG GCGATTGTCA ACGCTGTTCC TGATAACCAG GCGTCGGTTC
1251  CTTGCACTGT CCGGGCGAAA ACTATTGACC AGGTCTGCCG CGTAGCGTTT
```

FIG. 1A

```
1301  CCGGCCATCT TCCTCGTGTT TAACGCCATT TACTGGCCGT ATTTTATGTG
1351  CTTTACAGAG TAGAACATCA CCGAACAACG CAAAAGTTCT GCGGAAAAAG
1401  TGTCCGTATA ACGTGTCTTG AGGCTCATTG TCACGTATTT ACACCGGCAT
1451  GAAAGGTTCG TTAAATCAAC CAATATAGCG TCCTCAGCCA ATTACGCACA
1501  CTAGTTTAGA GCAGCCAGTC GCATTTCCTT TACTACTATC GAGAGAGGTT
1551  GGACTAAGTC ATGAGTTCAT TCCCTTCGGT AGCTTCTGTC AATTGTCTCA
1601  GGGAAGGATA GGTTGGTGCT TCGAGCTCTT TAGCGCATGC AAACTCTGTT
1651  GGGATGCTTA GGTACGCGCA GGGAACGTGA CGATCTATAA TGTTTTTTGG
1701  AGTAGTAATG GAACACGGCA CTGACGGTCG ATAAATTTGA TAGCATGAGG
1751  AAGTGAACTA ATTACTATAA AATGCACAAC GGCTTTATTG TGGAGTATTG
1801  CGCGTTTTCT TTTTATAATG TAGGAGGGAT AGAATATAAG TGCCAAGAAG
1851  CAGATACCTA AAATCGTAAA ACAGCGCCGC CATGTAGATG TCTGATTTAG
1901  AAGATACCGT TGCACTGCAT CACAGGCGTA GCATACAACA AATTTAAGCT
1951  CTTCTATAGG AAATAGAAAT ATTGAGTATT ACTTCGTTAA TGCGGGAATC
2001  GTATTTGTTA AATGTATCTT TCGATTAACA ATTGGGACTT TCGCTGTTTC
2051  AATACAGACT TTGTTGAGCC TTCGTATAAC ATTACGAAAA AAAAGAAAA
2101  TCTGAAAAGA ATAATATCTA CGTTTTCAAT ACCAGCCATT CTAGTCCAGA
2151  AGGCAAGCGT GCTGCAAAAT CCGAAAGCAA ATTTATTTA TGTTAAATAT
2201  AACATCCCGG TCATTTGCCC TAACTTTGTG GCGACAATTG ACAGCGTCAA
2251  CTAAACTGCG TATTCCATGT TGTCGCTTAA TGGCTTTGCC ATGATGCCAT
2301  CTTAGTCATT TTCAGCTGTT CAAAGTTTTA AGGAATAAGC TATGCTTAAG
2351  CTACAATTGA TTGTTAATGA AGTGTCAGCG CGAAGACTTG CGAGTTTGAT
2401  TTCGTACATA TGAGTGTTCT TTATACACCC TGACACTACC TTTTTGGAGG
2451  CGATGAGCCG AGAATTCAGA AAACGTCATG GCCAGTTTTA ACAGAACAGT
2501  GACCCTGTTA AAAATGTCTG TATGAATACT GTTGTTATTT ATGGTAGTTT
2551  TGAAATCGTT TAATATATGT TATGTTACGT GATCAAGTGT CAATGGCTAT
2601  ACATTATCGA CCTCCCATTA ACTTGATCAA TCCAATCGTC CAGACATTTA
```

FIG. 1B

2651 ATGTCCGAGG AACTTCAGGT TTATTAACTG TAGGTTAAAA CTCTGATGTA
2701 TATATAACAG CATGGAATGC AAGATCTCGT CATATTTCAT GCAATTTCAC
2751 TAGATGCAGC GATGTTTTCG ATGGAGATTA TTCGTCTCCT GAAAAAAAAA
2801 ATTGACATTC ACCGGCATGT AGGCTGAAGC TATGAAGAAA ACCCAGCTGG
2851 GTTTCCTTTG TAGCTTCGTT TTTTTCCTAG ATAAGGTTAA TATCTTGATC
2901 TCTGTGCTAC AGTAAGAGTG AAACTGAACT CGGCCTGAAA AACTTGCGTT
2951 TTCTTATCGC ACTACCGTCA TTGAAACGCT CAGTACTAGG TCTTGGTGAA
3001 ACACATGACT AAAATTTGAA AGCTTTAGAA TGAATTTATT TATTTTTATT
3051 TATTTACAAA TACTGCAATC CCGTTACGGG ATTGCAGTAT TTGCATTATG
3101 AAAGAAACAC ATTATGAAAG AAACGAGAAA CGCAATCTTC GCATTATGAA
3151 AGAAACGAGC AGAAGACAGA TGGCTAATTT TATTTGCTGA TTGTAGCCCA
3201 TTTTCCTCTT ACTAGAGAGT TATGGGTGAC AGCAGAATTC TCAGAATAGT
3251 GCATTCTCTT AAAATAACTT GACATCGTGT GGTAATTTCC CTAAATCTCA
3301 TGTAGGTAGA TGCTTTATTT ATGTAATTTG AGGAGACATA CCCATGAAAA
3351 CGAAAAGATG ACGGGCGCTA ATGGTTTATAG AAGTCCTTCC TGCCACTGTT
3401 GGCTGAAATG TATTTGTATG TTTTTTGGTC AGTCACTGTG TCCCAAAGCT
3451 TCTTCGTGCT GAAGCTTAAG TGAGTCTATG CTGTTCAACA CCATTGTATA
3501 TTTTTGTAAT AAAATAGTTT ATTAAATGAC CTGGTTCTAC TTGAAAAAAA
3551 AAAAAAAAAA AAAAAAAAAA AAAAAAAAAA AAAAAAAAAA AAAAAAAA (SEQ ID NO:1)

FIG. 1C

DvLGIC/GluCl 1
DVLGIC/GluCl 11

MPLSALNVWR ACVTLSLLRT TLAQERRSNG ALDDLEKLDD LLRTYDRRAL PTTHLGTPTK
VACEIYIRSF GSINPATMDY EVDLYLRQTW QDDRLTSPNV SRPLDLNDPK LVQRIWKPEV
FFANAKHAEF QYVTVPNVLV RVNPNGKILY MLRLKLRFAC MMDLYRFPMD SQVCSIELAS
FSKTTEELHL EWSDTNPIIL FEGLKLPQFE IQNINTSICM EKFHIGEYSC LKADFHLQRS
LGYHMVQSYL PTVLIVVISW VSFWLDVESI PARTTLGVTT LLTISSKGSG IQSNLPPVSY
VKAIDVWMGA CTGFVFSALL EFTVVSCLAR MQARDKESSM VTTKHGVAIV NAVPDNQASV
PCTVRAKTID QVCRVAFPAI FLVFNAIYWP YFMCFTE (SEQ ID NO:2)

FIG.2

DvLGIC/GluCl 11

```
   1  CGAAGGGGCT GCTGCTGCGA GCACTGTGCG CATGCCACTT TCAGCGCTGA
  51  ACGTGTGGCG CGCTTGCGTC ACGTTGTCCC TCCTCAGGAC GACGCTCGCG
 101  CAGGAAAGGC GGTCAAACGG AGCGCTGGAT GACCTGGAGA AGCTTGACGA
 151  CTTATTAAGA ACCTATGACC GGCGTGCCCT TCCCACGACA CACTTGGGAA
 201  CGCCAACAAA AGTGGCTTGC GAAATCTACA TACGCAGCTT CGGGTCCATA
 251  AATCCAGCCA CAATGGACTA TGAGGTTGAT CTTTATTTGC GGCAGACTTG
 301  GCAAGATGAT CGCTTGACGA GCCCCAACGT ATCCAGGCCC CTGGACCTCA
 351  ATGATCCAAA GCTGGTGCAG CGTATATGGA AACCAGAAGT ATTCTTCGCA
 401  AATGCAAAAC ACGCAGAGTT CCAATATGTC ACAGTACCTA ATGTACTGGT
 451  CCGCGTTAAC CCGAACGGAA AGATTCTATA CATGCTCAGG CTCAAGCTAA
 501  GGTTTGCATG TATGATGGAT CTATATCGCT TTCCTATGGA CTCCCAAGTT
 551  TGCAGCATCG AACTCGCCTC ATTCTCGAAA CAACCGAAG AACTGCATCT
 601  GGAGTGGTCC GATACCAATC CGATAATACT ATTCGAAGGC CTGAAGTTAC
 651  CACAGTTCGA GATTCAGAAT ATAAATACGT CAATCTGCAT GGAGAAATTT
 701  CACATCGGAG AGTACAGCTG CCTGAAGGCC GACTTCCACT TGCAGCGGTC
 751  ACTGGGCTAC CACATGGTGC AGTCGTATCT GCCTACAGTG CTCATCGTGG
 801  TCATCTCGTG GGTGTCCTTC TGGCTCGACG TTGAGTCCAT TCCGGCGCGC
 851  ACCACACTGG GCGTCACGAC GCTGCTCACT ATTTCTTCCA AGGGCTCCGG
 901  TATACAGTCC AACTTGCCTC CGGTCTCATA CGTGAAGGCA ATCGATGTGT
 951  GGATGGGAGC CTGCACGGGC TTCGTGTTCT CGGCACTACT GGAGTTCACC
1001  GTCGTCAGCT GCCTGGCCAG GATGCAGGCA CGAGACAAGG AGTCAAGCAT
1051  GGTTACAACA AAGCACGGAG TGGCGATTGT CAACGCTGTT CCTGATAACC
1101  AAGCGTCGGT TCCTTGCACT GTCCGGGCGA AAACTATTGA CCAGGTCTGC
1151  CGCGTAGCGT TTCCGGCCAT CTTCCTCGTG TTTAACGCCA TTTACTGGCC
1201  GTACTTTATG TGCTTTACTG AGTAGAACAT CACCGAACAA GGCAATAGTT
1251  CTGCGGAAAA AGTGTCCGTA TAACGTGTCT TGAGGCTCAT TGTCACGTAT
```

FIG.3A

```
1301  TTACACCGGC  ATGAAAGGTA  GGTCAAGGGA  GCGTTCGTTA  AATCAACCAA
1351  TATAGCGTCC  TCAGCCAATT  ACGCACACTA  GTTTAGAGCA  GCCAGTCGAA
1401  TTTCCTTTAC  TACTATCGAG  AGAGGTTGGA  CTAAGTCATG  AGTTCATTCC
1451  CTTCGGTAGC  TTCTGTCAAT  TGTCTCAGGG  AAGGATAGGT  TGGTGCTTCG
1501  AGCTCTTTAG  CGCATGCAAA  CTCTGTTGGG  ATGCTTAGGT  ACGCGCAGGG
1551  AACGTGACGA  TCTATAATGT  TTTTTGGAGT  AGTAATGGAA  CACGGCACTG
1601  ACGGTCGATA  AATTTGATGG  TATGAGGAAG  TGCACTGATT  ACTATAAAAT
1651  GCACAACGGC  TTTATTGTGG  AGTATGGCTC  GTTTTCTTTT  TATAATGTAG
1701  GAGGGATAGA  ATATAAGTGC  CAAGAAGCAG  ATACTTAAAA  TCCTAAAACA
1751  GCGCCGCCAT  GTAGATGTCT  GATTTAGAAG  ATACCGTTGC  ACTGCATCAC
1801  AAGCGTAGCA  TACAACAAAT  TTAAGCTCTT  CTATAGGAAA  TAGAAATATT
1851  GAGTATTACT  TCGTTAATGC  GGGAATCGTA  TTTGTTAAAT  GTATCTTTCG
1901  ATTAACAATT  GGGACTTTCG  CTGTTTCAAT  ACAGACTTTT  TTGAGCCTTC
1951  GTATAACATT  ACGAAAAAAA  AAGAAAATCT  GAAAAGAATA  ATATCTACGT
2001  TTTCAATACC  AGCCATTCTA  GTCCAGAAGG  CAAGCGTGCT  GCAAAATCCG
2051  AAAGCAAAAT  TTATTTATGT  TAAATATAAC  ATCCCGGTCA  TTTGCCCTAA
2101  CTTTGTGGCG  ACAATTGACA  GCGTCAACTA  AACTGCGTAT  TCCATGTTGT
2151  CGCTTAATGG  CTTTGCCATG  ATGCCATCTT  AGTCATTTTC  AGCTGTTCAA
2201  AGTTTTAAGG  AATAAGCTAT  GCTTAAGCTA  CAATTGATTG  TTAATGAAGT
2251  GTCAGCGCGA  AGACTTGCGA  GTTTGATTTC  GTACATATGA  GTGTTCTTTA
2301  TACAACCTGA  CACTACCTTT  TTGGAGGCGA  TGAGCCGAGA  ATTCAGAAAA
2351  CGTCATGGCC  AGTTTTAACA  GAACAGTGAC  CCTGTTAAAA  TGTCTGTATA
2401  AATACTGTTG  TTATTTATGG  TAGTTTTGAA  ATCGTTTAAT  ATATGTTATG
2451  TTACGTGATC  AAGTGTCAAT  GGCTATACAT  TATCGACCTC  CCATTAACTT
2501  GATCAATCCA  ATCGTCCAGA  CATTTAATGT  CCGAGGAACT  TCAGGTTTAT
2551  TAACTGTAGG  TTAAAACTCT  GATGTATATA  TAACAGCATG  GAATGCAAGA
2601  TCTCGTCATA  TTTCATGCAA  TTTCACTAGA  TGCAGCGATG  TTTTCGATGG
```

FIG.3B

```
2651  AGATTATTCG TCTCCTGAAA AAAAAAATTG ACATTCACCG GCATGTAGGC
2701  TGAAGCTATG AAGGAAACCC AGCTGGGTTT CCTTTGTAGC TTCGTTTTTT
2751  TCCTAGATAA GGTTAATATC TTGATCTCTG TGCTACAGTA AGAGTGAAAC
2801  TGAACTAGGC CTGAAAAACT TGCGTTTTCT TATCGCACTA CCTTCATTGA
2851  AACGCTCAGT ACTAGGTCTT GGTGAAACAC ATGACTAAAA TTTGAAAGCT
2901  TTAGAATGAA TTTATTTATT TTTATTTATT TACAAATACT GCAATCCCGT
2951  TACGGGATTG CAGTATTTGC ATTATGAAAG AAACACATTA TGAAAGAAAC
3001  GAGAAACGCA ATCTTCGCAT TATGAAAGAA ACGAGCAGAA GACAGATGGC
3051  TAATTTTATT TGCTGATTGT AGCCCATTTT TCTCTTACTA GAGAGTTATG
3101  GGTGACAGCA GAATTCTCAG AATAGTGCAT TCTCTTAAAA TAACTTGACA
3151  TCGTGTGGTA ATTTCCCTAA ATCTCATGTA GGTAGCTGCT TTATTTATGT
3201  AATTTGAGGA GACATACCCA TGAAAACGAA AAGACGACGG GCGCTAATGA
3251  TTATAGAAGT CCTTCCTGCC ACTGTTGGCT GAAATGTATT TGTATGTTTT
3301  TTGGTCAGTC ACTGTGTCCC AAAGCTTCTT CGTGCTGAAG CTTAAGTGAG
3351  TCTATGCTGT TCAACACCAT TGTATATTTT TGTAATAAAA TAGTTTATTA
3401  AATGACCTGG TTCTACTTGA AAAAAAAAAA AAAAAAAAA AA (SEQ ID NO:3)
```

FIG.3C

DvLGIC/GluCl 7-1

```
   1 CTCGGTCGCG CGCGCACACA GCAAGTGCTC CGGTGAGGCG GCTGATATGA
  51 TCCCGGCGTC CGTGGCTCTC GGCCGAAGGA TGTGCTCTCT GCTGCTCGCT
 101 GTCGGATGCG CCACGACTAG CGCCTGGTTC GCTCAGGCTG TCGACCACAT
 151 CGACAAAGGA TACCCAGCAC CAGGACTCTT CGATGATGTC GACCTTCAAA
 201 TATTGGACAA CATCTTATGG AGCTACGACC GACGCATCAC CCCTGGTCAT
 251 CATTTAAACG TTCCTACAGT TGTTAAGTGC GAGATATATC TCAGGAGTTT
 301 TGGAGCTGTG AACCCTGCAA CAATGGACTA CGACGTAGAC CTGTACCTGC
 351 GTCAGACGTG GACGGACTTG CGGATGAAGA ACGCCAACCT GACCCGGTCC
 401 CTAGACTTAA ACGACCCCAA CCTCCTCAAG AAAGTGTGGA AACCTGACGT
 451 CTACTTTCCC AATGCCAAGC ACGGGGAGTT CCAGTTCGTC ACTGTTCCCA
 501 ACGTTCTCTT GAGGATATAC CCTACCGGCG ATATACTCTA CATGTTAAGG
 551 CTAAAGCTAA CATTCTCCTG CATGATGAAC ATGGAGCGGT ACCCCCTGGA
 601 CCGACAGGTC TGCAGCATCG AGCTTGCCTC ATTTTCCAAG ACGACAAAGG
 651 AGGTTGAGCT CCAATGGGGA AACGCTGAGG CTGTCACCAT GTACAGTGGT
 701 CTGAAGATGG CACAATTCGA GCTTCAACAA ATCAGCCTGA CGAAGTGCAG
 751 CGGCGCCTTT CAGATAGGCG AGTACAGCTG CCTGCGCGCG GAGCTCAACT
 801 TGAAGCGTTC CATTGGCCAC CACCTAGTGC AGTCTTACCT GCCGTCCACA
 851 CTCATCGTGG TCGTGTCGTG GGTGTCCTTC TGGCTCGACG TGGACGCCAT
 901 ACCGGCGCGC ATCACGCTGG GTGTCACCAC GCTCCTCACT ATTTCGTCGG
 951 AGAGCTCCGA CCACCAGGCC AACCTAGCGC CGGTGTCGTA CGTGAAAGCG
1001 CTCGACGTGT GGATGGGCAC GTGCACCATG TTCGTGTTCG CCGCGGTGCT
1051 CGAGTTCACC TTCGTCTCCT ACCTCGCTCG CAGAAAGCAG ATCGTGCCCG
1101 CCTCTATCGC GGACGTCGAG GCTTCCCAAG ATCTCGTTCT TGTCGTGGGA
1151 AACAAGGACA AAAATCGACC CCCGTCACCG TCCATCCCGA CGTCCACCCA
1201 CGTGGTCTTG GCTTACAGAC ACCGTGCCAA GCAGATCGAC CAAGTGAGCC
```

FIG.4A

```
1251  GGGTCGCTTT CCCAATCGGC TTTGTTCTCT TCAACGCACT CTACTGGCCC
1301  TATTACTTGC TCTAGTTGGC CATGGTCTCA GTGCCTACAG CTGCTGCTCC
1351  CAACGTGCAG CCATACGCCG GGAAACGGGT GGCTGCGTAC CCCAGGGAAA
1401  CGGTCGGCCG CTGGATTGAA AAGGACTGCC ATCACCGACG CACGCTCTGG
1451  TGGAAGAGAA AGCTACACTC TTTGCTCTGC CGCATTCATT CTTTTCTTAC
1501  CGTGATCCTC TTTGTCTCTT ATCTTTTCTT TTGTGTGTGT GTAGCCGTTG
1551  GCGCTGTCTT CAGGGCATTC CGCTCTTAAG CGGGTGCTGA CACATTGACC
1601  ATCGCTTCAG ACTTCCTCGT TGTACGGATG TTGCCATCAT AATCCCAAAG
1651  AGCATCATGG TTAAAACTGT CCATACGCAC ATTTGTAAAT AAGAATTGAT
1701  TCACACATCA GAAACATGGT TGTACTTAGG GGTGCCCAAA AATATTTTTG
1751  CCCTTTTTTG AATAATGTAT GAAAGACAAC TTAACTTTCA CCAAAATAAA
1801  CTAGAAAGCT CAGCGTGTTT GTCTTTATTC GCTGCTACAC TAACTTCGAG
1851  ACCAACGGAT AAGAAAGTTA ACGGAATAAG AGAGCGGTAC CTTTATTACC
1901  TCTCTTTAAA AGAAGTTAGC AGCGATGAAT TTGTTGCTCT TTTCTCTAAG
1951  GCATTCAATA ATTTATAAGG CGTCGGGTAT TTCAGTTACT CAATTATTCA
2001  ATGAAACAAT GTATCCTACA TGACGAGTAC TGGTCAGTCG AGATGCGTTG
2051  TTTTCCCGAC AGTTCTCATT CAGGGTTCTT TCCGAGCGAA GACTGATTGC
2101  GTGCTGCCAG ACTGATTCGT TCTTGGCGAT TTGGTCGAAA CGTTTGCGCT
2151  TCCTCATTCA GCGTCCGGCG TCAGCAATAT TTGCGCGTAA TCCC (SEQ ID NO:4)
```

FIG.4B

DvLGIC/GluC17-1

MIPASVALGR RMCSLLLAVG CATTSAWFAQ AVDHIDKGYP APGLFDDVDL QILDNILWSY
DRRITPGHHL NVPTVVKCEI YLRSFGAVNP ATMDYDVDLY LRQTWTDLRM KNANLTRSLD
LNDPNLLKKV WKPDVYFPNA KHGEFQFVTV PNVLLRIYPT GDILYMLRLK LTFSCMMNME
RYPLDRQVCS IELASFSKTT KEVELQWGNA EAVTMYSGLK MAQFELQQIS LTKCSGAFQI
GEYSCLRAEL NLKRSIGHHL VQSYLPSTLI VVVSWVSFWL DVDAIPARIT LGVTTLLTIS
SESSDHQANL APVSYVKALD VWMGTCTMFV FAAVLEFTFV SYLARRKQIV PASIADVEAS
QDLVLVVGNK DKNRPPSPSI PTSTHVVLAY RHRAKQIDQV SRVAFPIGFV LFNALYWPYY
LL (SEQ ID NO:5)

FIG.5

DvLGIC/GluCl 10-2

```
   1 CGGACCGGTC GGCCCACTTT CTCCTTTCAT GACGCGCCGT GATCACGCGG
  51 CGTGACACCC AGCGTCGCCT CTACGTTTCA TTCATTTCGT GTCTCCGCCT
 101 GCGGTGCGCC TGCCGCGTGA CGCAACCGGG CGCATGACAC CGCCGAACCC
 151 TCTGTCGTCG GCGCATCGCG TCCTGGCGCT GCTCCTGCTG GTGACAGTGC
 201 CGGCTTCTCT GGGGCAGAGG AGACATGGAA CTGTCGGCGA TTTGGACAAG
 251 TTGGACAAAC TCCTGAGCAA ATATGACAGA AGGGCGTTGC CAACGGGGCA
 301 CATGAGATTA CGAAGTGGAC CTCTACCTGC GACAACGATG GCATGATGAC
 351 CGCTTTGAGA TGAGCGGCAT TAGTGGACCC CTCGACCTGA ACGATCCCAA
 401 ACTGGTGCAA CGTATATGGA AACCCGAAGT CTTTTTTGCC AACGCAAAGC
 451 ATGCGGAGTT CCAGTACGTG ACGGTGCCCA ACGTCCTAGT ACGCATCAGT
 501 CCTACGGGGG ACATTCTCTA CATGCTCAGG TTGAAGCTGA CTTTTTCTTG
 551 CATGATGGAC CTTTACCGGT ACCCCCTAGA CGCTCAAGTT TGCAGCATTG
 601 AACTCGCTTC GTTCTCGAAG ACGACGGACG AGCTACAGCT GCACTGGTCT
 651 AAGGCATCGC CTGTGATCCT CTATGAAAAC ATGAAGCTCC CACAATTTGA
 701 AATTCAAAAC GTGAACACGT CCCTGTGCAA TGAGACATTC CACATTGGAG
 751 AGTACAGCTG CCTGAAAGCC GAGTTCAACC TACAGCGCTC TATTGGCTAC
 801 CACCTCGTCC AATCGTATCT GCCCACCATC TTGATCGTGG TCATCTCTTG
 851 GGTCTCCTTC TGGCTCGACG TGGAAGCGAT TCCAGCCCGA ATTACATTGG
 901 GAGTCACCAC GCTTCTTACC ATCTCATCCA AGGGTGCCGG TATACAAGGA
 951 AACCTGCCGC CGTCTCGTA CGTCAAGGCA ATCGACGTCT GGATGGGCGC
1001 CTGCACCATG TTCGTGTTTG CCGCACTGCT TGAGTTCACC TTTGTCAACT
1051 ACCTGTGGAG GAAGCGGCCC GCGACTGCCA AGTCACCACC TCCGGTGGTC
1101 GCAGCCATTC CCGAGAGCAA AGTGGCTGTG CTCCTCCCAT GCAACGGAAA
1151 CTTGGGGCCA TGCAGCCCCA TCACTGGCGG TACAGACATC AGCCCTTCGC
1201 CCACAGGTCC TGAAGCTGTC AGAAACAGAC ACAAGGTTCA GGCCAAGAGA
1251 ATTGACCAGA CCTGCAGGAT AGCATTTCCC ATGGCTTTCC TGGCGTTTAG
```

FIG.6A

```
1301  CGTCGCATAC TGGCCATACT ATCTTTTGTG AGGCCGCGGT ACCCCGAGCT
1351  AATGTCAGGA ACGGAGAGGC GGGTACCACG AAGTCGGGGG GGGGGGGGAG
1401  GGGGGAGAGT GCTTGTGGCT ATCACAATCC CGTTGGTTCT CTGTAAGAAC
1451  GCTTTTGTTT TGCACAGAAG CTCACTGCAT CACATTTTGC GTCTCCCTAG
1501  TGTTTAATTA TTTGTTTCTG CACTTGTGTT CCCGTGTGCA TTCTGACTGA
1551  ATATCACTCC AACCCTTCAG TGTGTATAAG TCCCAAAGTG AATTGGATAT
1601  TTCCTCTTCG CGATCCTCTT GAGGGCACCT CTAGTCACTA ATCTAACACG
1651  TAGGAGAGTT TAAGGATGCG TTAGGCAGCA CTTTTCTTGT GCTTTAAGTG
1701  GATCTCATCA TATTCTGGTA GAGAATATAA ACTTCAACAC TGAAGTAGTA
1751  TTTACAAGGC AGACTAACAT GTTGCTAGAA ACAGTATTTT TGCAGGAGGG
1801  AAGATGCAAT GATTATACAG GGTGTTCAAA ATTAAGCTTT ATGGTTTTAT
1851  AGGAATTAGG CACTGCGAGG GGAAGGGCAA CCGTTATCGT CTTTGTCTAT
1901  GCCTCCGCCC TATTGTCAGA CTAAATGCCG CACACAACAG CCTCGTCACA
1951  TCAGGGAAGA TCTTTGTGCC AATCCTCACT CTCTTGCGTG CGTAATCACG
2001  TAAACGACAA TTAAAATTTG GAGCCAGCTA TCTCGAAGCA AAGATATGCT
2051  GGAAGAATTC TTCTAAGTGT AACTGTGTAG AAACTTTTCA ATACACAAAT
2101  ACACACTTAC TGCAGTCAAT AAAAAGTTAA TTACTCGATT TTATTTAATT
2151  GGGCTGCTGA CAGCAATAAC TCTCATCTCA CTTTGTGTCC CCCTGGCCAC
2201  ATAACTTATT TGCACAGGTG GTCTTCGCGT GCATCCCAGT GGCTAAATTT
2251  AAGAAAACCA TAAAGCTTAA TTTTGAACAC CTGGTATATC ATGATGCTTT
2301  CAATGCTTTA TTGTTGTATT ATAAAAAAAG ATATACTATC AACGACTCAG
2351  GCCGGAGAAT CATGTTGGAA AAAAAATGTT TCATTGTTTC CTTTCGTCAT
2401  CGCGCCCTTA GGTTAATTTG CCCTGTACAG TTCCTGAGGG AACGCATTAG
2451  TGCACAAAAA AAGTATTTCG GCTTCCACAT CGCAACGAAA ACGGGCGTCG
2501  CCTCCTGTCT CTACAAGACA ATGAGATGCG CAGGCCGCAC GCTTTTTCGG
2551  GGTCCGCAAT TATTAAACAT GGCGTATATT TTGATAACCC GCACCTTCTT
2601  CCTACGCAGC ATTTTTCTGT TAGACCCACT GGGTTCATTT AACCAATCCT
2651  AGGCCTAAAA CCGTATTCAA GCCCAGCACA AAGTCCGCTT TTGCGAACTC
```

FIG.6B

```
2701  CCGTTCAGAT GTGGATGAGC CGTTGGCTTA CAGGACTCTG ACCTAAGTAT
2751  GGGCCTGTGT CAAACGGCGT CAGAAAGATG AGCACAACAG CCCCTTATTG
2801  CGTAACGCTG CCGGCAATGC TCGCCATTTT AAGCTGTCCC GAACTGCGAA
2851  ATTATTCCAC GGTAGCGCTT TTGTAGATGT GGAAGACTTG CCTAATCACT
2901  TCAAAGGTGT CGCCACTTAC AATACTATAC GTACAGTTCC GCCTGGAGAA
2951  TTTGGCGCAC GCATACTTGT AGTACCATGA GGCGGAGTTA TTACTTCGGG
3001  AGGAATTGCG CAGGCAGCTA ATCCCCATCT ACGCAACTCT GGACAGTCGG
3051  ATGTTATGCA TGGTAGGAGA ATGGACTATA GAAGGGTGGA GTCTGCAAGT
3101  CAGGCGAGGA TACAGCGGCG TAGCGAAAAC GTAGCCATGC TTGTGGAGTA
3151  CACGACCCGA CTCTTGTGAA ACACGGATCC ATCTATGTCG GAAACAAAAA
3201  TTTAAGCACT TCATGCGCGC AGTAAAGAAA GAACCCTTTG GGGGCCTGAT
3251  ACCAAACTTG CCCAAGAACC TCCCAGAGTA CCTCGCAGAG GCCATGTCAA
3301  AGGAAAAGAC GATCTAGCAG TAGGATCCTG ATTTGGCTTT GGACAACGTC
3351  GCTGTAATGC GAGTGCTTAT AAAGTTCTTT GTTCTGGAAG AGGTTAAATG
3401  CTCCATCTAA CTCCAGGCTC TGTACTGCGG ACTTCGCCGG CTGAGGTCGT
3451  TCGTTAGAAG ATGGGGCGTG CTGCCCGAAC CTCAGAATAT TTCGGAGCGC
3501  CACTGTACGA GGTGCGGCAG CTGGCACTTT GAATCACCTA TGCGGAAGCT
3551  GCGCGAGGTT CTCCACACTA GGACTCCCAC AATGTGCGCG CCCTTGAACA
3601  AGCGATTGCC AACTTCAGAG CCCGCGGCGA CCAATCAAAG CTGAAGTATG
3651  TCATCGCAAA ACTTATATTT ATCGAACCTC AATTGGAAAG ACCATGTATT
3701  TTCACTGCGC TGTGGAACAT GAAATTTATG CGTTACATAT TCGCTCCGGG
3751  GAATAGCAAA AATATTGCAA AATATTGGT GACACAGAAA GCAGTCGCAT
3801  ATCAAGCCCA TTATATGCGT TGACGCTGTA GTTTGTAAAG GCACTTGAA
3851  TGTGGACGCC TGTTTAGAAT CGCGGAGAGA TTTCATTTTC GCGGAGCTTA
3901  TACCACTCTC AAATGTGCTG GGGCACGGCA GAATCGTGGA TCCAGTTTTT
3951  TTAACTTCCG TCAAAACAGA TTAGCAGTAG TTCACAGCGG CGAAACACTC
4001  ACAAGTGTAG TTATAAAAAC CTAACAGTTT GAATCAATAA ATATTTGACA
4051  TCAAAAAAAA AAAAAAAAAA AAAAAAA (SEQ ID NO:6)
```

FIG.6C

DvLGIC/GluCl 10-2

MSGISGPLDL NDPKLVQRIW KPEVFFANAK HAEFQYVTVP NVLVRISPTG DILYMLRLKL
TFSCMMDLYR YPLDAQVCSI ELASFSKTTD ELQLHWSKAS PVILYENMKL PQFEIQNVNT
SLCNETFHIG EYSCLKAEFN LQRSIGYHLV QSYLPTILIV VISWVSFWLD VEAIPARITL
GVTTLLTISS KGAGIQGNLP PVSYVKAIDV WMGACTMFVF AALLEFTFVN YLWRKRPATA
KSPPPVVAAI PESKVAVLLP CNGNLGPCSP ITGGTDISPS PTGPEAVRNR HKVQAKRIDQ
TCRIAFPMAF LAFSVAYWPY YLL (SEQ ID NO:7)

FIG. 7

```
Dv 1      MPLS.........ALNVWRA..CVTLSLLRTTLAQERRSNGALD............
Dv 11     MPLS.........ALNVWRA..CVTLSLLRTTLAQERRSNGALD............
Dv 10-2   .............................................MS..........
Dv 7-1    MIPASVALGRRMCSLLLAVGCATTSAWFAQAVDHIDKGYPAPGLFDD...........

Dv 1      .......................DLEKLDDLLRT..YDRRALPTTHLGT..PT
Dv 11     .......................DLEKLDDLLRT..YDRRALPTTHLGT..PT
Dv 10-2   ......................................................
Dv 7-1    ................V........DLQILDNILWS..YDRRITPGHHLNV..PT

Dv 1      KVACEIYIRSFGSINPATMDYEVDLYLRQTWQDDRLTSPNVS...RPLDLNDPKLVQRIW
Dv 11     KVACEIYIRSFGSINPATMDYEVDLYLRQTWQDDRLTSPNVS...RPLDLNDPKLVQRIW
Dv 10-2   ............G.......................IS...GPLDLNDPKLVQRIW
Dv 7-1    VVKCEIYLRSFGAVNPATMDYDVDLYLRQTWTDLRMKNANLT...RSLDLNDPNLLKKVW

Dv 1      KPEVFFANAKHAEFQYVTVPNVLVRVNPNGKILYMLRLKLRFACMMDLYRFPMDSQVCSI
Dv 11     KPEVFFANAKHAEFQYVTVPNVLVRVNPNGKILYMLRLKLRFACMMDLYRFPMDSQVCSI
Dv 10-2   KPEVFFANAKHAEFQYVTVPNVLVRISPTGDILYMLRLKLTFSCMMDLYRYPLDAQVCSI
Dv 7-1    KPDVYFPNAKHGEFQFVTVPNVLLRIYPTGDILYMLRLKLTFSCMMNMERYPLDRQVCSI

Dv 1      ELASFSKTTEELHLEWSDTNPIILFEGLKLPQFEIQNINTSICMEKFHIGEYSCLKADFH
Dv 11     ELASFSKTTEELHLEWSDTNPIILFEGLKLPQFEIQNINTSICMEKFHIGEYSCLKADFH
Dv 10-2   ELASFSKTTDELQLHWSKASPVILYENMKLPQFEIQNVNTSLCNETFHIGEYSCLKAEFN
Dv 7-1    ELASFSKTTKEVELQWGNAEAVTMYSGLKMAQFELQQISLTKCSGAFQIGEYSCLRAELN

Dv 1      LQRSLGYHMVQSYLPTVLIVVISWVSFWLDVESIPARTTLGVTTLLTISSKGSGIQSNLP
Dv 11     LQRSLGYHMVQSYLPTVLIVVISWVSFWLDVESIPARTTLGVTTLLTISSKGSGIQSNLP
Dv 10-2   LQRSIGYHLVQSYLPTILIVVISWVSFWLDVEAIPARITLGVTTLLTISSKGAGIQGNLP
Dv 7-1    LKRSIGHHLVQSYLPSTLIVVVSWVSFWLDVDAIPARITLGVTTLLTISSESSDHQANLA

Dv 1      PVSYVKAIDVWMGACTGFVFSALLEFTVVSCLAR....MQARDKES..............
Dv 11     PVSYVKAIDVWMGACTGFVFSALLEFTVVSCLAR....MQARDKES..............
Dv 10-2   PVSYVKAIDVWMGACTMFVFAALLEFTFVNYLWRK...RPATAK................
Dv 7-1    PVSYVKALDVWMGTCTMFVFAAVLEFTFVSYLARR...KQ....................

Dv 1      ...S..MVT......TKHGVAIVN.................................AVPD
Dv 11     ...S..MVT......TKHGVAIVN.................................AVPD
Dv 10-2   ...SPPPVVA.........AIPES................................KVAVLL
Dv 7-1    ......IVPAS........IADVEAS..............................QDLVLV

Dv 1      .................N.......................QA...SVPC..TVR
Dv 11     .................N.......................QA...SVPC..TVR
Dv 10-2   PC................NGNLGPCSPITGGTDISPSPTGPEA..VRNRH..KVQ
Dv 7-1    VG................NKDKNRPPSPS....IPTSTHVVLAY....R....HR

Dv 1      AKTIDQVCRVAFPAIFLVFNAIYWPYFMCFT..E..(SEQ ID NO:2)
Dv 11     AKTIDQVCRVAFPAIFLVFNAIYWPYFMCFT..E..(SEQ ID NO:2)
Dv 10-2   AKRIDQTCRIAFPMAFLAFSVAYWPYYLL.......(SEQ ID NO:8)
Dv 7-1    AKQIDQVSRVAFPIGFVLFNALYWPYYLL.......(SEQ ID NO:6)
```

LIGAND GATED ION CHANNELS FROM *DERMACENTOR VARIABILIS*

CROSS-REFERENCE TO RELATED APPLICATIONS

This application is a Continuation of U.S. Ser. No. 11/840,542, filed on Aug. 17, 2007 now U.S. Pat. No. 7,655,440 and published as US2008/0103291 A1, which was allowed on Aug. 20, 2009 and is a Divisional application of U.S. application Ser. No. 10/239,420, filed Sep. 23, 2002, now U.S. Pat. No. 7,267,964, which is the 35 U.S.C. 371 National Stage application of International Application No. PCT/US01/09956, filed Mar. 28, 2001, which claims the benefit of priority of U.S. Provisional Application No. 60/193,935, filed Mar. 31, 2000. The present application claims priority under 35 U.S.C. §119 (e), to provisional application U.S. Ser. No. 60/193,935, filed Mar. 31, 2000.

FIELD OF THE INVENTION

The present invention relates in part to isolated nucleic acid molecules (polynucleotides) which encode *Dermacentor variabilis* (American dog tick) ligand-gated chloride channels. The present invention also relates to recombinant vectors and recombinant hosts which contain a DNA fragment encoding *D. variabilis* ligand-gated chloride channels, substantially purified forms of associated *D. variabilis* ligand-gated chloride channels and recombinant membrane fractions comprising these proteins, associated mutant proteins, and methods associated with identifying compounds which modulate associated *Dermacentor variabilis* ligand-gated chloride channels, which will be useful as insecticides and acaricides.

BACKGROUND OF THE INVENTION

Glutamate-gated chloride channels, or H-receptors, have been identified in arthropod nerve and muscle (Lingle et al, 1981, Brain Res. 212: 481-488; Horseman et al., 1988, Neurosci. Lett. 85: 65-70; Wafford and Sattelle, 1989, J. Exp. Bio. 144: 449-462; Lea and Usherwood, 1973, Comp. Gen. Pharmacol. 4: 333-350; and Cull-Candy, 1976, J. Physiol. 255: 449-464).

Invertebrate glutamate-gated chloride channels are important targets for the widely used avermectin class of anthelmintic and insecticidal compounds. The avermectins are a family of macrocyclic lactones originally isolated from the actinomycete *Streptomyces avermitilis*. The semisynthetic avermectin derivative, ivermectin (22,23-dihydro-avermectin $B_{1a}$), is used throughout the world to treat parasitic helminths and insect pests of man and animals. The avermectins remain the most potent broad spectrum endectocides exhibiting low toxicity to the host. After many years of use in the field, there remains little resistance to avermectin in the insect population. The combination of good therapeutic index and low resistance strongly suggests that the ligand-gated ion channels, and especially glutamate-gated chloride (LGIC/GluCl) channels remain good targets for insecticide development.

Glutamate-gated chloride channels have been cloned from the soil nematode *Caenorhabditis elegans* (Cully et al., 1994, Nature 371: 707-711; see also U.S. Pat. No. 5,527,703 and Arena et al., 1992, Molecular Brain Research. 15: 339-348) and *Ctenocephalides felis* (flea; see WO 99/07828).

In addition, a gene encoding a glutamate-gated chloride channel from *Drosophila melanogaster* was previously identified (Cully et al., 1996, J. Biol. Chem. 271: 20187-20191; see also U.S. Pat. No. 5,693,492).

*Dermacentor variabilis* (American dog tick) is indigenous to the majority of the U.S. with known common hosts of livestock, deer, dogs, humans and small mammals. This tick is associated with various diseases, including Rocky Mountain spotted fever, babesiosis, tick paralysis, anaplasmosis, tularemia and cytauxzoonosis.

Despite the identification of the aforementioned cDNA clones encoding non-tick LGIC/GluCl channels, it would be advantageous to identify additional genes which encode *D. variabilis* LGIC/GluCl channels in order to allow for improved screening to identify novel LGIC/GluCl channel modulators that may have insecticidal, acaricidal, and/or nematocidal activity for animal health, especially as related to treatment of tick infestations in livestock and domesticated animals, such as dogs and cats. The present invention addresses and meets these needs by disclosing novel genes which encode *D. variabilis* LGIC/GluCl proteins and when expressed in *Xenopus* oocytes result in formation of functional LGIC/GluCl channels.

Heterologous expression of a LGIC/GluCl channel of the present invention will allow the pharmacological analysis of compounds active against parasitic invertebrate species relevant to animal and human health, especially in the treatment of tick infestations directly related to *Dermacentor variabilis*. Heterologous cell lines expressing an active LGIC/GluCl channel can be used to establish functional or binding assays to identify novel LGIC/GluCl channel modulators that may be useful in control of the aforementioned species groups.

SUMMARY OF THE INVENTION

The present invention relates to an isolated or purified nucleic acid molecule (polynucleotide) which encodes a novel *Dermacentor variabilis* (American dog tick) invertebrate LGIC channel protein, including but not necessarily limited to a *D. variabilis* LGIC/GluCl channel protein. The DNA molecules disclosed herein may be transfected into a host cell of choice wherein the transfected host cell provides a source for substantial levels of an expressed functional single, homomultimer or heteromultimer LGIC. Such functional ligand-gated ion channels may possibly respond to other known ligands which will in turn provide for additional screening targets to identify modulators of these channels, modulators which may act as effective insecticidal, acaricidal, mitacidal and/or nematocidal treatments for use in animal and human health and/or crop protection.

The present invention further relates to an isolated nucleic acid molecule (polynucleotide) which encodes mRNA which expresses a novel *Dermacentor variabilis* LGIC/GluCl channel protein, this DNA molecule comprising the nucleotide sequence disclosed herein as SEQ ID NO:1, SEQ ID NO:3, SEQ ID NO:4 and SEQ ID NO:6.

The present invention also relates to biologically active fragments or mutants of SEQ ID NOs: 1, 3, 4 and 6 which encodes mRNA expressing a novel *Dermacentor variabilis* invertebrate LGIC/GluCl channel protein. Any such biologically active fragment and/or mutant will encode either a protein or protein fragment which at least substantially mimics the pharmacological properties of a *D. variabilis* LGIC/GluCl channel protein, including but not limited to the *D. variabilis* LGIC/GluCl channel proteins as set forth in SEQ ID NO:2, SEQ ID NO:5 and SEQ ID NO:7. Any such polynucleotide includes but is not necessarily limited to nucleotide substitutions, deletions, additions, amino-terminal truncations and carboxy-terminal truncations such that these mutations encode mRNA which express a functional *D. variabilis* LGIC/GluCl channel in a eukaryotic cell, such as Xeel0pus oocytes, so as to be useful for screening for agonists and/or antagonists of *D. variabilis* LGIC/GluCl activity.

A preferred aspect of this portion of the present invention is disclosed in FIG. 1 (SEQ ID NO:1; designated DvLGIC/ GluCl 1), FIG. 3 (SEQ ID NO:3; designated DvLGIC/GluCl 11), FIG. 4 (SEQ ID NO:4; designated DvLGIC/GluCl 7-1) and FIG. 6 (SEQ ID NO:6, designated DvLGIC/GluCl 10-2) which encode novel forms of *Dermacentor variabilis* LGIC/ GluCl channel proteins.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant host cells, both prokaryotic and eukaryotic, which contain the substantially purified nucleic acid molecules disclosed throughout this specification.

The present invention also relates in part to a substantially purified form of a *D. variabilis* LGIC/GluCl channel protein, which comprises the amino acid sequence disclosed in FIG. 2 (SEQ ID NO:2), FIG. 5 (SEQ ID NO:5) and FIG. 7 (SEQ ID NO:7).

A preferred aspect of this portion of the present invention is a *D. variabilis* LGIC/GluCl channel protein which consists of the amino acid sequence disclosed in FIG. 2 (SEQ ID NO:2), FIG. 5 (SEQ ID NO:5) and FIG. 7 (SEQ ID NO:7).

Another preferred aspect of the present invention relates to a substantially purified, fully processed (including any proteolytic processing, glycosylation and/or phosphorylation) mature LGIC/GluCl channel protein obtained from a recombinant host cell containing a DNA expression vector comprising a nucleotide sequence as set forth in SEQ ID NOs: 1, 3, 4 and/or 6 and expresses the DvLGIC/GluCl precursor or mature form of the respective protein. It is especially preferred that the recombinant host cell be a eukaryotic host cell, including but not limited to a mammalian cell line, an insect cell line such as S2 cells, or *Xenopus* oocytes.

Another preferred aspect of the present invention relates to a substantially purified membrane preparation, partially purified membrane preparations or cell lysate which has been obtained from a recombinant host cell transformed or transfected with a DNA expression vector which comprises and appropriately expresses a complete open reading frame as set forth in SEQ ID NOs: 1, 3, 4 and/or 6, resulting in a functional form of the respective DvLGIC/GluCl channel. The subcellular membrane fractions and/or membrane-containing cell lysates from the recombinant host cells (both prokaryotic and eukaryotic as well as both stably and transiently transformed/ transfected cells) contain the functional and processed proteins encoded by the nucleic acids of the present invention. This recombinant-based membrane preparation may comprise a *D. variabilis* LGIC/GluCl channel and is essentially free from contaminating proteins, including but not limited to other *D. variabilis* source proteins or host proteins from a recombinant cell which expresses the LGIC/GluCl 1 (SEQ ID NO:2), LGIC/GluCl 11 (also SEQ ID NO:2) LGIC/GluCl 7-1 (SEQ ID NO:5) and/or the LGIC/GluCl 10-2 (SEQ ID NO:7) LGIC/GluCl channel protein. Therefore, a preferred aspect of the invention is a membrane preparation which contains a *D. variabilis* LGIC/GluCl channel comprising a LGIC/GluCl protein comprising the functional form of the LGIC/GluCl channel proteins as disclosed in FIG. 2 (SEQ ID NO:2; LGIC/ GluCl 1 and LGIC/GluCl 11), FIG. 5 (SEQ ID NO:5, LGIC/ GluCl 7-1) and/or FIG. 7 (SEQ ID NO:7; LGIC/GluCl 10-2). These subcellular membrane fractions will comprise either wild-type or mutant variations which are biologically functional forms of the *D. variabilis* LGIC/GluCl channels. Any functional single channel, homomultimer or heteromultimer combination of the DvLGIC/GluCl proteins disclosed herein is contemplated at levels substantially above endogenous levels and hence will be useful in various assays described throughout this specification. It is also possible that the disclosed channel proteins may, alone or in combination, form functional heteromultimeric channels with as yet identified channel proteins. A preferred eukaryotic host cell of choice to express the glutamate-gated channels of the present invention is a mammalian cell line, an insect-based cell line such as S2 cells, or *Xenopus* oocytes.

The present invention also relates to biologically active fragments and/or mutants of a *D. variabilis* LGIC/GluCl channel protein, comprising the amino acid sequence as set forth in SEQ ID NOs: 2, 5, and/or 7, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for selective modulators, including but not limited to agonists and/or antagonists for *D. variabilis* LGIC/GluCl channel pharmacology.

A preferred aspect of the present invention is disclosed in FIG. 2 (SEQ ID NO:2), FIG. 5 (SEQ ID NO:5) and FIG. 7 (SEQ ID NO:7), amino acid sequences which comprise the *D. variabilis* LGIC/GluCl proteins of the present invention, respectively. Characterization of one or more of these channel proteins allows for screening methods to identify novel LGIC/GluCl channel modulators that may have insecticidal, acaricidal and/or nematocidal activity for animal health, human health and/or crop protection. As noted above, heterologous expression of a functional single channel, homomultimeric or heteromultimeric channel which is comprised of one or a combination of the DvLGIC/GluCl proteins disclosed herein is contemplated at levels substantially above endogenous levels and will allow the pharmacological analysis of compounds active against parasitic invertebrate species relevant to animal and human health in general as well as possible DvLGIC/GluCl specific modulators which, may be useful to control various parasitic infestations. Heterologous cell lines expressing a functional DvLGIC/GluCl channel (e.g., functional forms of SEQ ID NOs: 2, 5, and/or 7) can be used to establish functional or binding assays to identify novel LGIC/GluCl channel modulators that may be useful in control of the aforementioned species groups.

The present invention also relates to polyclonal and monoclonal antibodies raised in response to the disclosed forms of DvLGIC/GluCl, or a biologically active fragment thereof. The present invention also relates to DvLGIC/GluCl fusion constructs, including but not limited to fusion constructs which express a portion of the DvLGIC/GluCl linked to various markers, including but in no way limited to GFP (Green fluorescent protein), the MYC epitope, GST, and Fc. Any such fusion constructs may be expressed in the cell line of interest and used to screen for modulators of one or more of the DvLGIC/GluCl proteins disclosed herein.

The present invention relates to methods of expressing *D. variabilis* LGIC/GluCl channel proteins and biological equivalents disclosed herein, assays employing these gene products, recombinant host cells which comprise DNA constructs which express these proteins, and compounds identified through these assays which act as agonists or antagonists of LGIC/GluCl channel activity.

It is an object of the present invention to provide an isolated nucleic acid molecule (e.g., SEQ ID NOs: 1, 3, 4, and 6) which encodes a novel form of *D. variabilis* LGIC/GluCl, or fragments, mutants or derivatives of DvLGIC/GluCl, these proteins as set forth in SEQ ID NOs: 2, 5 and 7, respectively. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for selective modulators for invertebrate LGIC/GluCl pharmacology.

It is a further object of the present invention to provide the *D. variabilis* LGIC/GluCl proteins or protein fragments encoded by the nucleic acid molecules referred to in the preceding paragraph.

It is a further object of the present invention to provide recombinant vectors and recombinant host cells which comprise a nucleic acid sequence encoding *D. variabilis* LGIC/GluCl proteins or a biological equivalent thereof.

It is an object of the present invention to provide a substantially purified form of *D. variabilis* LGIC/GluCl proteins, respectively, as set forth in SEQ ID NOs: 2, 5, and 7.

It is another object of the present invention to provide a substantially purified recombinant form of a *D. variabilis* LGIC/GluCl protein which has been obtained from a recombinant host cell transformed or transfected with a DNA expression vector which comprises and appropriately expresses a complete open reading frame as set forth in SEQ ID NOs: 1, 3, 4, and 6, resulting in a functional form of the respective DvLGIC/GluCl channel. It is especially preferred that the recombinant host cell be a eukaryotic host cell, such as a mammalian cell line. It is an object of the present invention to provide for biologically active fragments and/or mutants of *D. variabilis* LGIC/GluCl proteins, respectively, such as set forth in SEQ ID NOs: 2, 5, and 7, including but not necessarily limited to amino acid substitutions, deletions, additions, amino terminal truncations and carboxy-terminal truncations such that these mutations provide for proteins or protein fragments of diagnostic, therapeutic and/or prophylactic use.

It is further an object of the present invention to provide for substantially purified subcellular membrane preparations, partially purified subcellular membrane preparations, or crude lysates from recombinant cells which comprise pharmacologically active *D. variabilis* LGIC/GluCl channels, respectively, especially subcellular fractions obtained from a host cell transfected or transformed with a DNA vector comprising a nucleotide sequence which encodes a protein which comprises the amino acid as set forth in FIG. 2 (SEQ ID NO:2), FIG. 5 (SEQ ID NO:5), and/or FIG. 7 (SEQ ID NO:7).

It is another object of the present invention to provide a substantially purified membrane preparation, partially purified subcellular membrane preparations, or crude lysates obtained from a recombinant host cell transformed or transfected with a DNA expression vector which comprises and appropriately expresses a complete open reading frame as set forth in SEQ ID NOs: 1, 3, 4, and/or 6, resulting in a functional, processed form of the respective DvLGIC/GluCl channel. It is especially preferred is that the recombinant host cell be a eukaryotic host cell, including but not limited to a mammalian cell line, an insect cell line such as S2 cells, or *Xenopus* oocytes.

It is also an object of the present invention to use *D. variabilis* LGIC/GluCl proteins or membrane preparations containing *D. variabilis* LGIC/GluCl proteins or a biological equivalent to screen for modulators, preferably selective modulators of *D. variabilis* LGIC/GluCl channel activity and/or an invertebrate LGIC/GluCl channel. Any such protein or membrane associated protein may be useful in screening for and selecting these modulators active against parasitic invertebrate species relevant to animal and human health. Such species include, in addition to the American dog tick channels disclosed herein, worms, fleas, other tick species, and lice. These membrane preparations may be generated from heterologous cell lines expressing these LGIC/GluCls and may constitute full length protein, biologically active fragments of the full length protein or may rely on fusion proteins expressed from various fusion constructs which may be constructed with materials available in the art.

As used herein, "substantially free from other nucleic acids" means at least 90%, preferably 95%, more preferably 99%, and even more preferably 99.9%, free of other nucleic acids. As used interchangeably with the terms "substantially free from other nucleic acids" or "substantially purified" or "isolated nucleic acid" or "purified nucleic acid" also refer to a DNA molecules which comprises a coding region for a *D. variabilis* LGIC/GluCl protein that has been purified away from other cellular components. Thus, a *D. variabilis* LGIC/GluCl DNA preparation that is substantially free from other nucleic acids will contain, as a percent of its total nucleic acid, no more than 10%, preferably no more than 5%, more preferably no more than 1%, and even more preferably no more than 0.1%, of non-*D. variabilis* LGIC/GluCl nucleic acids. Whether a given *D. variabilis* LGIC/GluCl DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, a *D. variabilis* LGIC/GluCl protein preparation that is substantially free from other proteins will contain, as a percent of its total protein, no more than 10%, preferably no more than 5%, more preferably no more than 1%, and even more preferably no more than 0.1%, of non-*D. variabilis* LGIC/GluCl proteins. Whether a given *D. variabilis* LGIC/GluCl protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting. As used interchangeably with the terms "substantially free from other proteins" or "substantially purified", the terms "isolated *D. variabilis* LGIC/GluCl protein" or "purified *D. variabilis* LGIC/GluCl protein" also refer to *D. variabilis* LGIC/GluCl protein that has been isolated from a natural source. Use of the term "isolated" or "purified" indicates that *D. variabilis* LGIC/GluCl protein has been removed from its normal cellular environment. Thus, an isolated *D. variabilis* LGIC/GluCl protein may be in a cell-free solution or placed in a different cellular environment from that in which it occurs naturally. The term isolated does not imply that an isolated *D. variabilis* LGIC/GluCl protein is the only protein present, but instead means that an isolated *D. variabilis* LGIC/GluCl protein is substantially free of other proteins and non-amino acid material (e.g., nucleic acids, lipids, carbohydrates) naturally associated with the *D. variabilis* LGIC/GluCl protein in vivo. Thus, a *D. variabilis* LGIC/GluCl protein that is recombinantly expressed in a prokaryotic or eukaryotic cell and substantially purified from this host cell which does not naturally (i.e., without intervention) express this LGIC/GluCl protein is of course "isolated *D. variabilis* LGIC/GluCl protein" under any circumstances referred to herein. As noted above, a *D. variabilis* LGIC/GluCl protein preparation that is an isolated or purified *D. variabilis* LGIC/GluCl protein will be substantially free from other proteins will contain, as a percent of its total protein, no more than 10%, preferably no more than 5%, more preferably no more than 1%, and even more preferably no more than 0.1%, of non-*D. variabilis* LGIC/GluCl proteins.

As used interchangeably herein, "functional equivalent" or "biologically active equivalent" means a protein which does not have exactly the same amino acid sequence as naturally occurring *D. variabilis* LGIC/GluCl, due to alternative splicing, deletions, mutations, substitutions, or additions, but retains substantially the same biological activity as *D. variabilis* LGIC/GluCl. Such "functional equivalents" will have significant amino acid sequence identity with naturally occurring *D. variabilis* LGIC/GluCl and genes and cDNA encoding such functional equivalents can be detected by reduced stringency hybridization with a DNA sequence encoding naturally occurring *D. variabilis* LGIC/GluCl. For example, a naturally occurring *D. variabilis* LGIC/GluCl protein disclosed herein comprises the amino acid sequence shown as SEQ ID NO:2 and is encoded by SEQ ID NO:1. A nucleic acid encoding a functional equivalent has at least about 50% identity at the nucleotide level to SEQ ID NO:1.

As used herein, "a conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

As used herein, "LGIC" refers to a—ligand-gated ion channel—.

As used herein, "GluCl" refers to—L-glutamate gated chloride channel—.

As used herein, "LGIC/GluCl" refers to—ligand gated ion channel/L-glutamate gated chloride channel—.

As used herein, "DvLGIC/GluCl" refers to—*Dermacentor variabilis* ligand gated channel/L-glutamate gated chloride channel—.

As used herein, the term "mammalian" will refer to any mammal, including a human being.

BRIEF DESCRIPTION OF THE DRAWINGS

FIG. 1A-C shows the nucleotide sequence of the *D. variabilis* LGIC/GluCl cDNA clone, DvLGIC/GluCl 1, set forth in SEQ ID NO:1.

FIG. 2 shows the amino acid sequence of the *D. variabilis* LGIC/GluCl protein, DvLGIC/GluCl 1 and DvLGIC/GluCl 11, as set forth in SEQ ID NO:2.

FIG. 3A-C shows the nucleotide sequence of the *D. variabilis* LGIC/GluCl cDNA clone, DvLGIC/GluCl 11, as set forth in SEQ ID NO:3.

FIG. 4A-B shows the nucleotide sequence of the *D. variabilis* LGIC/GluCl cDNA clone, DvLGIC/GluCl 7-1, as set forth in SEQ ID NO:4.

FIG. 5 shows the amino acid sequence of the *D. variabilis* LGIC/GluCl protein, DvLGIC/GluCl 7-1, as set forth in SEQ ID NO:5.

FIG. 6A-C shows the nucleotide sequence of the *D. variabilis* LGIC/GluCl cDNA clone, DvLGIC/GluCl 10-2, as set forth in SEQ ID NO:6.

FIG. 7 shows the amino acid sequence of the *D. variabilis* LGIC/GluCl protein, DvLGIC/GluCl 10-2, as set forth in SEQ ID NO:7.

FIG. 8 shows the amino acid sequence comparison for DvLGIC/GluCl 1 (SEQ ID NO:2), DvLGIC/GluCl 11 (SEQ ID NO:2), DvLGIC/GluCl 7-1 (SEQ ID NO:5) and DvLGIC/GluCl 10-2 (SEQ ID NO:7) proteins.

DETAILED DESCRIPTION OF THE INVENTION

Figure 9:
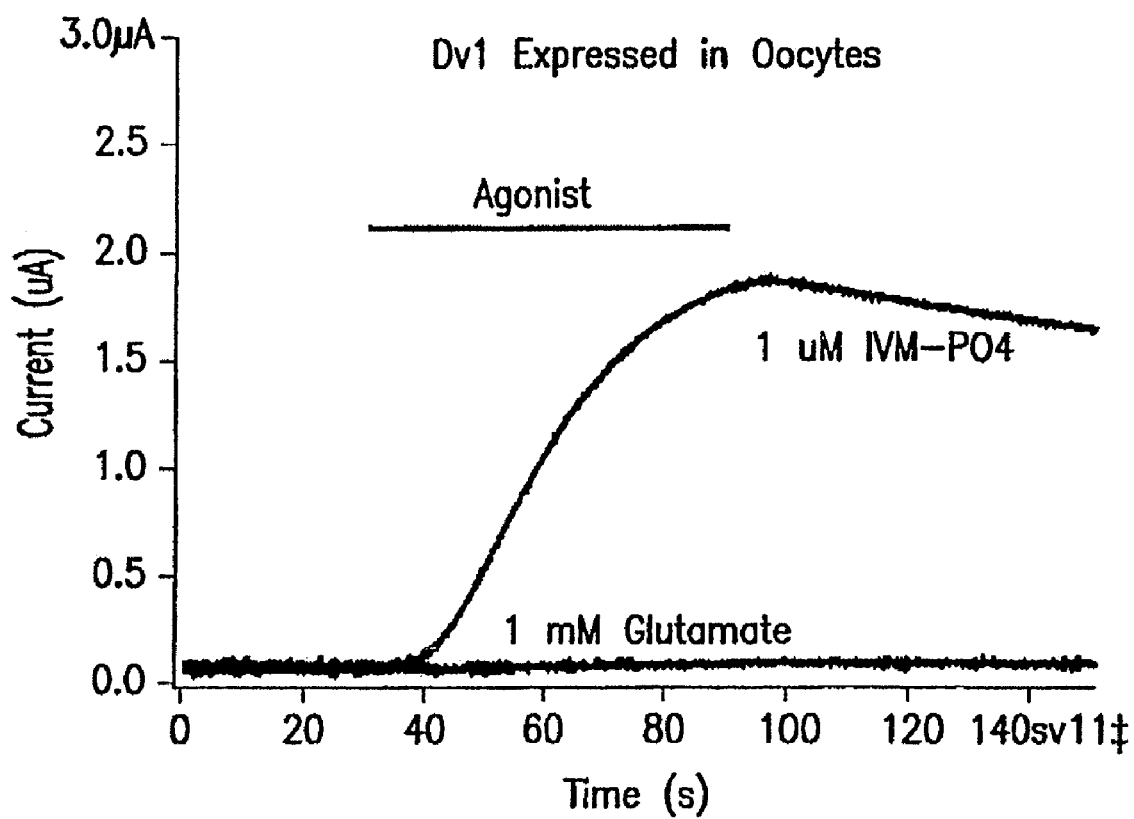
FIG. 9 shows current activation in *Xenopus* oocytes injected with DvLGIC/GluCl 1 mRNA. Current activation was maximal with 1 µM ivermectin-phosphate.

The present invention relates to an isolated nucleic acid molecule (polynucleotide) which encodes a *Dermacentor variabilis* invertebrate LGIC/GluCl channel protein. The isolated or purified nucleic acid molecules of the present invention are substantially free from other nucleic acids. For most cloning purposes, DNA is a preferred nucleic acid. As noted above, the DNA molecules disclosed herein may be transfected into a host cell of choice wherein the recombinant host cell provides a source for substantial levels of an expressed functional single, homomultimeric or heteromultimeric LGIC. Such functional ligand-gated ion channels may possibly respond to other known ligands which will in turn provide for additional screening targets to identify modulators of these channels, modulators which may act as effective insecticidal, mitacidal and/or nematocidal treatment for use in animal and human health and/or crop protection. It is shown herein that DvLGIC/GluCl 1, 11 and 7-1 expressed in *Xenopus* oocytes exhibit a current in response to the addition of ivermectin phosphate. In contrast, DvLGIC/GluCl 10-2 was not responsive to ivermectin phosphate or glutamate. However, it should be noted that the GABA-A subunit gamma does not express a functional homomultimer. Therefore, the expressed proteins of the present invention may function in vivo as a component of a wild type ligand-gated ion channel which contains a number of accessory and/or channel proteins, including the channel proteins disclosed herein. However, the LGIC proteins of the present invention need not directly mimic the wild type channel in order to be useful to the skilled artisan. Instead, the ability to form a functional, single, membrane associated channel within a recombinant host cell renders these proteins amenable to the screening methodology known in the art and described in part within this specification. Therefore, as noted within this specification, the disclosed Dv channel proteins of the present invention are useful as single functional channels, as a homomultimeric channel or as a heteromultimeric channel with various proteins disclosed herein with or without additional Dv channel subunit proteins or accessory proteins which may contribute to the full, functional LGIC channel.

The present invention relates to an isolated nucleic acid molecule (polynucleotide) which encodes mRNA which expresses a novel *Dermacentor variabilis* invertebrate LGIC/GluCl channel protein, this DNA molecule comprising the nucleotide sequence disclosed herein as SEQ ID NO:1, SEQ ID NO:3, SEQ ID NO:4, and SEQ ID NO:6.

The isolation and characterization of the DvLGIC/GluCl nucleic acid molecules of the present invention were identified as described in detail in Example Section 1. These cDNA molecules, as discussed herein, are especially useful to establish novel insecticide screens, validate potential lead compounds with insecticidal activity, especially for use in treating parasite infestations in human and animals, such as livestock, dogs and cats or that may kill other arachnids. These cDNAs, or portions thereof, are also useful as hybridization probes to isolate related genes from other organisms to establish additional pesticide drug screens. The DvLGIC/GluCl encoding cDNAs of the present invention were isolated from the American dog tick species *Dermacentor variabilis*. The DNA sequence predicts proteins that share common features with the class of chloride channels sensitive to glutamate and ivermectin. When the DvLGIC/GluCl cDNAs are expressed in *Xenopus* oocytes, a glutamate and/or ivermectin-sensitive channel is observed. The pharmacology of compounds that act at these channels would likely be different between these species. By screening on the arachnid channel it will be more likely to discover arachnid-specific compounds. Therefore, the cDNAs of the present invention can be expressed in cell lines or other expression systems and used for competition binding experiments or for functional chloride channel assays to screen for compounds that activate, block or modulate the channel.

Invertebrate glutamate-gated chloride channels (LGIC/GluCls) are related to the glycine- and GABA-gated chloride channels and are distinct from the excitatory glutamate receptors (e.g. NMDA or AMPA receptors). The first two members of the LGIC/GluCl family were identified in the nematode *C. elegans*, following a functional screen for the receptor of the anthelmintic drug ivermectin. Several additional LGIC/GluCls have now been cloned in other invertebrate species. However, there is no evidence yet for LGIC/GluCl counterparts in vertebrates; because of this, LGIC/GluCls are excellent targets for anthelmintics, insecticides, acaricides, etc. Specific LGIC/GluCl modulators, such as nodulisporic acid and its derivatives have an ideal safety profile because they lack mechanism-based toxicity in vertebrates. The present invention relates in part to four novel *D. variabilis* LGIC/GluCl clones. DvLGIC/GluCl 1, DvLGIC/GluCl 11 DvLGIC/GluCl 7-1 and DvLGIC/GluCl 10-2 were identified in the original screen. DvLGIC/GluCl 1, DvLGIC/GluCl 11, and DvLGIC/GluCl 7-1 were identified by both probes while DvLGIC/GluCl 10-2 was recognized only by RsLGIC/GluCl 2 probe.

The present invention relates to the isolated or purified DNA molecule described in FIG. 1 (DvLGIC/GluCl 1) and set forth as SEQ ID NO:1, which encodes the *D. variabilis* LGIC/GluCl protein described in FIG. 2 and set forth as SEQ ID NO:2, the nucleotide sequence of DvLGIC/GluCl 1 is as follows:

```
                                                            (SEQ ID NO: 1)
   1 GCGAGGCTGT CGGTGGAAAG CGCGGCGAGC ACGCGTCCGC GCGCCTGCGC

51 TCCAGTCCGG ACCCGAGCTG GAGCACGGCC TGGAGGGATA GGTCTGGTCG

101 ACCGTGGTTG CAGCTCCAGA CGCGCAGTTG GAGCTCGGCG AAGGGGCTGC

151 TGCTGCGAGC ACTGTGCGCA TGCCACTTTC AGCGCTGAAC GTGTGGCGCG

201 CTTGCGTCAC GTTGTCCCTC CTCAGGACGA CGCTCGCGCA GGAAAGGCGG

251 TCAAACGGAG CGCTGGATGA CCTGGAGAAG CTTGACGACT TATTAAGAAC

301 CTATGACCGG CGTGCCCTTC CCACGACACA CTTGGGAACG CCAACAAAAG

351 TGGCTTGCGA AATCTACATA CGCAGCTTCG GGTCCATAAA TCCAGCCACA

401 ATGGACTATG AGGTTGATCT TTATTTGCGG CAGACTTGGC AAGATGATCG

451 CTTGACGAGC CCCAACGTAT CCAGGCCCCT GGACCTCAAT GATGCAAAGC

501 TGGTGCAGCG TATATGGAAA CCGGAAGTAT TCTTCGCAAA TGCCAAACAC

551 GCAGAGTTCC AATATGTCAC AGTACCTAAT GTACTGGTCC GCGTTAACCC

601 GAACGGAAAG ATTCTATACA TGCTCAGGCT CAAGCTAAGG TTTGCATGTA

651 TGATGGATTT ATATCGCTTT CCTATGGACT CCCAAGTTTG CAGCATCGAA

701 CTCGCCTCAT TCTCGAAAAC AACCGAAGAA CTGCATCTGG AGTGGTCTGA

751 TACCAATCCG ATAATACTAT TCGAAGGCCT GAAGTTACCA CAATTCGAGA

801 TTCAGAATAT AAATACGTCA ATCTGCATGG AGAAATTTCA CATCGGAGAG

851 TACAGCTGCC TGAAGGCCGA CTTCCACTTG CAGCGGTCAC TGGGCTACCA

901 CATGGTGCAG TCGTATCTGC CTACAGTGCT CATCGTGGTC ATCTCGTGGG

951 TGTCCTTCTG GCTCGACGTT GAGTCCATTC CGGCGCGCAC CACACTGGGC

1001 GTCACGACGC TGCTCACTAT TTCTTCCAAG GGCTCCGGTA TACAGTCCAA

1051 CTTGCCTCCG GTCTCATACG TGAAGGCAAT CGATGTGTGG ATGGGAGCCT

1101 GCACGGGCTT CGTGTTCTCG GCACTACTGG AGTTCACCGT CGTCAGCTGC

1151 CTGGCCAGGA TGCAGGCACG AGACAAGGAG TCAAGTATGG TTACAACAAA
```

-continued
```
1201 GCACGGAGTG GCGATTGTCA ACGCTGTTCC TGATAACCAG GCGTCGGTTC

1251 CTTGCACTGT CCGGGCGAAA ACTATTGACC AGGTCTGCCG CGTAGCGTTT

1301 CCGGCCATCT TCCTCGTGTT AACGCCATT TACTGGCCGT ATTTTATGTG

1351 CTTTACAGAG TAGAACATCA CCGAACAACG CAAAAGTTCT GCGGAAAAAG

1401 TGTCCGTATA ACGTGTCTTG AGGCTCATTG TCACGTATTT ACACCGGCAT

1451 GAAAGGTTCG TTAAATCAAC CAATATAGCG TCCTCAGCCA ATTACGCACA

1501 CTAGTTTAGA GCAGCCAGTC GCATTTCCTT TACTACTATC GAGAGAGGTT

1551 GGACTAAGTC ATGAGTTCAT TCCCTTCGGT AGCTTCTGTC AATTGTCTCA

1601 GGGAAGGATA GGTTGGTGCT TCGAGCTCTT TAGCGCATGC AAACTCTGTT

1651 GGGATGCTTA GGTACGCGCA GGGAACGTGA CGATCTATAA TGTTTTTTGG

1701 AGTAGTAATG GAACACGGCA CTGACGGTCG ATAAATTTGA TAGCATGAGG

1751 AAGTGAACTA ATTACTATAA AATGCACAAC GGCTTTATTG TGGAGTATTG

1801 CGCGTTTTCT TTTTATAATG TAGGAGGGAT AGAATATAAG TGCCAAGAAG

1851 CAGATACCTA AAATCGTAAA ACAGCGCCGC CATGTAGATG TCTGATTTAG

1901 AAGATACCGT TGCACTGCAT CACAGGCGTA GCATACAACA AATTTAAGCT

1951 CTTCTATAGG AAATAGAAAT ATTGAGTATT ACTTCGTTAA TGCGGGAATC

2001 GTATTTGTTA AATGTATCTT TCGATTAACA ATTGGGACTT TCGCTGTTTC

2051 AATACAGACT TTGTTGAGCC TTCGTATAAC ATTACGAAAA AAAAGAAAA

2101 TCTGAAAAGA ATAATATCTA CGTTTTCAAT ACCAGCCATT CTAGTCCAGA

2151 AGGCAAGCGT GCTGCAAAAT CCGAAAGCAA AATTTATTTA TGTTAAATAT

2201 AACATCCCGG TCATTTGCCC TAACTTTGTG GCGACAATTG ACAGCGTCAA

2251 CTAAACTGCG TATTCCATGT TGTCGCTTAA TGGCTTTGCC ATGATGCCAT

2301 CTTAGTCATT TTCAGCTGTT CAAAGTTTTA AGGAATAAGC TATGCTTAAG

2351 CTACAATTGA TTGTTAATGA AGTGTCAGCG CGAAGACTTG CGAGTTTGAT

2401 TTCGTACATA TGAGTGTTCT TTATACACCC TGACACTACC TTTTTGGAGG

2451 CGATGAGCCG AGAATTCAGA AAACGTCATG GCCAGTTTTA ACAGAACAGT

2501 GACCCTGTTA AAAATGTCTG TATGAATACT GTTGTTATTT ATGGTAGTTT

2551 TGAAATCGTT AATATATGT TATGTTACGT GATCAAGTGT CAATGGCTAT

2601 ACATTATGGA CCTCCCATTA ACTTGATCAA TCCAATCGTC CAGACATTTA

2651 ATGTCCGAGG AACTTCAGGT TTATTAACTG TAGGTTAAAA CTCTGATGTA

2701 TATATAACAG CATGGAATGC AAGATCTCGT CATATTTCAT GCAATTTCAC

2751 TAGATGCAGC GATGTTTTCG ATGGAGATTA TTCGTCTCCT GAAAAAAAA

2801 ATTGACATTC ACCGGCATGT AGGCTGAAGC TATGAAGAAA ACCCAGCTGG

2851 GTTTCCTTTG TAGCTTCGTT TTTTTCCTAG ATAAGGTTAA TATCTTGATC

2901 TCTGTGCTAC AGTAAGAGTG AAACTGAACT CGGCCTGAAA AACTTGCGTT

2951 TTCTTATCGC ACTACCGTCA TTGAAACGCT CAGTACTAGG TCTTGGTGAA

3001 ACACATGACT AAAATTTGAA AGCTTTAGAA TGAATTTATT TATTTTTATT

3051 TATTTACAAA TACTGCAATC CCGTTACGGG ATTGCAGTAT TTGCATTATG

3101 AAAGAAACAC ATTATGAAAG AAACGAGAAA CGCAATCTTC GCATTATGAA

3151 AGAAACGAGC AGAAGACAGA TGGCTAATTT TATTTGCTGA TTGTAGCCCA

3201 TTTTCCTCTT ACTAGAGAGT TATGGGTGAC AGCAGAATTC TCAGAATAGT
```

-continued

```
3251 GCATTCTCTT AAAATAACTT GACATCGTGT GGTAATTTCC CTAAATCTCA

3301 TGTAGGTAGA TGCTTTATTT ATGTAATTTG AGGAGACATA CCCATGAAAA

3351 CGAAAAGATG ACGGGCGCTA ATGGTTATAG AAGTCCTTCC TGCCACTGTT

3401 GGCTGAAATG TATTTGTATG TTTTTTGGTC AGTCACTGTG TCCCAAAGCT

3451 TCTTCGTGCT GAAGCTTAAG TGAGTCTATG CTGTTCAACA CCATTGTATA

3501 TTTTTGTAAT AAAATAGTTT ATTAAATGAC CTGGTTCTAC TTGAAAAAAA

3551 AAAAAAAAAA AAAAAAAAAA AAAAAAAAAA AAAAAAAAA AAAAAAA.
```

The present invention also relates to the isolated or purified DNA molecule described in FIG. 3 (DvLGIC/GluCl 11) and set forth as SEQ ID NO:3, which encodes the *D. variabilis* LGIC/GluCl protein described in FIG. 2 and set forth as SEQ ID NO:2, the nucleotide sequence of DvLGIC/GluCl is as follows:

```
                                                    (SEQ ID NO: 3)
   1 CGAAGGGGCT GCTGCTGCGA GCACTGTGCG CATGCCACTT TCAGCGCTGA

51 ACGTGTGGCG CGCTTGCGTC ACGTTGTCCC TCCTCAGGAC GACGCTCGCG

101 CAGGAAAGGC GGTCAAACGG AGCGCTGGAT GACCTGGAGA AGCTTGACGA

151 CTTATTAAGA ACCTATGACC GGCGTGCCCT TCCCACGACA CACTTGGGAA

201 CGCCAACAAA AGTGGCTTGC GAAATCTACA TACGCAGCTT CGGGTCCATA

251 AATCCAGCCA CAATGGACTA TGAGGTTGAT CTTTATTTGC GGCAGACTTG

301 GCAAGATGAT CGCTTGACGA GCCCCAACGT ATCCAGGCCC CTGGACCTCA

351 ATGATCCAAA GCTGGTGCAG CGTATATGGA AACCAGAAGT ATTCTTCGCA

401 AATGCAAAAC ACGCAGAGTT CCAATATGTC ACAGTACCTA ATGTACTGGT

451 CCGCGTTAAC CCGAACGGAA AGATTCTATA CATGCTCAGG CTCAAGCTAA

501 GGTTTGCATG TATGATGGAT CTATATCGCT TTCCTATGGA CTCCCAAGTT

551 TGCAGCATCG AACTCGCCTC ATTCTCGAAA ACAACCGAAG AACTGCATCT

601 GGAGTGGTCC GATACCAATC CGATAATACT ATTCGAAGGC CTGAAGTTAC

651 CACAGTTCGA GATTCAGAAT ATAAATACGT CAATCTGCAT GGAGAAATTT

701 CACATCGGAG AGTACAGCTG CCTGAAGGCC GACTTCCACT TGCAGCGGTC

751 ACTGGGCTAC CACATGGTGC AGTCGTATCT GCCTACAGTG CTCATCGTGG

801 TCATCTCGTG GGTGTCCTTC TGGCTCGACG TTGAGTCCAT TCCGGCGCGC

851 ACCACACTGG GCGTCACGAC GCTGCTCACT ATTTCTTCCA AGGGCTCCGG

901 TATACAGTCC AACTTGCCTC CGGTCTCATA CGTGAAGGCA ATCGATGTGT

951 GGATGGGAGC CTGCACGGGC TTCGTGTTCT CGGCACTACT GGAGTTCACC

1001 GTCGTCAGCT GCCTGGCCAG GATGCAGGCA CGAGACAAGG AGTCAAGCAT

1051 GGTTACAACA AAGCACGGAG TGGCGATTGT CAACGCTGTT CCTGATAACC

1101 AAGCGTCGGT TCCTTGCACT GTCCGGGCGA AAACTATTGA CCAGGTCTGC

1151 CGCGTAGCGT TTCCGGCCAT CTTCCTCGTG TTTAACGCCA TTTACTGGCC

1201 GTACTTTATG TGCTTTACTG AGTAGAACAT CACCGAACAA GGCAATAGTT

1251 CTGCGGAAAA AGTGTCCGTA TAACGTGTCT TGAGGCTCAT TGTCACGTAT

1301 TTACACCGGC ATGAAAGGTA GGTCAAGGGA GCGTTCGTTA AATCAACCAA

1351 TATAGCGTCC TCAGCCAATT ACGCACACTA GTTTAGAGCA GCCAGTCGAA

1401 TTTCCTTTAC TACTATOGAG AGAGGTTGGA CTAAGTCATG AGTTCATTCC
```

-continued

```
1451 CTTCGGTAGC TTCTGTCAAT TGTCTCAGGG AAGGATAGGT TGGTGCTTCG

1501 AGCTCTTTAG CGCATGCAAA CTCTGTTGGG ATGCTTAGGT ACGCGCAGGG

1551 AACGTGACGA TCTATAATGT TTTTTGGAGT AGTAATGGAA CACGGCACTG

1601 ACGGTCGATA AATTTGATGG TATGAGGAAG TGCACTGATT ACTATAAAAT

1651 GCACAACGGC TTTATTGTGG AGTATGGCTC GTTTTCTTTT TATAATGTAG

1701 GAGGGATAGA ATATAAGTGC CAAGAAGCAG ATACTTAAAA TCCTAAAACA

1751 GCGCCGCCAT GTAGATGTCT GATTTAGAAG ATACCGTTGC ACTGCATCAC

1801 AAGCGTAGCA TACAACAAAT TTAAGCTCTT CTATAGGAAA TAGAAATATT

1851 GAGTATTACT TCGTTAATGC GGGAATCGTA TTTGTTAAAT GTATCTTTCG

1901 ATTAACAATT GGGACTTTCG CTGTTTCAAT ACAGACTTTT TTGAGCCTTC

1951 GTATAACATT ACGAAAAAAA AAGAAAATCT GAAAGAATA ATATCTACGT

2001 TTTCAATACC AGCCATTCTA GTCCAGAAGG CAAGCGTGCT GCAAAATCCG

2051 AAAGCAAAAT TTATTTATGT TAAATATAAC ATCCCGGTCA TTTGCCCTAA

2101 CTTTGTGGCG ACAATTGACA GCGTCAACTA AACTGCGTAT TCCATGTTGT

2151 CGCTTAATGG CTTTGCCATG ATGCCATCTT AGTCATTTTC AGCTGTTCAA

2201 AGTTTTAAGG AATAAGCTAT GCTTAAGCTA CAATTGATTG TTAATGAAGT

2251 GTCAGCGCGA AGACTTGCGA GTTTGATTTC GTACATATGA GTGTTCTTTA

2301 TACAACCTGA CACTACCTTT TTGGAGGCGA TGAGCCGAGA ATTCAGAAAA

2351 CGTCATGGCC AGTTTTAACA GAACAGTGAC CCTGTTAAAA TGTCTGTATA

2401 AATACTGTTG TTATTTATGG TAGTTTTGAA ATCGTTTAAT ATATGTTATG

2451 TTACGTGATC AAGTGTCAAT GGCTATACAT TATCGACCTC CCATTAACTT

2501 GATCAATCCA ATCGTCCAGA CATTTAATGT CCGAGGAACT TCAGGTTTAT

2551 TAACTGTAGG TTAAAACTCT GATGTATATA TAACAGCATG GAATGCAAGA

2601 TCTCGTCATA TTTCATGCAA TTTCACTAGA TGCAGCGATG TTTTCGATGG

2651 AGATTATTCG TCTCCTGAAA AAAAAAATTG ACATTCACCG GCATGTAGGC

2701 TGAAGCTATG AAGGAAACCC AGCTGGGTTT CCTTTGTAGC TTCGTTTTTT

2751 TCCTAGATAA GGTTAATATC TTGATCTCTG TGCTACAGTA AGAGTGAAAC

2801 TGAACTAGGC CTGAAAAACT TGCGTTTTCT TATCGCACTA CCTTCATTGA

2851 AACGCTCAGT ACTAGGTCTT GGTGAAACAC ATGACTAAAA TTTGAAAGCT

2901 TTAGAATGAA TTTATTTATT TTTATTTATT TACAAATACT GCAATCCCGT

2951 TACGGGATTG CAGTATTTGC ATTATGAAAG AAACACATTA TGAAAGAAAC

3001 GAGAAACGCA ATCTTCGCAT TATGAAAGAA ACGAGCAGAA GACAGATGGC

3051 TAATTTTATT TGCTGATTGT AGCCCATTTT TCTCTTACTA GAGAGTTATG

3101 GGTGACAGCA GAATTCTCAG AATAGTGCAT TCTCTTAAAA TAACTTGACA

3151 TCGTGTGGTA ATTTCCCTAA ATCTCATGTA GGTAGCTGCT TTATTTATGT

3201 AATTTGAGGA GACATACCCA TGAAAACGAA AGACGACGG GCGCTAATGA

3251 TTATAGAAGT CCTTCCTGCC ACTGTTGGCT GAAATGTATT TGTATGTTTT

3301 TTGGTCAGTC ACTGTGTCCC AAAGCTTCTT CGTGCTGAAG CTTAAGTGAG

3351 TCTATGCTGT TCAACACCAT TGTATATTTT TGTAATAAAA TAGTTTATTA

3401 AATGACCTGG TTCTACTTGA AAAAAAAAAA AAAAAAAAA AA
```

The present invention also relates to the isolated or purified DNA molecule described in FIG. 4 (DvLGIC/GluCl 7-1) and set forth as SEQ ID NO:4, which encodes the *D. variabilis* LGIC/GluCl protein described in FIG. 5 and set forth as SEQ ID NO:5, the nucleotide sequence of DvLGIC/GluCl 7-1 is as follows:

```
                                                    (SEQ ID NO: 4)
   1 CTCGGTCGCG CGCGCACACA GCAAGTGCTC CGGTGAGGCG GCTGATATGA
  51 TCCCGGCGTC CGTGGCTCTC GGCCGAAGGA TGTGCTCTCT GCTGCTCGCT
 101 GTCGGATGCG CCACGACTAG CGCCTGGTTC GCTCAGGCTG TCGACCACAT
 151 CGACAAAGGA TACCCAGCAC CAGGACTCTT CGATGATGTC GACCTTCAAA
 201 TATTGGACAA CATCTTATGG AGCTACGACC GACGCATCAC CCCTGGTCAT
 251 CATTTAAACG TTCCTACAGT TGTTAAGTGC GAGATATATC TCAGGAGTTT
 301 TGGAGCTGTG AACCCTGCAA CAATGGACTA CGACGTAGAC CTGTACCTGC
 351 GTCAGACGTG GACGGACTTG CGGATGAAGA ACGCCAACCT GACCCGGTCC
 401 CTAGACTTAA ACGACCCCAA CCTCCTCAAG AAAGTGTGGA AACCTGACGT
 451 CTACTTTCCC AATGCCAAGC ACGGGGAGTT CCAGTTCGTC ACTGTTCCCA
 501 ACGTTCTCTT GAGGATATAC CCTACCGGCG ATATACTCTA CATGTTAAGG
 551 CTAAAGCTAA CATTCTCCTG CATGATGAAC ATGGAGCGGT ACCCCCTGGA
 601 CCGACAGGTC TGCAGCATCG AGCTTGCCTC ATTTTCCAAG ACGACAAAGG
 651 AGGTTGAGCT CCAATGGGGA AACGCTGAGG CTGTCACCAT GTACAGTGGT
 701 CTGAAGATGG CACAATTCGA GCTTCAACAA ATCAGCCTGA CGAAGTGCAG
 751 CGGCGCCTTT CAGATAGGOG AGTACAGCTG CCTGCGCGCG GAGCTCAACT
 801 TGAAGCGTTC CATTGGCCAC CACCTAGTGC AGTCTTACCT GCCGTCCACA
 851 CTCATCGTGG TCGTGTCGTG GGTGTCCTTC TGGCTCGACG TGGACGCCAT
 901 ACCGGCGCGC ATCACGCTGG GTGTCACCAC GOTOCTOACT ATTTCGTCGG
 951 AGAGCTCCGA CCACCAGGCC AACCTAGCGC CGGTGTCGTA CGTGAAAGCG
1001 CTCGACGTGT GGATGGGCAC GTGCACCATG TTCGTGTTCG CCGCGGTGCT
1051 CGAGTTCACC TTCGTCTCCT ACCTCGCTCG CAGAAAGCAG ATCGTGCCCG
1101 CCTCTATCGC GGACGTCGAG GCTTCCCAAG ATCTCGTTCT TGTCGTGGGA
1151 AACAAGGACA AAAATCGACC CCCGTCACCG TCCATCCCGA CGTCCACCCA
1201 CGTGGTCTTG GCTTACAGAC ACCGTGCCAA GCAGATCGAC CAAGTGAGCC
1251 GGGTCGCTTT CCCAATCGGC TTTGTTCTCT TCAACGCACT CTACTGGCCC
1301 TATTACTTGC TCTAGTTGGC CATGGTCTCA GTGCCTACAG CTGCTGCTCC
1351 CAACGTGCAG CCATACGCCG GGAAACGGGT GGCTGCGTAC CCCAGGGAAA
1401 CGGTCGGCCG CTGGATTGAA AAGGACTGCC ATCACCGACG CACGCTCTGG
1451 TGGAAGAGAA AGCTACACTC TTTGCTCTGC CGCATTCATT CTTTTCTTAC
1501 CGTGATCCTC TTTGTCTCTT ATCTTTTCTT TTGTGTGTGT GTAGCCGTTG
1551 GCGCTGTCTT CAGGGCATTC CGCTCTTAAG CGGGTGCTGA CACATTGACC
1601 ATCGCTTCAG ACTTCCTCGT TGTACGGATG TTGCCATCAT AATCCCAAAG
1651 AGCATCATGG TTAAAACTGT CCATACGCAC ATTTGTAAAT AAGAATTGAT
1701 TCACACATCA GAAACATGGT TGTACTTAGG GGTGCCCAAA AATATTTTTG
1751 CCCTTTTTTG AATAATGTAT GAAAGACAAC TTAACTTTCA CCAAAATAAA
1801 CTAGAAAGCT CAGCGTGTTT GTCTTTATTC GCTGCTACAC TAACTTCGAG
1851 ACCAACGGAT AAGAAAGTTA ACGGAATAAG AGAGCGGTAC CTTTATTACC
```

-continued

```
1901 TCTCTTTAAA AGAAGTTAGC AGCGATGAAT TTGTTGCTCT TTTCTCTAAG

1951 GCATTCAATA ATTTATAAGG CGTCGGGTAT TTCAGTTACT CAATTATTCA

2001 ATGAAACAAT GTATCCTACA TGACGAGTAC TGGTCAGTCG AGATGCGTTG

2051 TTTTCCCGAC AGTTCTCATT CAGGGTTCTT TCCGAGCGAA GACTGATTGC

2101 GTGCTGCCAG ACTGATTCGT TCTTGGCGAT TTGGTCGAAA CGTTTGCGCT

2151 TCCTCATTCA GCGTCCGGCG TCAGCAATAT TTGCGCGTAA TCCC.
```

The present invention also relates to an isolated or purified DNA molecule described in FIG. 6 (DvLGIC/GluCl 10-2) and set forth as SEQ ID NO:6, which encodes the *D. variabilis* LGIC/GluCl protein described in FIG. 7 and set forth as SEQ ID NO:7, the nucleotide sequence of DvLGIC/GluCl 10-2 is as follows:

```
                                                    (SEQ ID NO: 6)
   1 CGGACCGGTC GGCCCACTTT CTCCTTTCAT GACGCGCCGT GATCACGCGG

51 CGTGACACCC AGCGTCGCCT CTACGTTTCA TTCATTTCGT GTCTCCGCCT

101 GCGGTGCGCC TGCCGCGTGA CGCAACCGGG CGCATGACAC CGCCGAACCC

151 TCTGTCGTCG GOGOATOGOG TCCTGGCGCT GCTCCTGCTG GTGACAGTGC

201 CGGCTTCTCT GGGGCAGAGG AGACATGGAA CTGTCGGCGA TTTGGACAAG

251 TTGGACAAAC TCCTGAGCAA ATATGACAGA AGGGCGTTGC CAACGGGGCA

301 CATGAGATTA CGAAGTGGAC CTCTACCTGC GACAACGATG GCATGATGAC

351 CGCTTTGAGA TGAGCGGCAT TAGTGGACCC CTCGACCTGA ACGATCCCAA

401 ACTGGTGCAA CGTATATGGA AACCCGAAGT CTTTTTTGCC AACGCAAAGC

451 ATGCGGAGTT CCAGTACGTG ACGGTGCCCA ACGTCCTAGT ACGCATCAGT

501 CCTACGGGGG ACATTCTCTA CATGCTCAGG TTGAAGCTGA CTTTTTCTTG

551 CATGATGGAC CTTTACCGGT ACCCCCTAGA CGCTCAAGTT TGCAGCATTG

601 AACTCGCTTC GTTCTCGAAG ACGACGGACG AGCTACAGCT GCACTGGTCT

651 AAGGCATCGC CTGTGATCCT CTATGAAAAC ATGAAGCTCC CACAATTTGA

701 AATTCAAAAC GTGAACACGT CCCTGTGCAA TGAGACATTC CACATTGGAG

751 AGTACAGCTG CCTGAAAGCC GAGTTCAACC TACAGCGCTC TATTGGCTAC

801 CACCTCGTCC AATCGTATCT GCCCACCATC TTGATCGTGG TCATCTCTTG

851 GGTCTCCTTC TGGCTCGACG TGGAAGCGAT TCCAGCCCGA ATTACATTGG

901 GAGTCACCAC GCTTCTTACC ATCTCATCCA AGGGTGCCGG TATACAAGGA

951 AACCTGCCGC CCGTCTCGTA CGTCAAGGCA ATCGACGTCT GGATGGGCGC

1001 CTGCACCATG TTCGTGTTTG CCGCACTGCT TGAGTTCACC TTTGTCAACT

1051 ACCTGTGGAG GAAGCGGCCC GCGACTGCCA AGTCACCACC TCCGGTGGTC

1101 GCAGCCATTC CCGAGAGCAA AGTGGCTGTG CTCCTCCCAT GCAACGGAAA

1151 CTTGGGGCCA TGCAGCCCCA TCACTGGCGG TACAGACATC AGCCCTTCGC

1201 CCACAGGTCC TGAAGCTGTC AGAAACAGAC ACAAGGTTCA GGCCAAGAGA

1251 ATTGACCAGA CCTGCAGGAT AGCATTTCCC ATGGCTTTCC TGGCGTTTAG

1301 CGTCGCATAC TGGCCATACT ATCTTTTGTG AGGCCGCGGT ACCCCGAGCT

1351 AATGTCAGGA ACGGAGAGGC GGGTACCACG AAGTCGGGGG GGGGGGGAG

1401 GGGGGAGAGT GCTTGTGGCT ATCACAATCC CGTTGGTTCT CTGTAAGAAC

1451 GCTTTTGTTT TGCACAGAAG CTCACTGCAT CACATTTTGC GTCTCCCTAG
```

-continued
```
1501 TGTTTAATTA TTTGTTTCTG CACTTGTGTT CCCGTGTGCA TTCTGACTGA

1551 ATATOACTOC AACCCTTCAG TGTGTATAAG TCCCAAAGTG AATTGGATAT

1601 TTCCTCTTCG CGATCCTCTT GAGGGCACCT CTAGTCACTA ATCTAACACG

1651 TAGGAGAGTT TAAGGATGCG TTAGGCAGCA CTTTTCTTGT GCTTTAAGTG

1701 GATCTCATCA TATTCTGGTA GAGAATATAA ACTTCAACAC TGAAGTAGTA

1751 TTTACAAGGC AGACTAACAT GTTGCTAGAA ACAGTATTTT TGCAGGAGGG

1801 AAGATGCAAT GATTATACAG GGTGTTCAAA ATTAAGCTTT ATGGTTTTAT

1851 AGGAATTAGG CACTGCGAGG GGAAGGGCAA CCGTTATCGT CTTTGTCTAT

1901 GCCTCCGCCC TATTGTCAGA CTAAATGCCG CACACAACAG CCTCGTCACA

1951 TCAGGGAAGA TCTTTGTGCC AATCCTCACT CTCTTGCGTG CGTAATCACG

2001 TAAACGACAA TTAAAATTTG GAGCCAGCTA TCTCGAAGCA AAGATATGCT

2051 GGAAGAATTC TTCTAAGTGT AACTGTGTAG AAACTTTTCA ATACACAAAT

2101 ACACACTTAC TGCAGTCAAT AAAAAGTTAA TTACTCGATT TTATTTAATT

2151 GGGCTGCTGA CAGCAATAAC TCTCATCTCA CTTTGTGTCC CCCTGGCCAC

2201 ATAACTTATT TGCACAGGTG GTCTTCGCGT GCATCCCAGT GGCTAAATTT

2251 AAGAAAACCA TAAAGCTTAA TTTTGAACAC CTGGTATATC ATGATGCTTT

2301 CAATGCTTTA TTGTTGTATT ATAAAAAAAG ATATACTATC AACGACTCAG

2351 GCCGGAGAAT CATGTTGGAA AAAAAATGTT TCATTGTTTC CTTTCGTCAT

2401 CGCGCCCTTA GGTTAATTTG CCCTGTACAG TTCCTGAGGG AACGCATTAG

2451 TGCACAAAAA AAGTATTTCG GCTTCCACAT CGCAACGAAA ACGGGCGTCG

2501 CCTCCTGTCT CTACAAGACA ATGAGATGCG CAGGCCGCAC GCTTTTTCGG

2551 GGTCCGCAAT TATTAAACAT GGCGTATATT TTGATAACCC GCACCTTCTT

2601 CCTACGCAGC ATTTTTCTGT TAGACCCACT GGGTTCATTT AACCAATCCT

2651 AGGCCTAAAA CCGTATTCAA GCCCAGCACA AAGTCCGCTT TTGCGAACTC

2701 CCGTTCAGAT GTGGATGAGC CGTTGGCTTA CAGGACTCTG ACCTAAGTAT

2751 GGGCCTGTGT CAAACGGCGT CAGAAAGATG AGCACAACAG CCCCTTATTG

2801 CGTAACGCTG CCGGCAATGC TCGCCATTTT AAGCTGTCCC GAACTGCGAA

2851 ATTATTCCAC GGTAGCGCTT TTGTAGATGT GGAAGACTTG CCTAATCACT

2901 TCAAGGTGT CGCCACTTAC AATACTATAC GTACAGTTCG GCCTGGAGAA

2951 TTTGGCGCAC GCATACTTGT AGTACCATGA GGCGGAGTTA TTACTTCGGG

3001 AGGAATTGCG CAGGCAGCTA ATCCCCATCT ACGCAACTCT GGACAGTCGG

3051 ATGTTATGCA TGGTAGGAGA ATGGACTATA GAAGGGTGGA GTCTGCAAGT

3101 CAGGCGAGGA TACAGCGGCG TAGCGAAAAC GTAGCCATGC TTGTGGAGTA

3151 CACGACCCGA CTCTTGTGAA ACACGGATCC ATCTATGTCG GAAACAAAAA

3201 TTTAAGCACT TCATGCGCGC AGTAAAGAAA GAACCCTTTG GGGGCCTGAT

3251 ACCAAACTTG CCCAAGAACC TCCCAGAGTA CCTCGCAGAG GCCATGTCAA

3301 AGGAAAAGAC GATCTAGCAG TAGGATCCTG ATTTGGCTTT GGACAACGTC

3351 GCTGTAATGC GAGTGCTTAT AAAGTTCTTT GTTCTGGAAG AGGTTAAATG

3401 CTCCATCTAA CTCCAGGCTC TGTACTGCGG ACTTCGCCGG CTGAGGTCGT

3451 TCGTTAGAAG ATGGGCGTG CTGCCCGAAC CTCAGAATAT TCGGAGCGC

3501 CACTGTACGA GGTGCGGCAG CTGGCACTTT GAATCACCTA TGCGGAAGCT
```

```
3551 GCGCGAGGTT CTCCACACTA GGACTCCCAC AATGTGCGCG CCCTTGAACA

3601 AGCGATTGCC AACTTCAGAG CCCGCGGCGA CCAATCAAAG CTGAAGTATG

3651 TCATCGCAAA ACTTATATTT ATCGAACCTC AATTGGAAAG ACCATGTATT

3701 TTCACTGCGC TGTGGAACAT GAAATTTATG CGTTACATAT TCGCTCCGGG

3751 GAATAGCAAA AATATTGCAA AAATATTGGT GACACAGAAA GCAGTCGCAT

3801 ATCAAGCCCA TTATATGCGT TGACGCTGTA GTTTGTAAAG GGCACTTGAA

3851 TGTGGACGCC TGTTTAGAAT CGCGGAGAGA TTTCATTTTC GCGGAGCTTA

3901 TACCACTCTC AAATGTGCTG GGGCACGGCA GAATCGTGGA TCCAGTTTTT

3951 TTAACTTCCG TCAAAACAGA TTAGCAGTAG TTCACAGCGG CGAAACACTC

4001 ACAAGTGTAG TTATAAAAAC CTAACAGTTT GAATCAATAA ATATTTGACA

4051 TCAAAAAAAA AAAAAAAAA AAAAAAA.
```

The above-exemplified isolated DNA molecules, shown in FIGS. 1, 3 4, and 6, respectively, comprise the following characteristics:

DvLGIC/GluCl 1 (SEQ ID NO:1):
3598 nuc.: initiating Met (nuc. 170-172) and "TAG" term. codon (nuc. 1361-1363), the open reading frame resulting in an expressed protein of 397 amino acids, as set forth in SEQ ID NO:2.

DvLGIC/GluCl 11 (SEQ ID NO:3):
3442 nuc.: initiating Met (nuc. 32-34) and "TAG" term. codon (nuc. 1223-1225), the open reading frame resulting in an expressed protein of 397 amino acids, as set forth in SEQ ID NO:4. The DvLGIC/GluCl 11 protein, as with DvLGIC/GluCl 1, comprises the amino acid sequence as set forth in SEQ ID NO:2. The nucleotide sequences within the open reading frame of SEQ ID NO:3 and SEQ ID NO:1 show 9 nucleotide substitutions. Three of the substitutions are A-G changes possibly resulting from RNA editing events, while the remainder of changes most likely are a result of allelic differences within the tick population.

DvLGIC/GluCl 7-1 (SEQ ID NO:4):
2194 nuc.: initiating Met (nuc. 47-49) and "TGA" term. codon (nuc. 1313-1315), the open reading frame resulting in an expressed protein of 422 amino acids, as set forth in SEQ ID NO:5.

DvLGIC/GluCl 10-2 (SEQ ID NO:6):
4177 nuc.: initiating Met (nuc. 360-362) and "TGA" term. codon (nuc. 1329-1331), the open reading frame resulting in an expressed protein of 323 amino acids, as set forth in SEQ ID NO:7.

The percent identity at the nucleotide level for various exemplified cDNA molecules of the present invention were generated using the GCG-Best fit-Smith and Waterman algorithm. Comparative percent identities are shown below:

Drosophila LGIC/GluClα1 (U.S. Pat. No. 5,693,492) and DvLGIC/GluCl 1-54.869%;
Drosophila GluClα1 and DvLGIC/GluCl 7-1-58.029%;
Drosophila GluClα1 and DvLGIC/GluCl 10-2-54.938%;
DvLGIC/GluCl 1 and DvLGIC/GluCl 7-1-66.555%;
DvLGIC/GluCl 1 and DvLGIC/GluCl 10-2-75.000%;
DvLGIC/GluCl 1 and DvLGIC/GluCl 11-99.246%; and,
DvLGIC/GluCl 7-1 and DvLGIC/GluCl 10-2-69.103%.

To this end, the present invention relates a purified nucleic acid molecule encoding a *D. variabilis* LGIC/GluCl channel protein where the nucleic acid molecule comprises (a) a nucleic acid molecule which encodes an amino acid sequence selected from the group consisting of SEQ ID NOs 2, 5 and 7; or, (b) a nucleic acid molecule which hybridizes under conditions of moderate stringency to the complement of a second nucleic acid molecule which encodes SEQ ID NOs 2, 5 and 7; or, (c) a nucleic acid molecule which hybridizes under conditions of moderate to high stringency to the complement of a second nucleic acid molecule as set forth in SEQ ID NOs 1, 3, 4 and 6 and this nucleic acid molecule has at least about a 65% identity at the nucleotide level within the open reading frame to at least one of the second nucleic acid molecules as set forth in SEQ ID NOs 1, 3, 4 and 6.

The present invention also relates to biologically active fragments or mutants of SEQ ID NOs: 1, 3, 4 and 6 which encodes mRNA expressing a novel *Dermacentor variabilis* invertebrate LGIC/GluCl channel protein, respectively. Any such biologically active fragment and/or mutant will encode either a protein or protein fragment which at least substantially mimics the pharmacological properties of a *D. variabilis* LGIC/GluCl channel protein, including but not limited to the *D. variabilis* LGIC/GluCl channel proteins as set forth in SEQ ID NO:2, SEQ ID NO:5, and SEQ ID NO:7. Any such polynucleotide includes but is not necessarily limited to nucleotide substitutions, deletions, additions, amino-terminal truncations and carboxy-terminal truncations such that these mutations encode mRNA which express a functional *D. variabilis* LGIC/GluCl channel in a eukaryotic cell, such as *Xenopus* oocytes, so as to be useful for screening for agonists and/or antagonists of *D. variabilis* LGIC/GluCl activity.

A preferred aspect of this portion of the present invention is disclosed in FIG. 1 (SEQ ID NO:1; designated DvLGIC/GluCl 1), FIG. 3 (SEQ ID NO:3; designated DvLGIC/GluCl 11), FIG. 4 (SEQ ID NO:4; designated DvLGIC/GluCl 7-1) and FIG. 6 (SEQ ID NO:6, designated DvLGIC/GluCl 10-2) encoding a novel *Dermacentor variabilis* LGIC/GluCl protein. The present invention also relates to isolated nucleic acid molecules which are fusion constructions expressing fusion proteins useful in assays to identify compounds which modulate wild-type DvLGIC/GluCl activity, as well as generating antibodies against DvLGIC/GluCl. One aspect of this portion of the invention includes, but is not limited to, glutathione S-transferase (GST)-DvLGIC/GluCl fusion constructs.

Recombinant GST-DvLGIC/GluCl fusion proteins may be expressed in various expression systems, including

*Spodoptera frugiperda* (Sf21) insect cells (Invitrogen) using a baculovirus expression vector (pAcG2T, Pharmingen). Another aspect involves DvLGIC/GluCl fusion constructs linked to various markers, including but not limited to GFP (Green fluorescent protein), the MYC epitope, and GST. Again, any such fusion constructs may be expressed in the cell line of interest and used to screen for modulators of one or more of the DvLGIC/GluCl proteins disclosed herein.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The degeneracy of the genetic code is such that, for all but two amino acids, more than a single codon encodes a particular amino acid. This allows for the construction of synthetic DNA that encodes the DvLGIC/GluCl protein where the nucleotide sequence of the synthetic DNA differs significantly from the nucleotide sequence of SEQ ID NOs: 1, 3, 4, and 6 but still encodes the same DvLGIC/GluCl protein as SEQ ID NO:1, 3, 4 and 6. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the DvLGIC/GluCl channel protein in the host. In other words, this redundancy in the various codons which code for specific amino acids is within the scope of the present invention. Therefore, this invention is also directed to those DNA sequences which encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Another source of sequence variation may occur through RNA editing, as discussed infra. Such RNA editing may result in another form of codon redundancy, wherein a change in the open reading frame does not result in an altered amino acid residue in the expressed protein. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

Included in the present invention are DNA sequences that hybridize to SEQ ID NOs: 1, 3, 4 and 6 under moderate to highly stringent conditions. By way of example, and not limitation, a procedure using conditions of high stringency is as follows: Prehybridization of filters containing DNA is carried out for 2 hours to overnight at 65° C. in buffer composed of 6×SSC, 5×Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5-20×$10^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5×Denhardt's solution, 50% formamide at 42° C. for 12 to 48 hours or a washing step carried out in 0.2× SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook et al., 1989, Molecular Cloning: A Laboratory Manual; Cold Spring Harbor Laboratory, Cold Spring Harbor, N.Y. In addition to the foregoing, other conditions of high stringency which may be used are well known in the art.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.,: (Computational Molecular Biology, Lesk, A. M., ed. Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds. Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptide sequences, the term "identity" is well known to skilled artisans (Carillo and Lipton, 1988, SIAM J Applied Math 48: 1073). Methods commonly employed to determine identity or similarity between two sequences include, but are not limited to, those disclosed in Guide to Huge Computers, Martin J. Bishop, ed., Academic Press, San Diego, 1994, and Carillo and Lipton, 1988, SIAM J. Applied Math 48: 1073. Methods to determine identity and similarity are codified in computer programs. Preferred computer program methods to determine identity and similarity between two sequences include, but are not limited to, GCG program package (Devereux, et al, 1984, Nucleic Acids Research 12 (1): 387), BLASTN, FASTA (Altschul, et al., 1990, J. Mol. Biol. 215: 403).

As an illustration, by a polynucleotide having a nucleotide sequence having at least, for example, 95% "identity" to a reference nucleotide sequence of SEQ ID NO:1 is intended that the nucleotide sequence of the polynucleotide is identical to the reference sequence except that the polynucleotide sequence may include up to five point mutations or alternative nucleotides per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

These mutations or alternative nucleotide substitutions of the reference sequence may occur at the 5' or 3' terminal positions of the reference nucleotide sequence or anywhere between those terminal positions, interspersed either individually among nucleotides in the reference sequence or in one or more contiguous groups within the reference sequence. One source of such a "mutation" or change which results in a less than 100% identity may occur through RNA editing. The process of RNA editing results in modification of an mRNA molecule such that use of that modified mRNA as a template to generate a cloned cDNA may result in one or more nucleotide changes, which may or may not result in a codon change. This RNA editing is known to be catalyzed by an RNA editase. Such an RNA editase is RNA adenosine deaminase, which converts an adenosine residue to an inosine residue, which tends to mimic a cytosine residue. To this end, conversion of an mRNA residue from A to I will result in A to G transitions in the coding and noncoding regions of a cloned cDNA (e.g., see Hanrahan et al, 1999, Annals New York Acad. Sci. 868: 51-66); for a review see Bass (1997, TIBS 22: 157-162).

Similarly, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence of anywhere between those terminal positions, interspersed either individually among residues in the reference sequence or in one or more contiguous groups within the reference sequence. Again, as noted above, RNA editing may result in a codon change which will result in an expressed protein which differs in "identity" from other proteins expressed from "non-RNA edited" transcripts, which correspond directly to the open reading frame of the genomic sequence.

The present invention also relates to recombinant vectors and recombinant hosts, both prokaryotic and eukaryotic, which contain the substantially purified nucleic acid molecules disclosed throughout this specification. The nucleic acid molecules of the present invention encoding a DvLGIC/ GluCl channel protein, in whole or in part, can be linked with other DNA molecules, i.e., DNA molecules to which the DvLGIC/GluCl coding sequence are not naturally linked, to form "recombinant DNA molecules" which encode a respective DvLGIC/GluCl channel protein. The novel DNA sequences of the present invention can be inserted into vectors which comprise nucleic acids encoding DvLGIC/GluCl or a functional equivalent. These vectors may be comprised of DNA or RNA; for most cloning purposes DNA vectors are preferred. Typical vectors include plasmids, modified viruses, bacteriophage, cosmids, yeast artificial chromosomes, and other forms of episomal or integrated DNA that can encode a DvLGIC/GluCl channel protein. It is well within the purview of the skilled artisan to determine an appropriate vector for a particular gene transfer or other use.

The present invention also relates to a substantially purified form of a respective DvLGIC/GluCl channel protein, which comprise the amino acid sequence disclosed in FIG. 2, FIG. 5 and FIG. 7, and as set forth in SEQ ID NOs: 2, 5, and 7, respectively. The disclosed DvLGIC/GluCl proteins contain an open reading frame of 397 amino acids (DvLGIC/GluCl 1 and DvLGIC/GluCl 11, SEQ ID NO:2), 422 amino acids (DvLGIC/GluCl 7-1, SEQ ID NO:5) and 323 amino acids (DvLGIC/GluCl 10-2, SEQ ID NO:7) in length, as shown in FIGS. 2, 5, and 7, and as follows:

```
DvLGIC/GluCl 1 and DvLGIC/GluCl 11
                                          (SEQ ID NO: 2)
MPLSALNVWR ACVTLSLLRT TLAQERRSNG ALDDLEKLDD

LLRTYDRRAL PTTHLGTPTK VACEIYIRSF GSINPATMDY

EVDLYLRQTW QDDRLTSPNV SRPLDLNDPK LVQRIWKPEV

FFANAKHAEF QYVTVPNVLV RVNPNGKILY MLRLKLRFAC

MMDLYRFPMD SQVCSIELAS FSKTTEELHL EWSDTNPIIL

FEGLKLPQFE IQNINTSICM EKFHIGEYSC LKADFHLQRS

LGYHMVQSYL PTVLIVVISW VSFWLDVESI PARTTLGVTT

LLTISSKGSG IQSNLPPVSY VKAIDVWMGA CTGFVFSALL

EFTVVSCLAR MQARDKESSM VTTKHGVAIV NAVPDNQASV

PCTVRAKTID QVCRVAFPAI FLVFNAIYWP YFMCFTE;

DvLGIC/GluCl 7-1
                                          (SEQ ID NO: 5)
MIPASVALGR RMCSLLLAVG CATTSAWFAQ AVDHIDKGYP

APGLFDDVDL QILDNILWSY DRRITPGHHL NVPTVVKCEI

YLRSFGAVNP ATMDYDVDLY LRQTWTDLRM KNANLTRSLD

LNDPNLLKKV WKPDVYFPNA KHGEFQFVTV PNVLLRIYPT

GDILYMLRLK LTFSCMMNME RYPLDRQVCS IELASFSKTT

KEVELQWGNA EAVTMYSGLK MAQFELQQIS LTKCSGAFQI

GEYSCLRAEL NLKRSIGHHL VQSYLPSTLI VVVSWVSFWL

DVDAIPARIT LGVTTLLTIS SESSDHQANL APVSYVKALD

VWMGTCTMFV FAAVLEFTFV SYLARRKQIV PASIADVEAS

QDLVLVVGNK DKNRPPSPSI PTSTHVVLAY RHRAKQIDQV

SRVAFPIGFV LFNALYWPYY LL;
and,

DvLGIC/GluCl 10-2
```

-continued (SEQ ID NO: 7)

```
MSGISGPLDL NDPKLVQRIW KPEVFFANAK HAEFQYVTVP

NVLVRISPTG DILYMLRLKL TFSCMMDLYR YPLDAQVCSI

ELASFSKTTD ELQLHWSKAS PVILYENMKL PQFEIQNVNT

SLCNETFHIG EYSCLKAEFN LQRSIGYHLV QSYLPTILIV

VISWVSFWLD VEAIPARITL GVTTLLTISS KGAGIQGNLP

PVSYVKAIDV WMGACTMFVF AALLEFTFVN YLWRKRPATA

KSPPPVVAAI PESKVAVLLP CNGNLGPCSP ITGGTDISPS

PTGPEAVRNR HKVQAKRIDQ TCRIAFPMAF LAFSVAYWPY

YLL.
```

FIG. 8 shows the amino acid sequence comparison for DvLGIC/GluCl 1 and 11 (SEQ ID NO:2), DvLGIC/GluCl 7-1 (SEQ ID NO:5) and DvLGIC/GluCl 10-2 (SEQ ID NO:7) proteins.

The present invention also relates to biologically active fragments and/or mutants of the DvLGIC/GluCl proteins comprising the amino acid sequence as set forth in SEQ ID NOs: 2, 5, and 7, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists of DvLGIC/GluCl function.

Another preferred aspect of the present invention relates to a substantially purified, fully processed LGIC/GluCl channel protein obtained from a recombinant host cell containing a DNA expression vector comprises a nucleotide sequence as set forth in SEQ ID NOs: 1, 3, 4, and/or 6, and expresses the respective DvLGIC/GluCl precursor protein. It is especially preferred that the recombinant host cell be a eukaryotic host cell, including but not limited to a mammalian cell line, an insect cell line such as S2 cells, or Xenopus oocytes, as noted above.

As with many proteins, it is possible to modify many of the amino acids of DvLGIC/GluCl channel protein and still retain substantially the same biological activity as the wild type protein. Thus this invention includes modified DvLGIC/GluCl polypeptides which have amino acid deletions, additions, or substitutions but that still retain substantially the same biological activity as a respective, corresponding DvLGIC/GluCl. It is generally accepted that single amino acid substitutions do not usually alter the biological activity of a protein (see, e.g., Molecular Biology of the Gene, Watson et al., 1987, Fourth Ed., The Benjamin/Cummings Publishing Co., Inc., page 226; and Cunningham & Wells, 1989, Science 244: 1081-1085). Accordingly, the present invention includes polypeptides where one amino acid substitution has been made in SEQ ID NO:2, 5, and/or 7, wherein the polypeptides still retain substantially the same biological activity as a corresponding DvLGIC/GluCl protein. The present invention also includes polypeptides where two or more amino acid substitutions have been made in SEQ ID NO:2, 5, and. 7, wherein the polypeptides still retain substantially the same biological activity as a corresponding DvLGIC/GluCl protein. In particular, the present invention includes embodiments where the above-described substitutions are conservative substitutions.

One skilled in the art would also recognize that polypeptides that are functional equivalents of DvLGIC/GluCl and have changes from the DvLGIC/GluCl amino acid sequence that are small deletions or insertions of amino acids could also be produced by following the same guidelines, (i.e., minimizing the differences in amino acid sequence between DvLGIC/GluCl and related proteins). Small deletions or insertions are generally in the range of about 1 to 5 amino acids. The effect of such small deletions or insertions on the biological activity of the modified DvLGIC/GluCl polypeptide can easily be assayed by producing the polypeptide synthetically or by making the required changes in DNA encoding DvLGIC/GluCl and then expressing the DNA recombinantly and assaying the protein produced by such recombinant expression.

The present invention also includes truncated forms of DvLGIC/GluCl which contain the region comprising the active site of the enzyme. Such truncated proteins are useful in various assays described herein, for crystallization studies, and for structure-activity-relationship studies.

The present invention also relates to membrane-containing crude lysates, partially purified or substantially purified subcellular membrane fractions from the recombinant host cells (both prokaryotic and eukaryotic as well as both stably and transiently transformed/transfected cells) which contain the nucleic acid molecules of the present invention. These recombinant host cells express DvLGIC/GluCl or a functional equivalent, which becomes post translationally associated with the cell membrane in a biologically active fashion. These subcellular membrane fractions will comprise either wild-type or mutant forms of DvLGIC/GluCl at levels substantially above endogenous levels and hence will be useful in assays to select modulators of DvLGIC/GluCl proteins or channels. In other words, a specific use for such subcellular membranes involves expression of DvLGIC/GluCl within the recombinant cell followed by isolation and substantial purification of the membranes away from other cellular components and subsequent use in assays to select for modulators, such as agonist or antagonists of the protein or biologically active channel comprising one or more of the proteins disclosed herein. Alternatively, the lysed cells, containing the membranes, may be used directly in assays to select for modulators of the recombinantly expressed protein (s) disclosed herein. Therefore, another preferred aspect of the present invention relates to a substantially purified membrane preparation or lysed recombinant cell components which include membranes, which has been obtained from a recombinant host cell transformed or transfected with a DNA expression vector which comprises and appropriately expresses a complete open reading frame as set forth in SEQ ID NOs: 1, 3, 4, and/or 6, resulting in a functional form of the respective DvLGIC/GluCl channel. It is especially preferred that the recombinant host cell be a eukaryotic host cell, including but not limited to a mammalian cell line such as an insect cell line such as S2 cells, or Xenopus oocytes, as noted above.

Any of a variety of procedures may be used to clone DvLGIC/GluCl. These methods include, but are not limited to, (1) a RACE PCR cloning technique (Frohman, et al., 1988, Proc. Natl. Acad. Sci. USA 85: 8998-9002). 5' and/or 3' RACE may be performed to generate a full-length cDNA sequence. This strategy involves using gene-specific oligonucleotide primers for PCR amplification of DvLGIC/GluCl cDNA. These gene-specific primers are designed through identification of an expressed sequence tag (EST) nucleotide sequence which has been identified by searching any number of publicly available nucleic acid and protein databases; (2) direct functional expression of the DvLGIC/GluCl cDNA following the construction of a DvLGIC/GluCl-containing cDNA library in an appropriate expression vector system; (3) screening a DvLGIC/GluCl-containing cDNA library constructed in a bacteriophage or plasmid shuttle vector with a labeled degenerate oligonucleotide probe designed from the amino acid sequence of the DvLGIC/GluCl protein; (4) screening a DvLGIC/GluCl-containing cDNA library constructed in a bacteriophage or plasmid shuttle vector with a partial cDNA encoding the DvLGIC/GluCl protein. This partial cDNA is obtained by the specific PCR amplification of DvLGIC/GluCl DNA fragments through the design of degenerate oligonucleotide primers from the amino acid sequence known for other ion channel subunits which are related to the DvLGIC/GluCl protein; (5) screening a DvLGIC/GluCl-containing cDNA library constructed in a bacteriophage or plasmid shuttle vector with a partial cDNA or oligonucleotide with homology to a DvLGIC/GluCl protein. This strategy may also involve using gene-specific oligonucleotide primers for PCR amplification of DvLGIC/GluCl cDNA identified as an EST as described above; or (6) designing 5' and 3' gene specific oligonucleotides using SEQ ID NO:1, 3, 4 and/or 6 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding DvLGIC/GluCl. Alternatively, the DvLGIC/GluCl1 (1, 11 and 7-1) and DvLGIC/GluCl2 (10-2) cDNAs of the present invention may be cloned as described in Example Section 1.

It is readily apparent to those skilled in the art that other types of libraries, as well as libraries constructed from other cell types- or species types, may be useful for isolating a DvLGIC/GluCl-encoding DNA or a DvLGIC/GluCl homologue. Other types of libraries include, but are not limited to, cDNA libraries derived from other American dog tick cell types. It is readily apparent to those skilled in the art that suitable cDNA libraries may be prepared from cells or cell lines which have DvLGIC/GluCl activity. The selection of cells or cell lines for use in preparing a cDNA library to isolate a cDNA encoding DvLGIC/GluCl may be done by first measuring cell-associated DvLGIC/GluCl activity using any known assay available for such a purpose.

Preparation of cDNA Libraries can be Performed by Standard Techniques Well Known in the art. Well known cDNA library construction techniques can be found for example, in Sambrook et al., 1989, Molecular Cloning: A Laboratory Manual; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding DvLGIC/GluCl may also be isolated from a suitable genomic DNA library. Construction of genomic DNA libraries can be performed by standard techniques well known in the art. Well known genomic DNA library construction techniques can be found in Sambrook, et al., supra. One may prepare genomic libraries, especially in PI artificial chromosome vectors, from which genomic clones containing the DvLGIC/GluCl can be isolated, using probes based upon the DvLGIC/GluCl nucleotide sequences disclosed herein. Methods of preparing such libraries are known in the art (Ioannou et al., 1994, Nature Genet. 6: 84-89).

In order to clone a DvLGIC/GluCl gene by one of the preferred methods, the amino acid sequence or DNA sequence of a DvLGIC/GluCl or a homologous protein may be necessary. To accomplish this, a respective DvLGIC/GluCl channel protein may be purified and the partial amino acid sequence determined by automated sequenators. It is not necessary to determine the entire amino acid sequence, but the linear sequence of two regions of 6 to 8 amino acids can be determined for the PCR amplification of a partial DvLGIC/GluCl DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the DvLGIC/GluCl sequence but others in the set will be capable of hybridizing to DvLGIC/GluCl DNA even in the presence of DNA oligonucleotides with mismatches. The mismatched DNA oligonucleotides may still sufficiently hybridize to the DvLGIC/GluCl DNA to permit identification and isolation of DvLGIC/GluCl encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO:1, 3, 4, or 6 either for the purpose of isolating overlapping 5' and 3'RACE products for generation of a full-length sequence coding for DvLGIC/GluCl, or to isolate a portion of the nucleotide sequence coding for DvLGIC/GluCl for use as a probe to screen one or more cDNA- or genomic-based libraries to isolate a full-length sequence encoding DvLGIC/GluCl or DvLGIC/GluCl-like proteins.

This invention also includes vectors containing a DvLGIC/GluCl gene, host cells containing the vectors, and methods of making substantially pure DvLGIC/GluCl protein comprising the steps of introducing the DvLGIC/GluCl gene into a host cell, and cultivating the host cell under appropriate conditions such that DvLGIC/GluCl is produced. The DvLGIC/GluCl so produced may be harvested from the host cells in conventional ways. Therefore, the present invention also relates to methods of expressing the DvLGIC/GluCl protein and biological equivalents disclosed herein, assays employing these gene products, recombinant host cells which comprise DNA constructs which express these proteins, and compounds identified through these assays which act as agonists or antagonists of DvLGIC/GluCl activity.

The cloned DvLGIC/GluCl cDNA obtained through the methods described above may be recombinantly expressed by molecular cloning into an expression vector (such as pcDNA3. neo, pcDNA3.1, pCR2.1, pBlueBacHis2 or pLIT-MUS28, as well as other examples, listed infra) containing a suitable promoter and other appropriate transcription regulatory elements, and transferred into prokaryotic or eukaryotic host cells to produce recombinant DvLGIC/GluCl. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and mammalian cells (e.g., HEL human cells). Specifically designed vectors allow the shuttling of DNA between hosts such as bacteria-yeast or bacteria-mammalian cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. To determine the DvLGIC/GluCl cDNA sequence(s) that yields optimal levels of DvLGIC/GluCl, cDNA molecules including but not limited to the following can be constructed: a cDNA fragment containing the full-length open reading frame for DvLGIC/GluCl as well as various constructs containing portions of the cDNA encoding only specific domains of the protein or rearranged domains of the protein. All constructs can be designed to contain none, all or portions of the 5' and/or 3' untranslated region of a DvLGIC/GluCl cDNA. The expression levels and activity of DvLGIC/GluCl can be determined following the introduction, both singly and in combination, of these constructs into appropriate host cells. Following determination of the DvLGIC/GluCl cDNA cassette yielding optimal expression in transient assays, this DvLGIC/GluCl cDNA construct is transferred to a variety of expression vectors (including recombinant viruses), including but not limited to those for mammalian cells, plant cells, insect cells, oocytes, bacteria, and yeast cells. Techniques for such manipulations can be found described in Sambrook, et al., supra, are well known and available to the artisan of ordinary skill in the art. Therefore, another aspect of the present invention includes host cells that have been engineered to contain and/or express DNA sequences encoding the DvLGIC/GluCl. An expression vector containing DNA encoding a DvLGIC/GluCl-like protein may be used for expression of DvLGIC/GluCl in a recombinant host cell. Such recombinant host cells can be cultured under suitable conditions to produce DvLGIC/GluCl or a biologically equivalent form. Expression vectors may include, but are not limited to, cloning vectors, modified cloning vectors, specifically designed plasmids or viruses. Commercially available mammalian expression vectors which may be suitable for recombinant DvLGIC/GluCl expression, include but are not limited to, pcDNA3. neo (Invitrogen), pcDNA3.1 (Invitrogen), pCI-neo (Promega), pLITMUS28, pLITMUS29, pLITMUS38 and pLITMUS39 (New England Biolabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565). Also, a variety of bacterial expression vectors may be used to express recombinant DvLGIC/GluCl in bacterial cells. Commercially available bacterial expression vectors which may be suitable for recombinant DvLGIC/GluCl expression include, but are not limited to pCR2.1 (Invitrogen), pET11a (Novagen), lambda gt11 (Invitrogen), and pKK223-3 (Pharmacia). In addition, a variety of fungal cell expression vectors may be used to express recombinant DvLGIC/GluCl in fungal cells. Commercially available fungal cell expression vectors which may be suitable for recombinant DvLGIC/GluCl expression include but are not limited to pYES2 (Invitrogen) and *Pichia* expression vector (Invitrogen). Also, a variety of insect cell expression vectors may be used to express recombinant protein in insect cells. Commercially available insect cell expression vectors which may be suitable for recombinant expression of DvLGIC/GluCl include but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *D. vari-abilis* and silkworm derived cell lines. For instance, one insect expression system utilizes *Spodoptera frugiperda* (Sf21) insect cells (Invitrogen) in tandem with a baculovirus expression vector (pAcG2T, Pharmingen). Also, mammalian species which may be suitable and which are commercially available, include but are not limited to, L cells L-M (TK⁻) (ATCC CCL 1. 3), L cells L-M (ATCC CCL 1. 2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26), MRC-5 (ATCC CCL 171) and CPAE (ATCC CCL 209).

A preferred aspect for screening for modulators of DvLGIC/GluCl channel activity is an expression system for electrophysiologically-based assays for measuring ligand gated channel activity (such as GluCl channel activity) comprising injecting the DNA or RNA molecules of the present invention into *Xenopus laevis* oocytes. The general use of *Xenopus* oocytes in the study of ion channel activity is known in the art (Dascal, 1987, Crit. Rev. Biochem. 22: 317-317; Lester, 1988, Science 241: 1057-1063; see also Methods of Enzymology, Vol. 207, 1992, Ch. 14-25, Rudy and Iverson, ed., Academic Press, Inc., New York). The *Xenopus* oocytes are injected with nucleic acid material, including but not limited to DNA, mRNA or cRNA which encode a ligand gated-channel, whereafter channel activity may be measured as well as response of the channel to various modulators.

The specificity of binding of compounds showing affinity for LGIC/GluCl is shown by measuring the affinity of the compounds for recombinant cells expressing the cloned receptor or for membranes from these cells, which form a functional homomultimeric or heteromultimeric channel. Expression of the cloned receptor and screening for compounds that bind to LGIC/GluCl or that inhibit the binding of a known ligand of LGIC/GluCl to these cells, or membranes prepared from these cells, provides an effective method for the rapid selection of compounds with high affinity for LGIC/GluCl. Compounds identified by the above method are likely to be agonists or antagonists of LGIC/GluCl and may be peptides, proteins or non-proteinaceous organic or inorganic molecules.

Accordingly, the present invention is directed to methods for screening for compounds which modulate the expression of DNA or RNA encoding a LGIC/GluCl protein as well as compounds which affect the function of the LGIC/GluCl protein. Methods for identifying agonists and antagonists of other receptors are well known in the art and can be adapted to identify agonists and antagonists of a LGIC/GluCl channel. For example, Cascieri et al. (1992, Molec. Pharmacol. 41: 1096-1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential ligand of the neurokinin receptor. Where binding of the substance such as an agonist or antagonist to LGIC/GluCl is measured, such binding can be measured by employing a labeled ligand. The ligand can be labeled in any convenient manner known to the art, e.g., radioactively, fluorescently, enzymatically.

Therefore, the present invention is directed to methods for screening for compounds which modulate the expression of DNA or RNA encoding a DvLGIC/GluCl protein. Compounds which modulate these activities may be DNA, RNA, peptides, proteins, or non-proteinaceous organic or inorganic molecules. Compounds may modulate by increasing or attenuating the expression of DNA or RNA encoding DvLGIC/GluCl, or the function of the DvLGIC/GluCl-based channels. Compounds that modulate the expression of DNA or RNA encoding DvLGIC/GluCl or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing DvLGIC/GluCl, antibodies to DvLGIC/GluCl, or modified DvLGIC/GluCl may be prepared by known methods for such uses.

To this end, the present invention relates in part to methods of identifying a substance which modulates LGIC/GluCl receptor activity, which involves:

(a) adding a test substance in the presence and absence of a LGIC/GluCl receptor protein wherein said LGIC/GluCl receptor protein comprises the amino acid sequence as set forth in SEQ ID NOs: 2, 5 and/or 7; and, (b) measuring and comparing the effect of the test substance in the presence and absence of the LGIC/GluCl receptor protein or respective functional channel.

In addition, several specific embodiments are disclosed herein to show the diverse types of screening or selection assays which the skilled artisan may utilize in tandem with an expression vector directing the expression of the LGIC/GluCl receptor protein. Methods for identifying ligands of other receptors are well known in the art and can be adapted to ligands of LGIC/GluCl. Therefore, these embodiments are presented as examples and not as limitations. To this end, the present invention includes assays by which LGIC/GluCl modulators (such as agonists and antagonists) may be identified. Accordingly, the present invention includes a method for determining whether a substance is a potential agonist or antagonist of LGIC/GluCl that comprises:

(a) transfecting or transforming cells with an expression vector that directs expression of LGIC/GluCl in the cells, resulting in test cells;

(b) allowing the test cells to grow for a time sufficient to allow LGIC/GluCl to be expressed and for a functional channel to be generated;

(c) exposing the cells to a labeled ligand of LGIC/GluCl in the presence and in the absence of the substance;

(d) measuring the binding of the labeled ligand to the LGIC/GluCl channel; where if the amount of binding of the labeled ligand is less in the presence of the substance than in the absence of the substance, then the substance is a potential ligand of LGIC/GluCl.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells may be harvested and resuspended in the presence of the substance and the labeled ligand. In a modification of the above-described method, step (c) is modified in that the cells are not harvested and resuspended but rather the radioactively labeled known agonist and the substance are contacted with the cells while the cells are attached to a substratum, e.g., tissue culture plates.

The present invention also includes a method for determining whether a substance is capable of binding to LGIC/GluCl, i.e., whether the substance is a potential modulator of LGIC/GluCl channel activation, where the method comprises:

(a) transfecting or transforming cells with an expression vector that directs the expression of LGIC/GluCl in the cells, resulting in test cells;

(b) exposing the test cells to the substance;

(c) measuring the amount of binding of the substance to LGIC/GluCl;

(d) comparing the amount of binding of the substance to LGIC/GluCl in the test cells with the amount of binding of the substance to control cells that have not been transfected with LGIC/GluCl;

wherein if the amount of binding of the substance is greater in the test cells as compared to the control cells, the substance is capable of binding to LGIC/GluCl. Determining whether the substance is actually an agonist or antagonist can then be accomplished by the use of functional assays, such as an electrophysiological assay described herein.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells are harvested and resuspended in the presence of the substance.

The above described assays may be functional assays, where electrophysiological assays (e.g., see Example 2) may be carried out in transfected mammalian cell lines, an insect cell line, or *Xenopus* oocytes to measure the various effects test compounds may have on the ability of a known ligand (such as glutamate) to activate the channel, or for a test compound to modulate activity in and of itself (similar to the effect of ivermectin on known GluCl channels). Therefore, the skilled artisan will be comfortable adapting the cDNA clones of the present invention to known methodology for both initial and secondary screens to select for compounds that bind and/or activate the functional LGIC/GluCl channels of the present invention.

A preferred method of identifying a modulator of a LGIC/GluCl channel protein comprise firstly contacting a test compound with a *D. variabilis* LGIC/GluCl channel protein selected from the group consisting of SEQ ID NO:2, SEQ ID NO:5; and SEQ ID NO:7; and, secondly measuring the effect of the test compound on the LGIC/GluCl channel protein. A preferred aspect involves using a *D. variabilis* LGIC/GluCl protein which is a product of a DNA expression vector contained within a recombinant host cell.

Another preferred method of identifying a compound that modulates LGIC/GluCl glutamate-gated channel protein activity comprises firstly injecting into a host cell a population of nucleic acid molecules, at least a portion of which encodes a *D. variabilis* GluCl channel protein selected from the group consisting of SEQ ID NO:2, SEQ ID NO:5, and SEQ ID NO:7, such that expression of said portion of nucleic acid molecules results in an active ligand-gated channel, secondly measuring host cell membrane current in the presence and absence of a test compound. Numerous templates may be used, including but not limited to complementary DNA, poly A+ messenger RNA and complementary RNA.

The DNA molecules, RNA molecules, recombinant protein and antibodies of the present invention may be used to screen and measure levels of DvLGIC/GluCl. The recombinant proteins, DNA molecules, RNA molecules and antibodies lend themselves to the formulation of kits suitable for the detection and typing of DvLGIC/GluCl. Such a kit would comprise a compartmentalized carrier suitable to hold in close confinement at least one container. The carrier would further comprise reagents such as recombinant DvLGIC/GluCl or anti-DvLGIC/GluCl antibodies suitable for detecting DvLGIC/GluCl. The carrier may also contain a means for detection such as labeled antigen or enzyme substrates or the like.

The assays described herein can be carried out with cells that have been transiently or stably transfected with DvLGIC/GluCl. The expression vector may be introduced into host cells via any one of a number of techniques including but not limited to transformation, transfection, protoplast fusion, and electroporation.

Transfection is meant to include any method known in the art for introducing DvLGIC/GluCl into the test cells. For example, transfection includes calcium phosphate or calcium chloride mediated transfection, lipofection, infection with a retroviral construct containing DvLGIC/GluCl, and electroporation. The expression vector-containing cells are individually analyzed to determine whether they produce DvLGIC/GluCl protein. Identification of DvLGIC/GluCl expressing cells may be done by several means, including but not limited to immunological reactivity with anti-DvLGIC/GluCl antibodies, labeled ligand binding, or the presence of functional, non-endogenous DvLGIC/GluCl activity.

The specificity of binding of compounds showing affinity for DvLGIC/GluCl is shown by measuring the affinity of the compounds for recombinant cells expressing the cloned receptor or for membranes from these cells. Expression of the cloned receptor and screening for compounds that bind to DvLGIC/GluCl or that inhibit the binding of a known, ligand of DvLGIC/GluCl to these cells, or membranes prepared from these cells, provides an effective method for the rapid selection of compounds with high affinity for DvLGIC/GluCl. Such ligands need not necessarily be radiolabeled but can also be nonisotopic compounds that can be used to displace bound radioactively, fluorescently or enzymatically labeled compounds or that can be used as activators in functional assays. Compounds identified by the above method are likely to be agonists or antagonists of DvLGIC/GluCl.

Therefore, the specificity of binding of compounds having affinity for DvLGIC/GluCl is shown by measuring the affinity of the compounds for recombinant cells expressing the cloned receptor or for membranes from these cells. Expression of the cloned receptor and screening for compounds that bind to DvLGIC/GluCl or that inhibit the binding of a known, radiolabeled ligand of DvLGIC/GluCl (such as glutamate, ivermectin or nodulisporic acid) to these cells, or membranes prepared from these cells, provides an effective method for the rapid selection of compounds with high affinity for DvLGIC/GluCl. Such ligands need not necessarily be radiolabeled but can also be nonisotopic compounds that can be used to displace bound radioactively, fluorescently or enzymatically labeled compounds or that can be used as activators in functional assays. Compounds identified by the above method again are likely to be agonists or antagonists of DvLGIC/GluCl. As noted elsewhere in this specification, compounds may modulate by increasing or attenuating the expression of DNA or RNA encoding DvLGIC/GluCl, or by acting as an agonist or antagonist of the DvLGIC/GluCl receptor protein. Again, these compounds that modulate the expression of DNA or RNA encoding DvLGIC/GluCl or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample.

Expression of DvLGIC/GluCl DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of DvLGIC/GluCl in a host cell, DvLGIC/GluCl protein may be recovered to provide DvLGIC/GluCl protein in active form. Several DvLGIC/GluCl protein purification procedures are available and suitable for use. Recombinant DvLGIC/GluCl protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant DvLGIC/GluCl protein can be separated from other cellular proteins by use of an immunoaffinity column made with monoclonal or polyclonal antibodies specific for full-length DvLGIC/GluCl protein, or polypeptide fragments of DvLGIC/GluCl protein.

*D. variabilis* channel functional assays measure one or more ligand-gated chloride channel activities where the channel is made up in whole, or in part, by the DvLGIC/GluCl channel. DvLGIC/GluCl channel activity can be measured using the channel described herein by itself; or as a subunit in combination with one or more additional ligand-gated chloride channel subunits (preferably one or more DvLGIC/GluCl), where the subunits combine together to provide functional channel activity. Assays measuring DvLGIC/GluCl-gated chloride channel activity include functional screening using $^{36}$Cl, functional screening using patch clamp electrophysiology and functional screening using fluorescent dyes. Techniques for carrying out such assays in general are well known in the art. (See, for example, Smith et al., 1998, European Journal of Pharmacology 159: 261-269; González and Tsien, 1997, Chemistry & Biology 4: 269-277; Millar et al., 1994, Proc. R. Soc. Lond. B. 258: 307-314; Rauh et al., 1990 TiPS 11: 325-329, and Tsien et al., U.S. Pat. No. 5,661,035.) Functional assays can be performed using individual compounds or preparations containing different compounds. A preparation containing different compounds where one or more compounds affect DvLGIC/GluCl channel activity can be divided into smaller groups of compounds to identify the compound (s) affecting DvLGIC/GluCl channel activity. In an embodiment of the present invention a test preparation containing at least 10 compounds is used in a functional assay. Recombinantly produced DvLGIC/GluCl channels present in different environments can be used in a functional assay. Suitable environments include live cells and purified cell extracts containing the DvLGIC/GluCl channel and an appropriate membrane for activity; and the use of a purified DvLGIC/GluCl channel produced by recombinant means that is introduced into a different environment suitable for measuring DvLGIC/GluCl channel activity. DvLGIC/GluCl derivatives can be used to assay for compounds active at the channel and to obtain information concerning different regions of the channel. For example, DvLGIC/GluCl channel derivatives can be produced where amino acid regions in the native channel are altered and the effect of the alteration on channel activity can be measured to obtain information regarding different channel regions.

Polyclonal or monoclonal antibodies may be raised against DvLGIC/GluCl or a synthetic peptide (usually from about 9 to about 25 amino acids in length) from a portion of DvLGIC/GluCl 1 (i.e., 1, 11 or 7-1) or DvLGIC/GluCl2 (10-2) as disclosed in SEQ ID NOs: 2, 5 and/or 7. Monospecific antibodies to DvLGIC/GluCl are purified from mammalian antisera containing antibodies reactive against DvLGIC/GluCl or: are prepared as monoclonal antibodies reactive with DvLGIC/GluCl using the technique of Kohler and Milstein (1975, Nature 256: 495-497). Monospecific antibody as used herein is defined as a single antibody species or multiple antibody species with homogenous binding characteristics for DvLGIC/GluCl. Homogenous binding as used herein refers to the ability of the antibody species to bind to a specific antigen or epitope, such as those associated with DvLGIC/GluCl, as described above. Human DvLGIC/GluCl-specific antibodies are raised by immunizing animals such as mice, rats, guinea pigs, rabbits, goats, horses and the like, with an appropriate concentration of DvLGIC/GluCl protein or a synthetic peptide generated from a portion of DvLGIC/GluCl with or without an immune adjuvant.

Preimmune serum is collected prior to the first immunization. Each animal receives between about 0.1 mg and about 1000 mg of DvLGIC/GluCl protein associated with an acceptable immune adjuvant. Such acceptable adjuvants include, but are not limited to, Freund's complete, Freund's incomplete, alum-precipitate, water in oil emulsion containing Co7ynebacterium parvum and tRNA. The initial immunization consists of DvLGIC/GluCl protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of DvLGIC/GluCl in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with DvLGIC/GluCl are prepared by immunizing inbred mice, preferably Balb/c, with DvLGIC/GluCl protein. The mice are immunized by the IP or SC route with about 1 mg to about 100 mg, preferably about 10 mg, of DvLGIC/GluCl protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of DvLGIC/GluCl in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using DvLGIC/GluCl as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in Tissue Culture Methods and Applications, Kruse and Paterson, Eds., Academic Press.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8-12 days after cell transfer and the monoclonal antibodies are purified by techniques known in the art.

In vitro production of anti-DvLGIC/GluCl mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of DvLGIC/GluCl in body fluids or tissue and cell extracts.

It is readily apparent to those skilled in the art that the above described methods for producing monospecific antibodies may be utilized to produce antibodies specific for DvLGIC/GluCl peptide fragments, or a respective full-length DvLGIC/GluCl.

DvLGIC/GluCl antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing full-length DvLGIC/GluCl or DvLGIC/GluCl protein fragments are slowly passed through the column. The column is then washed with phosphate buffered saline until the optical density (A280) falls to background, then the protein is eluted with 0.23M glycine-HCl (pH 2.6). The purified DvLGIC/GluCl protein is then dialyzed against phosphate buffered saline.

The present invention also relates to a non-human transgenic animal which is useful for studying the ability of a variety of compounds to act as modulators of DvLGIC/GluCl, or any alternative functional DvLGIC/GluCl channel in vivo by providing cells for culture, in vitro. In reference to the transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art. A type of target cell for transgene introduction is the embryonic stem cell (ES). ES cells can be obtained from pre-implantation embryos cultured ill vitro and fused with embryos (Evans et al., 1981, Nature 292: 154-156; Bradley et al., 1984, Nature 309: 255-258; Gossler et al., 1986, Proc. Natl. Acad. Sci. USA 83: 9065-9069; and Robertson et al., 1986 Nature 322: 445-448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, Science 240: 1468-1474).

The present invention also relates to a non-human transgenic animal which is useful for studying the ability of a variety of compounds to act as modulators of DvLGIC/GluCl. In regard to transgenic animals of this invention, reference is made to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. Of course, a gene is a nucleotide sequence that encodes a protein, such as one or a combination of the cDNA clones described herein. The gene and/or transgene may also include genetic regulatory elements and/or structural elements known in the art. A type of target cell for transgene introduction is the embryonic stem cell (ES). ES cells can be obtained from pre-implantation embryos cultured in vitro and fused with embryos (Evans et al., 1981, Nature 292: 154-156; Bradley et al., 1984, Nature 309: 255-258; Gossler et al., 1986, Proc. Natl. Acad. Sci. USA 83: 9065-9069; and Robertson et al., 1986 Nature 322: 445-448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, Science 240: 1468-1474).

A naturally occurring DvLGIC/GluCl gene is referred to as the native gene, and if it is not mutant, it can also be referred to as wild-type. An altered DvLGIC/GluCl gene should not fully encode the same LGIC/GluCl as native to the host animal, and its expression product can be altered to a minor or greater degree, or absent altogether. In cases where it is useful to express a non-native DvLGIC/GluCl gene in a transgenic animal in the absence of a native LGIC/GluCl gene (such as within C. elegans), we prefer that the altered LGIC/GluCl gene induce a null knockout phenotype in the animal. However a more modestly modified LGIC/GluCl gene can also be useful and is within the scope of the present invention. The DvLGIC/GluCl mutation may be a targeted deletion mutation, a targeted substitution mutation and/or a targeted insertion mutation. However, the preferred mutation is a deletion mutation, and especially preferred is a deletion mutation which results in a deletion of most if not all of the DvLGIC/GluCl gene. Transgenic animals are generated which have an altered, or preferably, completely deleted LGIC/GluCl gene. LGIC/GluCl gene deletions, gene modifications and or gene insertions can render the native gene nonfunctional, producing a "knockout" transgenic animal, or can lead to a LGIC/GluCl with altered expression or activity. As noted above, a non-human transgenic animal without an activated DvLGIC/GluCl gene can be used to for testing/screening of modulators of DvLGIC/GluCl expression and/or activity (modulators such as small molecules or peptides) that may reverse the pathological phenotype which results from the overexpression or deletion of DvLGIC/GluCl.

A preferred deletion mutation may contain a deletion of anywhere from 1 nucleotide to deletion of the entire gene, including the open reading frame and associated cis-acting regulatory sequences associated with wild type DvLGIC/GluCl. A smaller deletion within the open reading frame is preferably not divisible by three, so as to result in a frameshift mutation resulting in a protein which most likely is non-functional. It is preferred that any such smaller deletion not divisible by three be targeted toward the 5' region of the open reading frame to increase the possibility of generating a non-functional truncated protein product. However, as noted above, it is preferable that the deletion mutation encompass most if not all of the DvLGIC/GluCl gene so as to insure prevention of expression of a functional DvLGIC/GluCl protein. Therefore, the DvLGIC/GluCl deficient animal cells, non-human transgenic embryos, non-human transgenic animals and non-human transgenic littermates of the present invention may be generated by any techniques known in the art, as sampled in the previous paragraph. It will also be within the purview of the skilled artisan to produce transgenic or knock-out invertebrate animals (e.g., C. elegans) which express the DvLGIC/GluCl transgene in a wild type C. elegans LGIC/GluCl background as well in C. elegans mutants deficient for one or more of the C. elegans LGIC/GluCl subunits.

Pharmaceutically useful compositions comprising modulators of DvLGIC/GluCl may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified DvLGIC/GluCl, or either DvLGIC/GluCl agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of disorders involving components of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to illustrate the present invention without, however, limiting the same hereto.

EXAMPLE 1

Isolation and Expression of cDNAs Encoding
DvLGIC/GluCl 1, DvLGIC/GluCl 11,
DvLGIC/GluCl 7-1 (DvGluCl1) and DvLGIC/GluCl
10-2 (DvGluCl2)

From a Tick *Dermacentor* cDNA Library

Generation of a tick *Dermacentor* cDNA library-PolyA+ RNA was purified from whole *Dermacentor* ticks to generate an oligo (dT)-primed ZAP cDNA library cloned as 5' EcoRI-3' XhoI inserts. The library consisted of approximately 1.8× 10$^6$ independent clones prior to amplification. The ZAP Express cDNA Synthesis Kit and the ZAP Express cDNA GigapackIII Gold Cloning Kit were purchased from Stratagene (La Jolla, Calif.) and used according to the manufacturer's instructions.

Library Screening and Isolation of *Dermacentor* LGIC/GluCl genes-Two DNA probes were used.

1. A first probe is from the tick *Rhipicephalus sanguineus* LGIC/GluCl1 (RsLGIC/GluCl 1) gene and was PCR amplified using as primers i) sense strand 5' CGG ATA TTG GAC AGC ATC 3' (SEQ ID NO:8) and ii) antisense strand 5' CCA GTA GAC GAG GTT GAA GAG G-3' (SEQ ID NO:9), to generate a fragment that runs from nucleotide 448 through 1645 of the RsLGIC/GluCl 1 open reading frame.

The nucleotide sequence of the RsLGIC/GluCl 1 probe is as follows:

```
                                              (SEQ ID NO: 10)
CGGATATTGG ACAGCATCAT TGGCCAGGGT CGTTATGACT

GCAGGATCCG GCCCATGGGA ATTAACAACA CAGACGGGCC

GGCTCTTGTA CGCGTTAACA TCTTTGTAAG AAGTATCGGC

AGAATTGATG ACGTCACCAT GGAGTACACA GTGCAAATGA

CGTTCAGAGA GCAGTGGCGG GACGAGAGAC TCCAGTACGA

CGACTTGGGC GGCCAGGTTC GCTACCTGAC GCTCACCGAA

CCGGACAAGC TTTGGAAGCC GGACCTGTTT TTCTCCAACG

AGAAAGAGGG ACACTTCCAC AACATCATCA TGCCCAACGT

GCTTCTACGC ATACATCCCA ACGGCGACGT TCTCTTCAGC

ATCAGAATAT CCTTGGTGCT TTCATGTCCG ATGAACCTGA

AATTTTATCC TTTGGATAAA CAAATCTGCT CTATCGTCAT

GGTGAGCTAT GGGTATACAA CAGAGGACCT GGTGTTTCTA

TGGAAAGAGG GGGATCCTGT ACAGGTCACA AAAAATCTCC

ACTTGCCACG TTTCACGCTG GAAAGGTTTC AAACCGACTA

CTGCACCAGT CGGACCAACA CTGGCGAGTA CAGCTGCTTG

CGCGTGGACC TGGTGTTCAA GCGCGAGTTC AGCTACTACC

TGATCCAGAT CTACATCCCG TGCTGCATGC TGGTCATCGT

GTCCTGGGTG TCGTTCTGGC TCGACCCCAC CTCGATCCCG

GCGCGAGTGT CGCTGGGCGT CACCACCCTG CTCACCATGG

CCACGCAGAT ATCGGGCATC AACGCCTCGC TGCCTCCCGT

TTCCTACACC AAGGCCATTG ACGTGTGGAC CGGCGTCTGT

CTGACCTTCG TATTCGGCGC GCTCCTCGAG TTCGCCCTGG

TCAACTACGC CTCGCGGTCA GATTCACGCC GGCAGAACAT

GCAGAAGCAG AAGCAGAGGA AATGGGAGCT CGAGCCGCCC

CTGGACTCGG ACCACCTGGA GGACGGCGCC ACCACGTTCG

CCATGAGGCC GCTGGTGCAC CACCACGGAG AGCTGCATGC

CGACAAGTTG CGGCAGTGCG AAGTCCACAT GAAGACCCCC

AAGACGAACC TTTGCAAGGC CTGGCTTTCC AGGTTTCCCA

CGCGATCCAA ACGCATCGAC GTCGTCTCGC GGATCTTCTT

TCCGCTCATG TTCGCCCTCT TCAACCTCGT CTACTGG
```

2. A second probe is from the tick *Rhipicephalus sanguineus* LGIC/GluCl 2 clone (RsLGIC/GluCl 2) gene which was PCR amplified using as primers i) sense strand 5'TGT GGT GGT GAT AGC TGC 3' (SEQ ID NO:11) and ii) antisense strand 5'GAG TTG ATC AAT CTG CTT GG 3' (SEQ ID NO:12), to generate a fragment that runs from nucleotide 166 through 1315 of the RsLGIC/GluCl 2 open reading frame. The nucleotide sequence of the RsLGIC/GluCl 1 probe is as follows:

```
                                         (SEQ ID NO: 13)
TGTGGTGGTG ATAGCTGCGT TCTGCTGGCC GCCCGCTCTG

CCGCTCGTAC CCGGGGGAGT TTCCTCCAGA GCAAACGATC

TGGACATTCT GGACGAGCTC CTCAAAAACT ACGATCGAAG

GGCCCTGCCG AGCAGTCACC TCGGAAATGC AACTATTGTG

TCATGCGAAA TTTACATACG AAGTTTTGGA TCAATAAATC

CTTCGAACAT GGACTACGAA GTCGACCTCT ACTTCCGGCA

GTCGTGGCTC GACGAGCGGT TACGCAAATC CACGCTATCT

CGTCCGCTCG ACCTTAATGA CCCAAAGCTG GTACAAATGA

TATGGAAGCC AGAAGTTTTC TTTGCGAACG CGAAACACGC

CGAGTTCCAA TATGTGACTG TACCTAACGT CCTCGTTAGG

ATCAACCCGA CTGGAATAAT CTTGTACATG TTGCGGTTAA

AACTGAGGTT CTCCTGCATG ATGGACCTGT ACCGGTACCC

CATGGATTCC CAAGTCTGCA GCATCGAAAT TGCCTCTTTT

TCCAAAACCA CCGAAGAGCT GCTGCTGAAA TGGTCCGAGA

GTCAGCCTGT CGTTCTCTTC GATAACCTCA AGTTGCCCCA

GTTTGAAATA GAGAAGGTGA ACACGTCCTT ATGCAAAGAA

AAGTTTCACA TAGGGGAATA CAGTTGCCTG AAAGCCGACT

TCTATCTGCA GCGTTCCCTC GGTTATCACA TGGTGCAGAC

CTATCTTCCG ACCACGCTTA TCGTGGTCAT CTCATGGGTG

TCATTCTGGC TCGACGTAGA CGCCATACCC GCCCGTGTCA

CCCTGGGCGT AACCACGCTG CTCACCATCT CATCCAAGGG

TGCCGGTATC CAGGGAAACC TGCCTCCCGT CTCGTACATC

AAGGCCATGG ACGTCTGGAT AGGATCCTGT ACTTCGTTTG

TCTTTGCGGC CCTTCTAGAG TTCACATTCG TCAACTATCT

CTGGAGGCGG CTGCCCAATA AGCGCCCATC TTCTGACGTA

CCGGTGACGG ATATACCAAG CGACGGCTCA AAGCATGACA

TTGCGGCACA GCTCGTACTC GACAAGAATG GACACACCGA

AGTTCGCACG TTGGTCCAAG CGATGCCACG CAGCGTCGGA

AAAGTGAAGG CCAAGCAGAT TGATCAACTC.
```

Vent DNA Polymerase for PCR was purchased from New England Biolabs (Boston Mass.). Each amplification cycle consisted of 1 min. at 95° C., 1 min. at 72° C., and 1 min. at 72° C. Following 35 cycles, there was a final 5 minute extension at 72° C. The PCR product was agarose gel purified, labeled with $^{32}$P-dCTP using the Random Primer DNA Labeling System (GibcoBRL, Gaithersburg, Md.), and the resulting RsLGIC/GluCl 1 (SEQ ID NO:11) probe was first employed to screen approximately 5.5×10$^5$ recombinants of the *Dermacentor* cDNA library. Hybridization was performed in 6×SSPE, 0.1% SDS, 10×Denhardt's solution, salmon sperm DNA (200 μg/ml), and 45% formamide at 42° C. The membranes were then washed twice in i) 2×SSC 0.5% SDS at room temperature for 15 min. and ii) 0.2×SSC 0.5% SDS at 42° C. for 30 min., followed by a single wash in 0.2×SSC, 0.5% SDS at 55° C. for 30 min. The RsLGIC/GluCl1 probe was removed from the membranes by i) incubating at −1 hour in a 0.05M NaOH+0.5M NaCl solution, then ii) incubating-1 hour in a 0.5M Tris: Cl (pH7.4) solution, then iii) rinsing in 1×SSPE all at room temperature. Eight positive clones, including DvLGIC/GluCl 1, DvLGIC/GluCl 11, DvLGIC/GluCl 7-1 and DvLGIC/GluCl 10-2 were identified in the original screen. DvLGIC/GluCl1, DvLGIC/GluCl 11, and DvLGIC/GluCl 7-1 were identified by both probes while DvLGIC/GluCl 10-2 was recognized only by RsLGIC/GluCl2 probe. All 6 inserts were excised from the phage, converted to pBK-CMV phagemid vectors using the manufacturer's protocol (Stratagene, La Jolla, Calif.), and sequenced on an ABI PRISM 377 DNA Sequencer (Perkin Elmer, Foster City Calif.). The DvLGIC/GluCl 1 cDNA insert is 3598 bp and is disclosed in FIG. 1A-C and is disclosed as SEQ ID NO:1. The DvLGIC/GluCl11 cDNA insert is 3442 bp and is disclosed in FIG. 3A-C and is disclosed as SEQ ID NO:3. The DvLGIC/GluCl 7-1 cDNA insert is 2194 bp and is disclosed in FIG. 4A-B and is disclosed as SEQ ID NO:4. Finally, the DvLGIC/GluCl10-2 cDNA insert is 4077 bp and is disclosed in FIG. 6A-C and is disclosed as SEQ ID NO:6.

Synthesis of in vitro transcribed capped RNA-A PCR strategy was used to add the T7 promoter upstream of the initiating methionine (ATG) and a polyA$^+$ tail following the stop codon (TAG) of the open reading frame (ORF) of clones DvLGIC/GluCl1, DvLGIC/GluCl 11, DvLGIC/GluCl 7-1 and DvLGIC/GluCl 10-2.

Amplified ORFs which contained the flanking T7 promoter and polyA$^+$ tail were used directly as templates in the in vitro transcription reaction (message machine Ambion, Austin, Tex.). After removal of DNA template, the volume was adjusted to 100 μl with nuclease free water, and RNA purified using a G-50 Sephadex Column (Boehringer Mannheim, Indianapolis, Ind.). The elutate was extracted with an equal volume of phenol/chloroform, followed with a second chloroform extraction, precipitated with isopropyl alcohol, and resuspended in nuclease-free water to a storage concentration of 1 μg/μl.

EXAMPLE 2

Functional expression of DvLGIC/GluCl 1 Clones in *Xenopus* Oocytes

*Xenopus laevis* oocytes were prepared and injected using standard methods previously described [Arena, J. P., Liu, K. K., Paress, P. S. & Cully, D. F. Mol. Pharmacol. 40, 368-374 (1991); Arena, J. P., Liu, K. K., Paress, P. S., Schaeffer, J. M. & Cully, D. F., Mol. Brain. Res. 15, 339-348 (1992)]. Adult female *Xenopus laevis* were anesthetized with 0.17% tricaine methanesulfonate and the ovaries were surgically removed and placed in a solution consisting of (mM): NaCl 82.5, KCl 2, MgCl2 1, HEPES 5, NaPyruvate 2.5, Penicillin G. 100,000 units/L, Streptomycin Sulfate 1000 mg/L, pH 7.5 (Mod. OR-2). Ovarian lobes were broken open, rinsed several times in Mod. OR-2, and incubated in 0.2% collagenase (Sigma, Type 1) in Mod. OR-2 at room temperature with gentle shaking. After 1 hour the collagenase solution was renewed and the oocytes were incubated for an additional 30-90 min until approximately 50% of the oocytes were released from the ovaries. Stage V and VI oocytes were selected and placed in media containing (mM): NaCl 96, KCl 2, MgCl$_2$ 1, CaCl$_2$ 1. 8, HEPES 5, NaPyruvate 2.5, theophylline 0.5, gentamicin 50 mg/ml, pH 7.5 (ND-96) for 16-24 hours before injection. Oocytes were injected with 50 nl of DvLGIC/GluCl 1 or DvLGIC/GluCl 7-1 RNA at a concentration of 0.2 mg/ml. Oocytes were incubated at 18° C. for 1-6 days in ND-96 before recording.

Recordings were made at room temperature in modified ND-96 consisting of (mM): NaCl 96, MgCl$_2$ 1, CaCl$_2$ 0.1, BaCl$_2$ 3.5, HEPES 5, pH 7.5. Oocytes were voltage clamped using a Dagan CA1 two microelectrode amplifier (Dagan Corporation, Minneapolis, Minn.) interfaced to a Macintosh 7100/80 computer. The current passing electrode was filled with 0.7M KCl, 1.7M Citrate, and the voltage recording electrode was filled with 1M KCl. Throughout the experiment oocytes were superfused with modified ND-96 (control solution) or with ND-96 containing potential channel activators and blockers at a rate of approximately 3 ml/min. Data were acquired at 100 Hz and filtered at 33.3 Hz using Pulse software from HEKA Elektronik (Lambrecht, Germany). All recordings were performed from a holding potential of either 0 or –30 mV.

Figure 10:
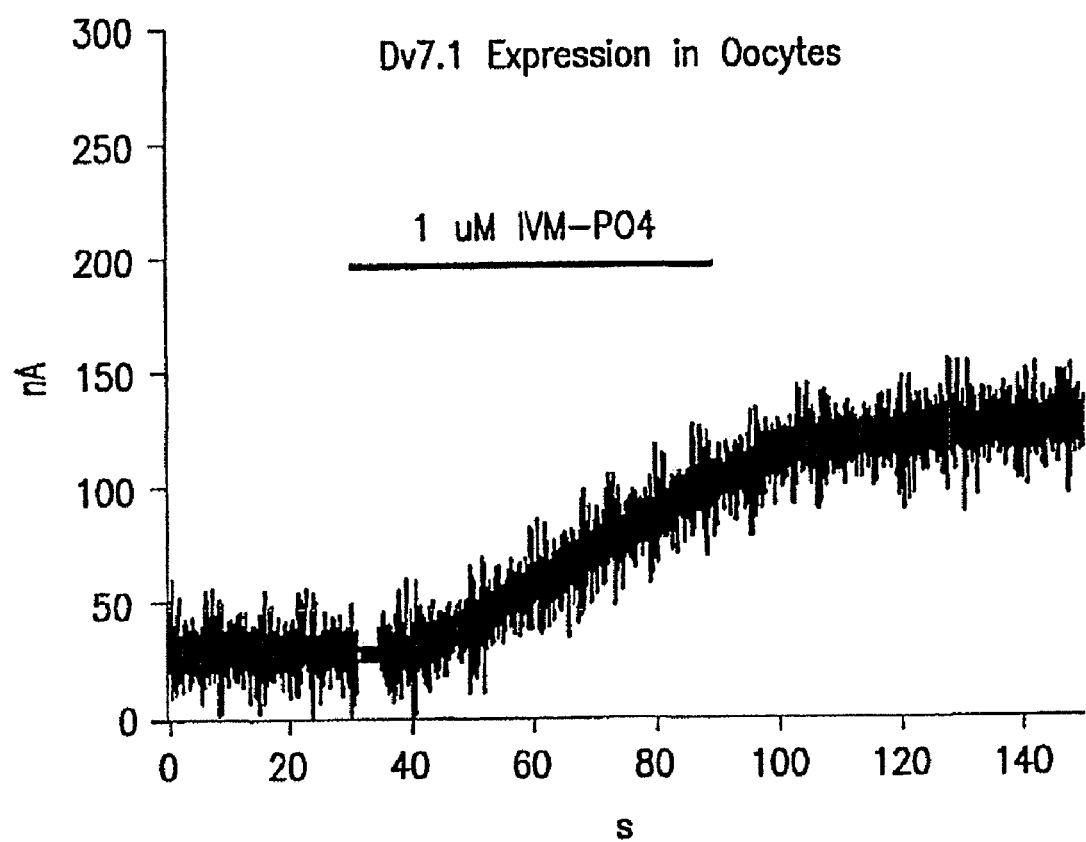
FIG. 10 shows activation by ivermectin with DvLGIC/GluCl 7-1 expressed in *Xenopus* oocytes. Current activation was maximal with ~1 µM ivermectin phosphate.

Oocytes expressing DvLGIC/GluCl 1 (FIG. 9) or DvLGIC/GluCl 7-1 (FIG. 10) exhibited a slowly activating current in response to application of 1 µM ivermectin phosphate. This current was irreversible upon wash-out of ivermectin phosphate. In contrast, application of 1 mM glutamate did not activate a current.

EXAMPLE 3

Functional expression of DvLGIC/GluCl Clones in Mammalian Cells

A DvLGIC/GluCl may be subcloned into a mammalian expression vector and used to transfect the mammalian cell line of choice. Stable cell clones are selected by growth in the presence of G418. Single G418 resistant clones are isolated and tested to confirm the presence of an intact DvLGIC/GluCl gene. Clones containing the DvLGIC/GluCls are then analyzed for expression using immunological techniques, such as immunoprecipitation, Western blot, and immunofluorescence using antibodies specific to the DvLGIC/GluCl proteins. Antibody is obtained from rabbits inoculated with peptides that are synthesized from the amino acid sequence predicted from the DvLGIC/GluCl sequences. Expression is also analyzed using patch clamp electrophysiological techniques and an anion flux assay.

Cells that are expressing DvLGIC/GluCl stably or transiently are used to test for expression of active channel proteins. These cells are used to identify and examine compounds for their ability to modulate, inhibit or activate the respective channel.

Cassettes containing the DvLGIC/GluCl cDNA in the positive orientation with respect to the promoter are ligated into appropriate restriction sites 3' of the promoter and identified by restriction site mapping and/or sequencing. These cDNA expression vectors may be introduced into fibroblastic host cells, for example, COS-7 (ATCC# CRL1651), and CV-1 tat [Sackevitz et al., 1987, Science 238: 1575], 293, L (ATCC# CRL6362) by standard methods including but not limited to electroporation, or chemical procedures (cationic liposomes, DEAE dextran, calcium phosphate). Transfected cells and cell culture supernatants can be harvested and analyzed for DvLGIC/GluCl expression as described herein.

All of the vectors used for mammalian transient expression can be used to establish stable cell lines expressing DvLGIC/GluCl. Unaltered DvLGIC/GluCl cDNA constructs cloned into expression vectors are expected to program host cells to make DvLGIC/GluCl protein. The transfection host cells include, but are not limited to, CV-1-P [Sackevitz et al., 1987, Science 238: 1575], tk-L [Wigler, et al., 1977, Cell 11: 223], NS/0, and dHFr-CHO [Kaufman and Sharp, 1982, J. Mol. Biol. 159:601].

Co-transfection of any vector containing a DvLGIC/GluCl cDNA with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of DvLGIC/GluCl are quantitated by the assays described herein. DvLGIC/GluCl cDNA constructs may also be ligated into vectors containing amplifiable drug-resistance markers for the production of mammalian cell clones synthesizing the highest possible levels of DvLGIC/GluCl.

Following introduction of these constructs into cells, clones containing the plasmid are selected with the appropriate agent, and isolation of an over-expressing clone with a high copy number of plasmids is accomplished by selection with increasing doses of the agent. The expression of recombinant DvLGIC/GluCl is achieved by transfection of full-length DvLGIC/GluCl cDNA into a mammalian host cell.

EXAMPLE 4

Cloning of DvLGIC/GluCl cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). A recombinant baculovirus expressing DvLGIC/GluCl cDNA is produced by the following standard methods (Invitrogen Maxbac Manual): The DvLGIC/GluCl cDNA constructs are ligated into the polyhedrin gene in a variety of baculovirus transfer vectors, including the pAC360 and the BlueBac vector (Invitrogen). Recombinant baculoviruses are generated by homologous recombination following co-transfection of the baculovirus transfer vector and linearized AcNPV genomic DNA [Kitts, 1990, Nuc. Acid. Res. 18:5667] into Sf9-cells. Recombinant pAC360 viruses are identified by the absence of inclusion bodies in infected cells and recombinant pBlueBac viruses are identified on the basis of b-galactosidase expression (Summers, M. D. and Smith, G. E., Texas Agriculture Exp. Station Bulletin No. 1555). Following plaque purification, DvLGIC/GluCl expression is measured by the assays described herein.

The cDNA encoding the entire open reading frame for DvLGIC/GluCl LGIC/GluCl is inserted into the BamHI site of pBlueBacII. Constructs in the positive orientation are identified by sequence analysis and used to transfect Sf9 cells in the presence of linear AcNPV mild type DNA.

EXAMPLE 5

Cloning of DvLGIC/GluCl cDNA into a Yeast Expression Vector

Recombinant DvLGIC/GluCl is produced in the yeast *S. cerevisiae* following the insertion of the optimal DvLGIC/GluCl cDNA cistron into expression vectors designed to direct the intracellular or extracellular expression of heterologous proteins. In the case of intracellular expression, vectors such as EmBLyex4 or the like are ligated to the DvLGIC/GluCl cistron [Rinas, et al., 1990, Biotechnology 8:543-545; Horowitz B. et al., 1989, J. Biol. Clieni. 265: 4189-4192]. For extracellular expression, the DvLGIC/GluCl LGIC/GluCl cistron is ligated to yeast expression vectors which fuse a secretion signal (a yeast or mammalian peptide) to the NH2 terminus of the DvLGIC/GluCl protein [Jacobson, 1989, Gene 85:511-516; Riett and Bellon, 1989, Biochem. 28: 2941-2949].

These vectors include, but are not limited to pAVE1-6, which fuses the human serum albumin signal to the expressed cDNA [Steep, 1990, Biotechnology 8: 42-46], and the vector pL8PL which fuses the human lysozyme signal to the expressed cDNA [Yamamoto, Bioche7n. 28: 2728-2732)]. In addition, DvLGIC/GluCl is expressed in yeast as a fusion protein conjugated to ubiquitin utilizing the vector pVEP [Ecker, 1989, J. Biol. Chem. 264: 7715-7719, Sabin, 1989 Biotechnology 7: 705-709, McDonnell, 1989, Mol. Cell. Biol. 9: 5517-5523 (1989)]. The levels of expressed DvLGIC/GluCl are determined by the assays described herein.

EXAMPLE 6

Purification of Recombinant DvLGIC/GluCl

Recombinantly produced DvLGIC/GluCl may be purified by antibody affinity chromatography. DvLGIC/GluCl LGIC/GluCl antibody affinity columns are made by adding the anti-DvLGIC/GluCl LGIC/GluCl antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized DvLGIC/GluCl are slowly passed through the column. The column is then washed with phosphate-buffered saline together with detergents until the optical density (A280) falls to background, then the protein is eluted with 0.23M glycine-HCl (pH 2.6) together with detergents. The purified DvLGIC/GluCl protein is then dialyzed against phosphate buffer

What is claimed is:

1. An isolated *D. variabilis* LGIC/GluCl channel protein which comprises the amino acid sequence as set forth in SEQ ID NO:5.

2. The *D. variabilis* LGIC/GluCl channel protein of claim 1 which is a product of a DNA expression vector contained within a recombinant host cell.

3. A purified membrane preparation comprising the *D. variabilis* LGIC/GluCl channel protein purified from the recombinant host cell of claim 2.

4. A *D. variabilis* LGIC/GluCl channel protein which consists of the amino acid sequence as set forth in SEQ ID NO:5.

5. The *D. variabilis* LGIC/GluCl channel protein of claim 4 which is a product of a DNA expression vector contained within a recombinant host cell.

6. A purified membrane preparation comprising the *D. variabilis* LGIC/GluCl channel protein purified from the recombinant host cell of claim 5.

7. A method of identifying a modulator of a LGIC/GluCl channel protein, comprising:
   (a) contacting a test compound with a *D. variabilis* LGIC/GluCl channel protein consisting of the amino acid sequence as set forth in SEQ ID NO:5; and,
   (b) measuring an effect of the test compound on the LGIC/GluCl channel protein.

8. The method of claim 7 wherein the *D. variabilis* LGIC/GluCl protein of step (a) is a product of a DNA expression vector contained within a recombinant host cell.

* * * * *

SEQUENCE LISTING

```
<160> NUMBER OF SEQ ID NOS: 13

<210> SEQ ID NO 1
<211> LENGTH: 3598
<212> TYPE: DNA
<213> ORGANISM: Dermacentor variabilis

<400> SEQUENCE: 1
gcgaggctgt cggtggaaag cgcggcgagc acgcgtccgc gcgcctgcgc tccagtccgg      60
acccgagctg gagcacggcc tggagggata ggtctggtcg accgtggttg cagctccaga     120
cgcgcagttg gagctcggcg aaggggctgc tgctgcgagc actgtgcgca tgccactttc     180
agcgctgaac gtgtggcgcg cttgcgtcac gttgtccctc ctcaggacga cgctcgcgca     240
ggaaaggcgg tcaaacggag cgctggatga cctggagaag cttgacgact tattaagaac     300
ctatgaccgg cgtgcccttc ccacgacaca cttgggaacg ccaacaaaag tggcttgcga     360
aatctacata cgcagcttcg ggtccataaa tccagccaca atggactatg aggttgatct     420
ttatttgcgg cagacttggc aagatgatcg cttgacgagc cccaacgtat ccaggcccct     480
ggacctcaat gatccaaagc tggtgcagcg tatatggaaa ccggaagtat tcttcgcaaa     540
tgccaaacac gcagagttcc aatatgtcac agtacctaat gtactggtcc gcgttaaccc     600
gaacggaaag attctataca tgctcaggct caagctaagg tttgcatgta tgatggattt     660
atatcgcttt cctatggact cccaagtttg cagcatcgaa ctcgcctcat tctcgaaaac     720
aaccgaagaa ctgcatctgg agtggtctga taccaatccg ataatactat tcgaaggcct     780
gaagttacca caattcgaga ttcagaatat aaatacgtca atctgcatgg agaaatttca     840
catcggagag tacagctgcc tgaaggccga cttccacttg cagcggtcac tgggctacca     900
catggtgcag tcgtatctgc ctacagtgct catcgtggtc atctcgtggg tgtccttctg     960
gctcgacgtt gagtccattc cggcgcgcac cacactgggc gtcacgacgc tgctcactat    1020
ttcttccaag ggctccggta tacagtccaa cttgcctccg gtctcatacg tgaaggcaat    1080
cgatgtgtgg atgggagcct gcacgggctt cgtgttctcg gcactactgg agttcaccgt    1140
cgtcagctgc ctggccagga tgcaggcacg agacaaggag tcaagtatgg ttacaacaaa    1200
gcacggagtg gcgattgtca acgctgttcc tgataaccag gcgtcggttc cttgcactgt    1260
```

```
ccgggcgaaa actattgacc aggtctgccg cgtagcgttt ccggccatct tcctcgtgtt    1320
taacgccatt tactggccgt attttatgtg ctttacagag tagaacatca ccgaacaacg    1380
caaaagttct gcggaaaaag tgtccgtata acgtgtcttg aggctcattg tcacgtattt    1440
acaccggcat gaaaggttcg ttaaatcaac caatatagcg tcctcagcca attacgcaca    1500
ctagtttaga gcagccagtc gcatttcctt tactactatc gagagaggtt ggactaagtc    1560
atgagttcat tcccttcggt agcttctgtc aattgtctca gggaaggata ggttggtgct    1620
tcgagctctt tagcgcatgc aaactctgtt gggatgctta ggtacgcgca gggaacgtga    1680
cgatctataa tgttttttgg agtagtaatg gaacacggca ctgacggtcg ataaatttga    1740
tagcatgagg aagtgaacta attactataa aatgcacaac ggctttattg tggagtattg    1800
cgcgttttct ttttataatg taggagggat agaatataag tgccaagaag cagataccta    1860
aaatcgtaaa acagcgccgc catgtagatg tctgatttag aagataccgt tgcactgcat    1920
cacaggcgta gcatacaaca aatttaagct cttctatagg aaatagaaat attgagtatt    1980
acttcgttaa tgcgggaatc gtatttgtta aatgtatctt tcgattaaca attgggactt    2040
tcgctgtttc aatacagact tgttgagcc ttcgtataac attacgaaaa aaaaagaaaa    2100
tctgaaaaga ataatatcta cgttttcaat accagccatt ctagtccaga aggcaagcgt    2160
gctgcaaaat ccgaaagcaa aatttattta tgttaaatat aacatcccgg tcatttgccc    2220
taactttgtg gcgacaattg acagcgtcaa ctaaactgcg tattccatgt tgtcgcttaa    2280
tggctttgcc atgatgccat cttagtcatt ttcagctgtt caaagtttta aggaataagc    2340
tatgcttaag ctacaattga ttgttaatga agtgtcagcg cgaagacttg cgagtttgat    2400
ttcgtacata tgagtgttct ttatacaccc tgacactacc tttttggagg cgatgagccg    2460
agaattcaga aaacgtcatg gccagttta acagaacagt gaccctgtta aaaatgtctg    2520
tatgaatact gttgttattt atggtagttt tgaaatcgtt taatatatgt tatgttacgt    2580
gatcaagtgt caatggctat acattatcga cctcccatta acttgatcaa tccaatcgtc    2640
cagacattta atgtccgagg aacttcaggt ttattaactg taggttaaaa ctctgatgta    2700
tatataacag catggaatgc aagatctcgt catatttcat gcaatttcac tagatgcagc    2760
gatgttttcg atggagatta ttcgtctcct gaaaaaaaaa attgacattc accggcatgt    2820
aggctgaagc tatgaagaaa acccagctgg gtttcctttg tagcttcgtt ttttttcctag   2880
ataaggttaa tatcttgatc tctgtgctac agtaagagtg aaactgaact cggcctgaaa    2940
aacttgcgtt ttcttatcgc actaccgtca ttgaaacgct cagtactagg tcttggtgaa    3000
acacatgact aaaatttgaa agctttagaa tgaatttatt tattttatt tatttacaaa    3060
tactgcaatc ccgttacggg attgcagtat ttgcattatg aaagaaacac attatgaaag    3120
aaacgagaaa cgcaatcttc gcattatgaa agaaacgagc agaagacaga tggctaattt    3180
tatttgctga ttgtagccca ttttcctctt actagagagt tatgggtgac agcagaattc    3240
tcagaatagt gcattctctt aaaataactt gacatcgtgt ggtaatttcc ctaaatctca    3300
tgtaggtaga tgctttattt atgtaatttg aggagacata cccatgaaaa cgaaaagatg    3360
acgggcgcta atggttatag aagtccttcc tgccactgtt ggctgaaatg tatttgtatg    3420
ttttttggtc agtcactgtg tcccaaagct tcttcgtgct gaagcttaag tgagtctatg    3480
ctgttcaaca ccattgtata tttttgtaat aaaatagttt attaaatgac ctggttctac    3540
ttgaaaaaaa aaaaaaaaaa aaaaaaaaaa aaaaaaaaaa aaaaaaaaaa aaaaaaa       3598
```

```
<210> SEQ ID NO 2
<211> LENGTH: 397
<212> TYPE: PRT
<213> ORGANISM: Dermacentor variabilis

<400> SEQUENCE: 2

Met Pro Leu Ser Ala Leu Asn Val Trp Arg Ala Cys Val Thr Leu Ser
  1               5                  10                  15

Leu Leu Arg Thr Thr Leu Ala Gln Glu Arg Arg Ser Asn Gly Ala Leu
             20                  25                  30

Asp Asp Leu Glu Lys Leu Asp Asp Leu Leu Arg Thr Tyr Asp Arg Arg
         35                  40                  45

Ala Leu Pro Thr Thr His Leu Gly Thr Pro Thr Lys Val Ala Cys Glu
     50                  55                  60

Ile Tyr Ile Arg Ser Phe Gly Ser Ile Asn Pro Ala Thr Met Asp Tyr
 65                  70                  75                  80

Glu Val Asp Leu Tyr Leu Arg Gln Thr Trp Gln Asp Asp Arg Leu Thr
                 85                  90                  95

Ser Pro Asn Val Ser Arg Pro Leu Asp Leu Asn Asp Pro Lys Leu Val
            100                 105                 110

Gln Arg Ile Trp Lys Pro Glu Val Phe Phe Ala Asn Ala Lys His Ala
        115                 120                 125

Glu Phe Gln Tyr Val Thr Val Pro Asn Val Leu Val Arg Val Asn Pro
    130                 135                 140

Asn Gly Lys Ile Leu Tyr Met Leu Arg Leu Lys Leu Arg Phe Ala Cys
145                 150                 155                 160

Met Met Asp Leu Tyr Arg Phe Pro Met Asp Ser Gln Val Cys Ser Ile
                165                 170                 175

Glu Leu Ala Ser Phe Ser Lys Thr Thr Glu Glu Leu His Leu Glu Trp
            180                 185                 190

Ser Asp Thr Asn Pro Ile Ile Leu Phe Glu Gly Leu Lys Leu Pro Gln
        195                 200                 205

Phe Glu Ile Gln Asn Ile Asn Thr Ser Ile Cys Met Glu Lys Phe His
    210                 215                 220

Ile Gly Glu Tyr Ser Cys Leu Lys Ala Asp Phe His Leu Gln Arg Ser
225                 230                 235                 240

Leu Gly Tyr His Met Val Gln Ser Tyr Leu Pro Thr Val Leu Ile Val
                245                 250                 255

Val Ile Ser Trp Val Ser Phe Trp Leu Asp Val Glu Ser Ile Pro Ala
            260                 265                 270

Arg Thr Thr Leu Gly Val Thr Thr Leu Leu Thr Ile Ser Ser Lys Gly
        275                 280                 285

Ser Gly Ile Gln Ser Asn Leu Pro Pro Val Ser Tyr Val Lys Ala Ile
    290                 295                 300

Asp Val Trp Met Gly Ala Cys Thr Gly Phe Val Phe Ser Ala Leu Leu
305                 310                 315                 320

Glu Phe Thr Val Val Ser Cys Leu Ala Arg Met Gln Ala Arg Asp Lys
                325                 330                 335

Glu Ser Ser Met Val Thr Thr Lys His Gly Val Ala Ile Val Asn Ala
            340                 345                 350

Val Pro Asp Asn Gln Ala Ser Val Pro Cys Thr Val Arg Ala Lys Thr
        355                 360                 365

Ile Asp Gln Val Cys Arg Val Ala Phe Pro Ala Ile Phe Leu Val Phe
    370                 375                 380

Asn Ala Ile Tyr Trp Pro Tyr Phe Met Cys Phe Thr Glu
```

<210> SEQ ID NO 3
<211> LENGTH: 3442
<212> TYPE: DNA
<213> ORGANISM: Dermacentor variabilis

<400> SEQUENCE: 3

| | | | | | | |
|---|---|---|---|---|---|---|
| cgaaggggct | gctgctgcga | gcactgtgcg | catgccactt | tcagcgctga | acgtgtggcg | 60 |
| cgcttgcgtc | acgttgtccc | tcctcaggac | gacgctcgcg | caggaaaggc | ggtcaaacgg | 120 |
| agcgctggat | gacctggaga | agcttgacga | cttattaaga | acctatgacc | ggcgtgccct | 180 |
| tcccacgaca | cacttgggaa | cgccaacaaa | agtggcttgc | gaaatctaca | tacgcagctt | 240 |
| cgggtccata | aatccagcca | caatggacta | tgaggttgat | cttttatttgc | ggcagacttg | 300 |
| gcaagatgat | cgcttgacga | gccccaacgt | atccaggccc | ctggacctca | atgatccaaa | 360 |
| gctggtgcag | cgtatatgga | aaccagaagt | attcttcgca | aatgcaaaac | acgcagagtt | 420 |
| ccaatatgtc | acagtaccta | atgtactggt | ccgcgttaac | ccgaacggaa | agattctata | 480 |
| catgctcagg | ctcaagctaa | ggtttgcatg | tatgatggat | ctatatcgct | ttcctatgga | 540 |
| ctcccaagtt | tgcagcatcg | aactcgcctc | attctcgaaa | acaaccgaag | aactgcatct | 600 |
| ggagtggtcc | gataccaatc | cgataatact | attcgaaggc | ctgaagttac | cacagttcga | 660 |
| gattcagaat | ataaatacgt | caatctgcat | ggagaaattt | cacatcggag | agtacagctg | 720 |
| cctgaaggcc | gacttccact | tgcagcggtc | actgggctac | cacatggtgc | agtcgtatct | 780 |
| gcctacagtg | ctcatcgtgg | tcatctcgtg | ggtgtccttc | tggctcgacg | ttgagtccat | 840 |
| tccggcgcgc | accacactgg | gcgtcacgac | gctgctcact | atttcttcca | agggctccgg | 900 |
| tatacagtcc | aacttgcctc | cggtctcata | cgtgaaggca | atcgatgtgt | ggatgggagc | 960 |
| ctgcacgggc | ttcgtgttct | cggcactact | ggagttcacc | gtcgtcagct | gcctggccag | 1020 |
| gatgcaggca | cgagacaagg | agtcaagcat | ggttacaaca | aagcacggag | tggcgattgt | 1080 |
| caacgctgtt | cctgataacc | aagcgtcggt | tccttgcact | gtccgggcga | aaactattga | 1140 |
| ccaggtctgc | cgcgtagcgt | ttccggccat | cttcctcgtg | tttaacgcca | tttactggcc | 1200 |
| gtactttatg | tgctttactg | agtagaacat | caccgaacaa | ggcaatagtt | ctgcggaaaa | 1260 |
| agtgtccgta | taacgtgtct | tgaggctcat | tgtcacgtat | ttacaccggc | atgaaaggta | 1320 |
| ggtcaaggga | gcgttcgtta | aatcaaccaa | tatagcgtcc | tcagccaatt | acgcacacta | 1380 |
| gtttagagca | gccagtcgaa | tttcctttac | tactatcgag | agaggttgga | ctaagtcatg | 1440 |
| agttcattcc | cttcggtagc | ttctgtcaat | tgtctcaggg | aaggataggt | tggtgcttcg | 1500 |
| agctctttag | cgcatgcaaa | ctctgttggg | atgcttaggt | acgcgcaggg | aacgtgacga | 1560 |
| tctataatgt | tttttggagt | agtaatggaa | cacggcactg | acggtcgata | aatttgatgg | 1620 |
| tatgaggaag | tgcactgatt | actataaaat | gcacaacggc | tttattgtgg | agtatggctc | 1680 |
| gttttctttt | tataatgtag | gagggataga | atataagtgc | caagaagcag | atacttaaaa | 1740 |
| tcctaaaaca | gcgccgccat | gtagatgtct | gatttagaag | ataccgttgc | actgcatcac | 1800 |
| aagcgtagca | tacaacaaat | ttaagctctt | ctataggaaa | tagaaatatt | gagtattact | 1860 |
| tcgttaatgc | gggaatcgta | tttgttaaat | gtatctttcg | attaacaatt | gggactttcg | 1920 |
| ctgtttcaat | acagactttt | ttgagccttc | gtataacatt | acgaaaaaaa | aagaaaatct | 1980 |
| gaaaagaata | atatctacgt | tttcaatacc | agccattcta | gtccagaagg | caagcgtgct | 2040 |
| gcaaaatccg | aaagcaaaat | ttatttatgt | taaatataac | atcccggtca | tttgccctaa | 2100 |

-continued

```
ctttgtggcg acaattgaca gcgtcaacta aactgcgtat tccatgttgt cgcttaatgg    2160
ctttgccatg atgccatctt agtcattttc agctgttcaa agttttaagg aataagctat    2220
gcttaagcta caattgattg ttaatgaagt gtcagcgcga agacttgcga gtttgatttc    2280
gtacatatga gtgttcttta tacaacctga cactaccttt ttggaggcga tgagccgaga    2340
attcagaaaa cgtcatggcc agttttaaca gaacagtgac cctgttaaaa tgtctgtata    2400
aatactgttg ttatttatgg tagttttgaa atcgtttaat atatgttatg ttacgtgatc    2460
aagtgtcaat ggctatacat tatcgacctc ccattaactt gatcaatcca atcgtccaga    2520
catttaatgt ccgaggaact tcaggtttat taactgtagg ttaaaactct gatgtatata    2580
taacagcatg gaatgcaaga tctcgtcata tttcatgcaa tttcactaga tgcagcgatg    2640
ttttcgatgg agattattcg tctcctgaaa aaaaaaattg acattcaccg gcatgtaggc    2700
tgaagctatg aaggaaaccc agctgggttt cctttgtagc ttcgtttttt tcctagataa    2760
ggttaatatc ttgatctctg tgctacagta agagtgaaac tgaactaggc ctgaaaaact    2820
tgcgttttct tatcgcacta ccttcattga aacgctcagt actaggtctt ggtgaaacac    2880
atgactaaaa tttgaaagct ttagaatgaa tttatttatt tttatttatt tacaaatact    2940
gcaatcccgt tacgggattg cagtatttgc attatgaaag aaacacatta tgaaagaaac    3000
gagaaacgca atcttcgcat tatgaaagaa acgagcagaa gacagatggc taattttatt    3060
tgctgattgt agcccatttt tctcttacta gagagttatg ggtgacagca gaattctcag    3120
aatagtgcat tctcttaaaa taacttgaca tcgtgtggta atttccctaa atctcatgta    3180
ggtagctgct ttatttatgt aatttgagga gacataccca tgaaaacgaa aagacgacgg    3240
gcgctaatga ttatagaagt ccttcctgcc actgttggct gaaatgtatt tgtatgtttt    3300
ttggtcagtc actgtgtccc aaagcttctt cgtgctgaag cttaagtgag tctatgctgt    3360
tcaacaccat tgtatatttt tgtaataaaa tagtttatta aatgacctgg ttctacttga    3420
aaaaaaaaaa aaaaaaaaaa aa                                             3442
```

<210> SEQ ID NO 4
<211> LENGTH: 2194
<212> TYPE: DNA
<213> ORGANISM: Dermacentor variabilis

<400> SEQUENCE: 4

```
ctcggtcgcg cgcgcacaca gcaagtgctc cggtgaggcg gctgatatga tcccggcgtc     60
cgtggctctc ggccgaagga tgtgctctct gctgctcgct gtcggatgcg ccacgactag    120
cgcctggttc gctcaggctg tcgaccacat cgacaaagga tacccagcac caggactctt    180
cgatgatgtc gaccttcaaa tattggacaa catcttatgg agctacgacc gacgcatcac    240
ccctggtcat catttaaacg ttcctacagt tgttaagtgc gagatatatc tcaggagttt    300
tggagctgtg aaccctgcaa caatggacta cgacgtagac ctgtacctgc gtcagacgtg    360
gacggacttg cggatgaaga acgccaacct gacccggtcc ctagacttaa acgaccccaa    420
cctcctcaag aaagtgtgga aacctgacgt ctactttccc aatgccaagc acggggagtt    480
ccagttcgtc actgttccca acgttctctt gaggatatac cctaccggcg atatactcta    540
catgttaagg ctaaagctaa cattctcctg catgatgaac atggagcggt accccctgga    600
ccgacaggtc tgcagcatcg agcttgcctc atttttccaag acgacaaagg aggttgagct    660
ccaatgggga aacgctgagg ctgtcaccat gtacagtggt ctgaagatgg cacaattcga    720
gcttcaacaa atcagcctga cgaagtgcag cggcgccttt cagataggcg agtacagctg    780
```

-continued cctgcgcgcg gagctcaact tgaagcgttc cattggccac cacctagtgc agtcttacct 840
gccgtccaca ctcatcgtgg tcgtgtcgtg ggtgtccttc tggctcgacg tggacgccat 900
accggcgcgc atcacgctgg gtgtcaccac gctcctcact atttcgtcgg agagctccga 960
ccaccaggcc aacctagcgc cggtgtcgta cgtgaaagcg ctcgacgtgt ggatgggcac 1020
gtgcaccatg ttcgtgttcg ccgcggtgct cgagttcacc ttcgtctcct acctcgctcg 1080
cagaaagcag atcgtgcccg cctctatcgc ggacgtcgag gcttcccaag atctcgttct 1140
tgtcgtggga aacaaggaca aaaatcgacc cccgtcaccg tccatcccga cgtccaccca 1200
cgtggtcttg gcttacagac accgtgccaa gcagatcgac caagtgagcc gggtcgcttt 1260
cccaatcggc tttgttctct tcaacgcact ctactggccc tattacttgc tctagttggc 1320
catggtctca gtgcctacag ctgctgctcc caacgtgcag ccatacgccg ggaaacgggt 1380
ggctgcgtac cccagggaaa cggtcggccg ctggattgaa aaggactgcc atcaccgacg 1440
cacgctctgg tggaagagaa agctacactc tttgctctgc cgcattcatt cttttcttac 1500
cgtgatcctc tttgtctctt atcttttctt ttgtgtgtgt gtagccgttg gcgctgtctt 1560
cagggcattc cgctcttaag cgggtgctga cacattgacc atcgcttcag acttcctcgt 1620
tgtacggatg ttgccatcat aatcccaaag agcatcatgg ttaaaactgt ccatacgcac 1680
atttgtaaat aagaattgat tcacacatca gaaacatggt tgtacttagg ggtgcccaaa 1740
aatatttttg cccttttttg aataatgtat gaaagacaac ttaactttca ccaaaataaa 1800
ctagaaagct cagcgtgttt gtctttattc gctgctacac taacttcgag accaacggat 1860
aagaaagtta acggaataag agagcggtac ctttattacc tctctttaaa agaagttagc 1920
agcgatgaat ttgttgctct tttctctaag gcattcaata atttataagg cgtcgggtat 1980
ttcagttact caattattca atgaaacaat gtatcctaca tgacgagtac tggtcagtcg 2040
agatgcgttg ttttcccgac agttctcatt cagggttctt tccgagcgaa gactgattgc 2100
gtgctgccag actgattcgt tcttggcgat ttggtcgaaa cgtttgcgct tcctcattca 2160
gcgtccggcg tcagcaatat ttgcgcgtaa tccc 2194

<210> SEQ ID NO 5
<211> LENGTH: 422
<212> TYPE: PRT
<213> ORGANISM: Dermacentor variabilis

<400> SEQUENCE: 5

Met Ile Pro Ala Ser Val Ala Leu Gly Arg Arg Met Cys Ser Leu Leu
1 5 10 15

Leu Ala Val Gly Cys Ala Thr Thr Ser Ala Trp Phe Ala Gln Ala Val
20 25 30

Asp His Ile Asp Lys Gly Tyr Pro Ala Pro Gly Leu Phe Asp Asp Val
35 40 45

Asp Leu Gln Ile Leu Asp Asn Ile Leu Trp Ser Tyr Asp Arg Arg Ile
50 55 60

Thr Pro Gly His His Leu Asn Val Pro Thr Val Val Lys Cys Glu Ile
65 70 75 80

Tyr Leu Arg Ser Phe Gly Ala Val Asn Pro Ala Thr Met Asp Tyr Asp
85 90 95

Val Asp Leu Tyr Leu Arg Gln Thr Trp Thr Asp Leu Arg Met Lys Asn
100 105 110

Ala Asn Leu Thr Arg Ser Leu Asp Leu Asn Asp Pro Asn Leu Leu Lys
115 120 125

-continued

```
Lys Val Trp Lys Pro Asp Val Tyr Phe Pro Asn Ala Lys His Gly Glu
    130                 135                 140

Phe Gln Phe Val Thr Val Pro Asn Val Leu Leu Arg Ile Tyr Pro Thr
145                 150                 155                 160

Gly Asp Ile Leu Tyr Met Leu Arg Leu Lys Leu Thr Phe Ser Cys Met
                165                 170                 175

Met Asn Met Glu Arg Tyr Pro Leu Asp Arg Gln Val Cys Ser Ile Glu
            180                 185                 190

Leu Ala Ser Phe Ser Lys Thr Thr Lys Glu Val Glu Leu Gln Trp Gly
        195                 200                 205

Asn Ala Glu Ala Val Thr Met Tyr Ser Gly Leu Lys Met Ala Gln Phe
    210                 215                 220

Glu Leu Gln Gln Ile Ser Leu Thr Lys Cys Ser Gly Ala Phe Gln Ile
225                 230                 235                 240

Gly Glu Tyr Ser Cys Leu Arg Ala Glu Leu Asn Leu Lys Arg Ser Ile
                245                 250                 255

Gly His His Leu Val Gln Ser Tyr Leu Pro Ser Thr Leu Ile Val Val
            260                 265                 270

Val Ser Trp Val Ser Phe Trp Leu Asp Val Asp Ala Ile Pro Ala Arg
        275                 280                 285

Ile Thr Leu Gly Val Thr Thr Leu Leu Thr Ile Ser Ser Glu Ser Ser
    290                 295                 300

Asp His Gln Ala Asn Leu Ala Pro Val Ser Tyr Val Lys Ala Leu Asp
305                 310                 315                 320

Val Trp Met Gly Thr Cys Thr Met Phe Val Phe Ala Ala Val Leu Glu
                325                 330                 335

Phe Thr Phe Val Ser Tyr Leu Ala Arg Arg Lys Gln Ile Val Pro Ala
            340                 345                 350

Ser Ile Ala Asp Val Glu Ala Ser Gln Asp Leu Val Leu Val Val Gly
        355                 360                 365

Asn Lys Asp Lys Asn Arg Pro Pro Ser Pro Ser Ile Pro Thr Ser Thr
    370                 375                 380

His Val Val Leu Ala Tyr Arg His Arg Ala Lys Gln Ile Asp Gln Val
385                 390                 395                 400

Ser Arg Val Ala Phe Pro Ile Gly Phe Val Leu Phe Asn Ala Leu Tyr
                405                 410                 415

Trp Pro Tyr Tyr Leu Leu
            420

<210> SEQ ID NO 6
<211> LENGTH: 4077
<212> TYPE: DNA
<213> ORGANISM: Dermacentor variabilis

<400> SEQUENCE: 6
cggaccggtc ggcccacttt ctcctttcat gacgcgccgt gatcacgcgg cgtgacaccc      60
agcgtcgcct ctacgtttca ttcatttcgt gtctccgcct gcggtgcgcc tgccgcgtga     120
cgcaaccggg cgcatgacac cgccgaaccc tctgtcgtcg gcgcatcgcg tcctggcgct     180
gctcctgctg gtgacagtgc cggcttctct ggggcagagg agacatggaa ctgtcggcga     240
tttggacaag ttggacaaac tcctgagcaa atatgacaga agggcgttgc caacggggca     300
catgagatta cgaagtggac ctctacctgc gacaacgatg gcatgatgac cgctttgaga     360
tgagcggcat tagtggaccc ctcgacctga acgatcccaa actggtgcaa cgtatatgga     420
aacccgaagt ctttttgcc aacgcaaagc atgcggagtt ccagtacgtg acggtgccca      480
```

```
acgtcctagt acgcatcagt cctacggggg acattctcta catgctcagg ttgaagctga    540 cttttttcttg catgatggac ctttaccggt accccctaga cgctcaagtt tgcagcattg   600
aactcgcttc gttctcgaag acgacggacg agctacagct gcactggtct aaggcatcgc    660
ctgtgatcct ctatgaaaac atgaagctcc cacaatttga aattcaaaac gtgaacacgt    720
ccctgtgcaa tgagacattc acattggag agtacagctg cctgaaagcc gagttcaacc     780
tacagcgctc tattggctac cacctcgtcc aatcgtatct gcccaccatc ttgatcgtgg    840
tcatctcttg ggtctccttc tggctcgacg tggaagcgat tccagcccga attacattgg    900
gagtcaccac gcttcttacc atctcatcca agggtgccgg tatacaagga aacctgccgc    960
ccgtctcgta cgtcaaggca atcgacgtct ggatgggcgc ctgcaccatg ttcgtgtttg   1020
ccgcactgct tgagttcacc tttgtcaact acctgtggag gaagcggccc gcgactgcca   1080
agtcaccacc tccggtggtc gcagccattc ccgagagcaa agtggctgtg ctcctcccat   1140
gcaacggaaa cttgggggcca tgcagcccca tcactggcgg tacagacatc agcccttcgc  1200
ccacaggtcc tgaagctgtc agaaacagac acaaggttca ggccaagaga attgaccaga   1260
cctgcaggat agcatttccc atggcttttcc tggcgtttag cgtcgcatac tggccatact   1320
atcttttgtg aggccgcggt accccgagct aatgtcagga acggagaggc gggtaccacg   1380
aagtcggggg ggggggggag gggggagagt gcttgtggct atcacaatcc cgttggttct   1440
ctgtaagaac gcttttgttt tgcacagaag ctcactgcat cacattttgc gtctccctag   1500
tgtttaatta tttgtttctg cacttgtgtt cccgtgtgca ttctgactga atatcactcc   1560
aacccttcag tgtgtataag tcccaaagtg aattggatat ttcctcttcg cgatcctctt   1620
gagggcacct ctagtcacta atctaacacg taggagagtt taaggatgcg ttaggcagca   1680
cttttcttgt gctttaagtg gatctcatca tattctggta gagaatataa acttcaacac   1740
tgaagtagta tttacaaggc agactaacat gttgctagaa acagtatttt tgcaggaggg   1800
aagatgcaat gattatacag ggtgttcaaa attaagcttt atggttttat aggaattagg   1860
cactgcgagg ggaagggcaa ccgttatcgt cttttgtctat gcctccgccc tattgtcaga   1920
ctaaatgccg cacacaacag cctcgtcaca tcagggaaga tctttgtgcc aatcctcact   1980
ctcttgcgtg cgtaatcacg taaacgacaa ttaaaatttg gagccagcta tctcgaagca   2040
aagatatgct ggaagaattc ttctaagtgt aactgtgtag aaactttttca atacacaaat  2100 acacacttac tgcagtcaat aaaaagttaa ttactcgatt ttatttaatt gggctgctga   2160
cagcaataac tctcatctca ctttgtgtcc cctggccac ataacttatt tgcacaggtg     2220
gtcttcgcgt gcatcccagt ggctaaattt aagaaaacca taaagcttaa ttttgaacac   2280
ctggtatatc atgatgcttt caatgctttta ttgttgtatt ataaaaaaag atatactatc   2340
aacgactcag gccggagaat catgttggaa aaaaaatgtt tcattgtttc ctttcgtcat    2400
cgcgccctta ggttaatttg ccctgtacag ttcctgaggg aacgcattag tgcacaaaaa    2460
aagtatttcg gcttccacat cgcaacgaaa acgggcgtcg cctcctgtct ctacaagaca    2520
atgagatgcg caggccgcac gcttttttcgg ggtccgcaat tattaaacat ggcgtatatt   2580
ttgataaccc gcaccttctt cctacgcagc attttttctgt tagacccact gggttcattt   2640
aaccaatcct aggcctaaaa ccgtattcaa gcccagcaca aagtccgctt ttgcgaactc    2700
ccgttcagat gtggatgagc cgttggctta caggactctg acctaagtat gggcctgtgt    2760
caaacgcgct cagaaagatg agcacaacag ccccttattg cgtaacgctg ccggcaatgc    2820
tcgccatttt aagctgtccc gaactgcgaa attattccac ggtagcgctt ttgtagatgt    2880
```

```
ggaagacttg cctaatcact tcaaaggtgt cgccacttac aatactatac gtacagttcc   2940
gcctggagaa tttggcgcac gcatacttgt agtaccatga ggcggagtta ttacttcggg   3000
aggaattgcg caggcagcta atccccatct acgcaactct ggacagtcgg atgttatgca   3060
tggtaggaga atggactata aagggtgga gtctgcaagt caggcgagga tacagcggcg   3120
tagcgaaaac gtagccatgc ttgtggagta cacgacccga ctcttgtgaa cacggatcc    3180 atctatgtcg gaaacaaaaa tttaagcact tcatgcgcgc agtaaagaaa gaaccctttg   3240
ggggcctgat accaaacttg cccaagaacc tcccagagta cctcgcagag gccatgtcaa   3300
aggaaaagac gatctagcag taggatcctg atttggcttt ggacaacgtc gctgtaatgc   3360
gagtgcttat aaagttcttt gttctggaag aggttaaatg ctccatctaa ctccaggctc   3420
tgtactgcgg acttcgccgg ctgaggtcgt tcgttagaag atggggcgtg ctgcccgaac   3480
ctcagaatat ttcggagcgc cactgtacga ggtgcggcag ctggcacttt gaatcaccta   3540
tgcggaagct gcgcgaggtt ctccacacta ggactcccac aatgtgcgcg cccttgaaca   3600
agcgattgcc aacttcagag cccgcggcga ccaatcaaag ctgaagtatg tcatcgcaaa   3660
acttatattt atcgaacctc aattggaaag accatgtatt tcactgcgc tgtggaacat    3720 gaaatttatg cgttacatat tcgctccggg gaatagcaaa atattgcaa aaatattggt     3780 gacacagaaa gcagtcgcat atcaagccca ttatatgcgt tgacgctgta gtttgtaaag   3840
ggcacttgaa tgtggacgcc tgtttagaat cgcggagaga tttcattttc gcggagctta   3900
taccactctc aaatgtgctg ggcacggca gaatcgtgga tccagttttt ttaacttccg    3960
tcaaaacaga ttagcagtag ttcacagcgg cgaaacactc acaagtgtag ttataaaaac   4020
ctaacagttt gaatcaataa atatttgaca tcaaaaaaaa aaaaaaaaaa aaaaaaa      4077
```

<210> SEQ ID NO 7
<211> LENGTH: 323
<212> TYPE: PRT
<213> ORGANISM: Dermacentor variabilis

<400> SEQUENCE: 7

```
Met Ser Gly Ile Ser Gly Pro Leu Asp Leu Asn Asp Pro Lys Leu Val
 1               5                  10                  15

Gln Arg Ile Trp Lys Pro Glu Val Phe Phe Ala Asn Ala Lys His Ala
            20                  25                  30

Glu Phe Gln Tyr Val Thr Val Pro Asn Val Leu Val Arg Ile Ser Pro
        35                  40                  45

Thr Gly Asp Ile Leu Tyr Met Leu Arg Leu Lys Leu Thr Phe Ser Cys
    50                  55                  60

Met Met Asp Leu Tyr Arg Tyr Pro Leu Asp Ala Gln Val Cys Ser Ile
65                  70                  75                  80

Glu Leu Ala Ser Phe Ser Lys Thr Thr Asp Glu Leu Gln Leu His Trp
                85                  90                  95

Ser Lys Ala Ser Pro Val Ile Leu Tyr Glu Asn Met Lys Leu Pro Gln
            100                 105                 110

Phe Glu Ile Gln Asn Val Asn Thr Ser Leu Cys Asn Glu Thr Phe His
        115                 120                 125

Ile Gly Glu Tyr Ser Cys Leu Lys Ala Glu Phe Asn Leu Gln Arg Ser
    130                 135                 140

Ile Gly Tyr His Leu Val Gln Ser Tyr Leu Pro Thr Ile Leu Ile Val
145                 150                 155                 160

Val Ile Ser Trp Val Ser Phe Trp Leu Asp Val Glu Ala Ile Pro Ala
```

|     |     |     |     |     | 165 |     |     |     | 170 |     |     |     | 175 |     |
| --- | --- | --- | --- | --- | --- | --- | --- | --- | --- | --- | --- | --- | --- | --- |
| Arg | Ile | Thr | Leu | Gly | Val | Thr | Thr | Leu | Leu | Thr | Ile | Ser | Ser | Lys | Gly |

Arg Ile Thr Leu Gly Val Thr Thr Leu Leu Thr Ile Ser Ser Lys Gly
                180                 185                 190

Ala Gly Ile Gln Gly Asn Leu Pro Pro Val Ser Tyr Val Lys Ala Ile
        195                 200                 205

Asp Val Trp Met Gly Ala Cys Thr Met Phe Val Phe Ala Ala Leu Leu
210                 215                 220

Glu Phe Thr Phe Val Asn Tyr Leu Trp Arg Lys Arg Pro Ala Thr Ala
225                 230                 235                 240

Lys Ser Pro Pro Val Val Ala Ala Ile Pro Glu Ser Lys Val Ala
                245                 250                 255

Val Leu Leu Pro Cys Asn Gly Asn Leu Gly Pro Cys Ser Pro Ile Thr
            260                 265                 270

Gly Gly Thr Asp Ile Ser Pro Ser Pro Thr Gly Pro Glu Ala Val Arg
        275                 280                 285

Asn Arg His Lys Val Gln Ala Lys Arg Ile Asp Gln Thr Cys Arg Ile
        290                 295                 300

Ala Phe Pro Met Ala Phe Leu Ala Phe Ser Val Ala Tyr Trp Pro Tyr
305                 310                 315                 320

Tyr Leu Leu

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggatattgg acagcatc                                                 18

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccagtagacg aggttgaaga gg                                            22

<210> SEQ ID NO 10
<211> LENGTH: 1197
<212> TYPE: DNA
<213> ORGANISM: Rhipicephalus sanguineus

<400> SEQUENCE: 10
cggatattgg acagcatcat tggccagggt cgttatgact gcaggatccg gcccatggga      60
attaacaaca cagacgggcc ggctcttgta cgcgttaaca tctttgtaag aagtatcggc     120
agaattgatg acgtcaccat ggagtacaca gtgcaaatga cgttcagaga gcagtggcgg     180
gacgagagac tccagtacga cgacttgggc ggccaggttc gctacctgac gctcaccgaa     240
ccggacaagc tttggaagcc ggacctgttt ttctccaacg agaaagaggg acacttccac     300
aacatcatca tgcccaacgt gcttctacgc atacatccca acggcgacgt tctcttcagc     360
atcagaaata ccttggtgct ttcatgtccg atgaacctga aatttatcc tttggataaa     420 caaatctgct ctatcgtcat ggtgagctat ggtatacaa cagaggacct ggtgtttcta     480

```
tggaaagagg gggatcctgt acaggtcaca aaaaatctcc acttgccacg tttcacgctg      540
gaaaggtttc aaaccgacta ctgcaccagt cggaccaaca ctggcgagta cagctgcttg      600
cgcgtggacc tggtgttcaa gcgcgagttc agctactacc tgatccagat ctacatcccg      660
tgctgcatgc tggtcatcgt gtcctgggtg tcgttctggc tcgaccccac ctcgatcccg      720
gcgcgagtgt cgctgggcgt caccaccctg ctcaccatgg ccacgcagat atcgggcatc      780
aacgcctcgc tgcctcccgt ttcctacacc aaggccattg acgtgtggac cggcgtctgt      840
ctgaccttcg tattcggcgc gctcctcgag ttcgccctgg tcaactacgc ctcgcggtca      900
gattcacgcc ggcagaacat gcagaagcag aagcagagga atgggagct cgagccgccc       960 ctggactcgg accacctgga ggacggcgcc accacgttcg ccatgaggcc gctggtgcac     1020
caccacggag agctgcatgc cgacaagttg cggcagtgcg aagtccacat gaagacccc     1080 aagacgaacc tttgcaaggc ctggcttttc aggtttccca cgcgatccaa acgcatcgac     1140
gtcgtctcgc ggatcttctt tccgctcatg ttcgccctct tcaacctcgt ctactgg       1197

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtggtggtg atagctgc                                                    18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gagttgatca atctgcttgg                                                  20

<210> SEQ ID NO 13
<211> LENGTH: 1150
<212> TYPE: DNA
<213> ORGANISM: Rhipicephalus sanguineus

<400> SEQUENCE: 13
tgtggtggtg atagctgcgt tctgctggcc gcccgctctg ccgctcgtac ccgggggagt       60
ttcctccaga gcaaacgatc tggacattct ggacgagctc ctcaaaaact acgatcgaag      120
ggccctgccg agcagtcacc tcggaaatgc aactattgtg tcatgcgaaa tttacatacg      180
aagttttgga tcaataaatc cttcgaacat ggactacgaa gtcgacctct acttccggca      240
gtcgtggctc gacgagcggt tacgcaaatc cacgctatct cgtccgctcg accttaatga      300
cccaaagctg gtacaaatga tatggaagcc agaagttttc tttgcgaacg cgaaacacgc      360
cgagttccaa tatgtgactg tacctaacgt cctcgttagg atcaacccga ctggaataat      420
cttgtacatg ttgcggttaa aactgaggtt ctcctgcatg atggacctgt accggtaccc      480
catggattcc caagtctgca gcatcgaaat tgcctctttt tccaaaacca ccgaagagct      540
gctgctgaaa tggtccgaga gtcagcctgt cgttctcttc gataacctca gttgccca       600 gtttgaaata gagaaggtga acacgtcctt atgcaaagaa aagtttcaca taggggaata     660
```

```
cagttgcctg aaagccgact tctatctgca gcgttccctc ggttatcaca tggtgcagac    720
ctatcttccg accacgctta tcgtggtcat ctcatgggtg tcattctggc tcgacgtaga    780
cgccataccc gcccgtgtca ccctgggcgt aaccacgctg ctcaccatct catccaaggg    840
tgccggtatc cagggaaacc tgcctcccgt ctcgtacatc aaggccatgg acgtctggat    900
aggatcctgt acttcgtttg tctttgcggc ccttctagag ttcacattcg tcaactatct    960
ctggaggcgg ctgcccaata agcgcccatc ttctgacgta ccggtgacgg ataccaag    1020 cgacggctca aagcatgaca ttgcggcaca gctcgtactc gacaagaatg gacacaccga    1080
agttcgcacg ttggtccaag cgatgccacg cagcgtcgga aaagtgaagg ccaagcagat    1140
tgatcaactc                                                          1150
```